United States Patent
Gersh et al.

(10) Patent No.: US 8,435,034 B2
(45) Date of Patent: May 7, 2013

(54) ROTATABLE ULTRASONIC DENTAL TOOL

(75) Inventors: Mark Gersh, Los Angeles, CA (US); Pejman Fani, San Diego, CA (US); John Raybuck, Los Angeles, CA (US)

(73) Assignee: Zila, Inc., Fort Collins, CO (US)

( * ) Notice: Subject to any disclaimer, the term of this patent is extended or adjusted under 35 U.S.C. 154(b) by 0 days.

(21) Appl. No.: 12/406,290

(22) Filed: Mar. 18, 2009

(65) Prior Publication Data

US 2011/0033823 A1 Feb. 10, 2011

Related U.S. Application Data

(60) Provisional application No. 61/037,689, filed on Mar. 18, 2008, provisional application No. 61/089,650, filed on Aug. 18, 2008.

(51) Int. Cl.
*A61C 1/07* (2006.01)
(52) U.S. Cl.
USPC ............................................. 433/119; 433/86
(58) Field of Classification Search .................. 433/86, 433/199, 119; 128/200.16; 451/165, 910; 318/116, 118; 601/80; 606/169, 171, 177, 606/178, 167, 170; 604/22
See application file for complete search history.

(56) References Cited

U.S. PATENT DOCUMENTS

| | | | |
|---|---|---|---|
| 3,706,514 A * | 12/1972 | Ruf | ................................ 418/104 |
| 4,069,444 A | 1/1978 | Heim | |
| 4,148,309 A | 4/1979 | Reibel | |
| 4,840,563 A | 6/1989 | Altendorf | |
| 4,900,252 A | 2/1990 | Liefke | |
| 5,185,004 A * | 2/1993 | Lashinski | ................... 604/95.04 |
| 5,267,860 A | 12/1993 | Ingram et al. | |
| 5,382,162 A | 1/1995 | Sharp | |
| 5,476,379 A * | 12/1995 | Disel | ................................ 433/29 |
| 5,927,977 A | 7/1999 | Sale et al. | |
| 6,086,369 A | 7/2000 | Sharp et al. | |
| 6,095,810 A | 8/2000 | Bianchetti | |
| 6,386,866 B1 | 5/2002 | Hecht et al. | |
| 6,503,081 B1 | 1/2003 | Feine | |
| 6,616,446 B1 | 9/2003 | Schmid | |
| 6,716,028 B2 * | 4/2004 | Rahman et al. | ................ 433/119 |
| 6,735,802 B1 | 5/2004 | Lundell et al. | |
| 6,899,538 B2 | 5/2005 | Matoba | |

(Continued)

FOREIGN PATENT DOCUMENTS

| | | |
|---|---|---|
| WO | 2005/002458 | 1/2005 |
| WO | 2005053561 | 6/2005 |
| WO | 2006089104 | 8/2006 |
| WO | 2006125066 | 11/2006 |

*Primary Examiner* — Heidi M Eide
(74) *Attorney, Agent, or Firm* — Jeffer Mangels Butler & Mitchell LLP

(57) ABSTRACT

The present invention describes an ultrasonic dental insert capable of enhanced operating efficiency. A first transducer generates ultrasonic vibrations. A connecting body has a proximal end and a distal end having a tip attached thereto. The proximal end is attached to the first transducer so as to receive the ultrasonic vibrations therefrom and to transmit the ultrasonic vibrations toward the tip attached to the distal end. The ultrasonic dental insert may be inserted into a handpiece for providing electromagnetic energy to the first transducer to generate the ultrasonic vibrations. The ultrasonic insert, when seated in the handpiece, is substantially decoupled, on a rotary axis, from the handpiece. A rotary force need only be applied to the insert to rotate it in the handpiece. At least one light source substantially proximate or distal to the tip may also be provided.

18 Claims, 28 Drawing Sheets

U.S. PATENT DOCUMENTS

| | | |
|---|---|---|
| 6,955,536 B1 | 10/2005 | Buchanan |
| 6,994,546 B2 | 2/2006 | Fischer et al. |
| 7,104,794 B2 | 9/2006 | Levy |
| 7,596,827 B1 | 10/2009 | Puneet |
| 2002/0088068 A1 | 7/2002 | Levy |
| 2004/0059363 A1* | 3/2004 | Alvarez et al. ............... 606/170 |
| 2004/0185412 A1 | 9/2004 | Feine |
| 2004/0255409 A1 | 12/2004 | Hilscher et al. |
| 2004/0259054 A1 | 12/2004 | Mayer |
| 2005/0032017 A1 | 2/2005 | Levy |
| 2005/0050658 A1 | 3/2005 | Chan et al. |
| 2006/0154209 A1 | 7/2006 | Hayman et al. |
| 2006/0234185 A1* | 10/2006 | Ziemba ..................... 433/119 |
| 2006/0269900 A1 | 11/2006 | Paschke et al. |
| 2007/0011836 A1 | 1/2007 | Brewer et al. |
| 2007/0031782 A1 | 2/2007 | Warner et al. |
| 2008/0265565 A1* | 10/2008 | Sitz et al. ..................... 285/98 |

* cited by examiner

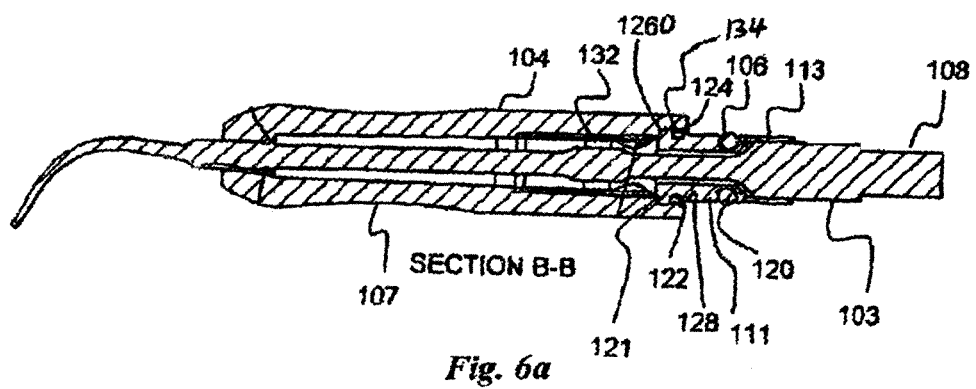
*Fig. 6a*
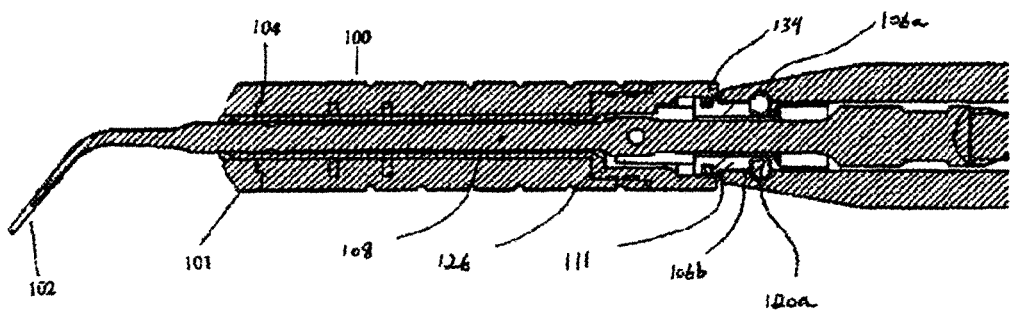
*Fig. 6B*
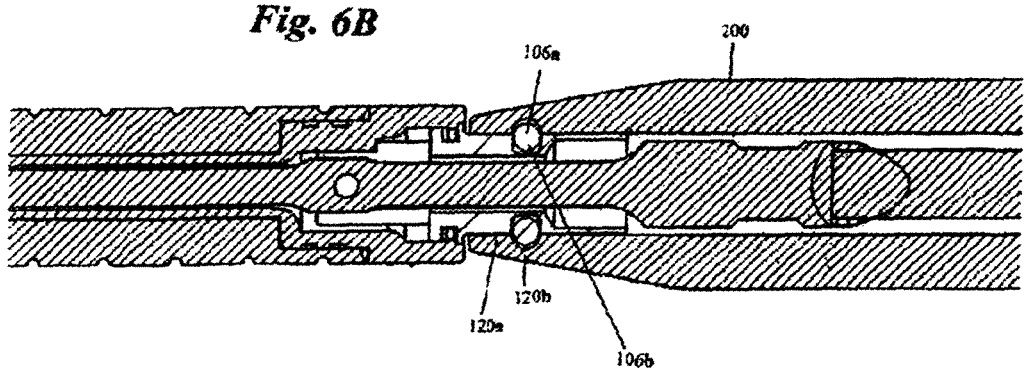

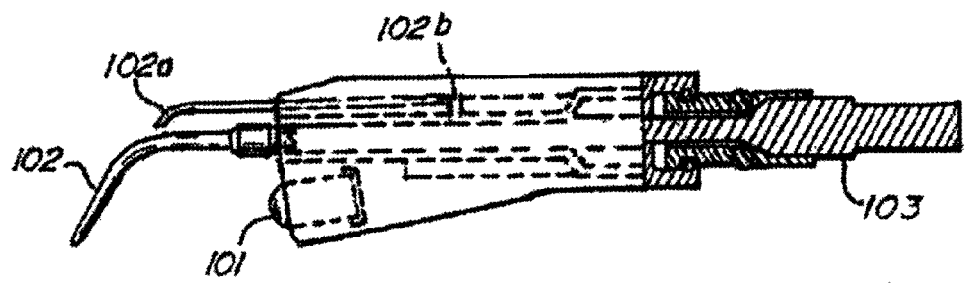
*Fig. 7A*
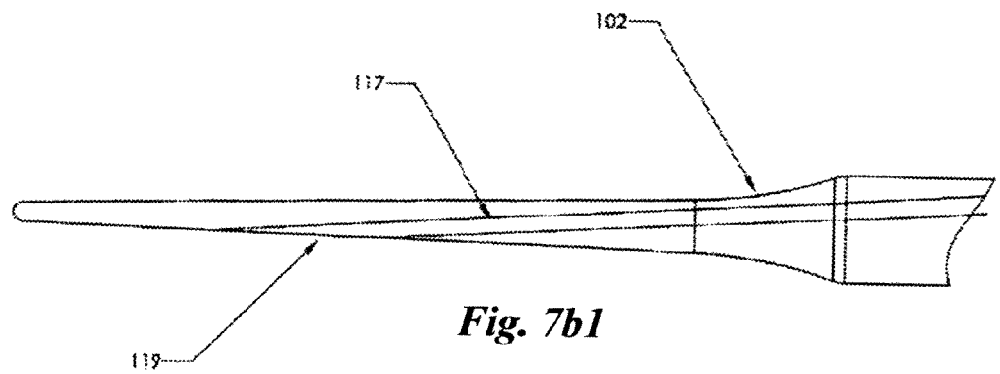
*Fig. 7b1*
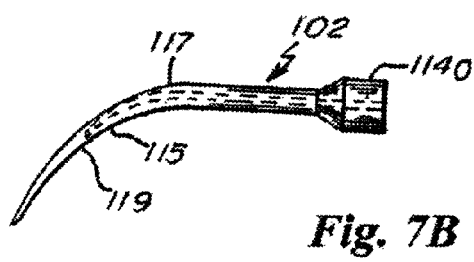
*Fig. 7B*
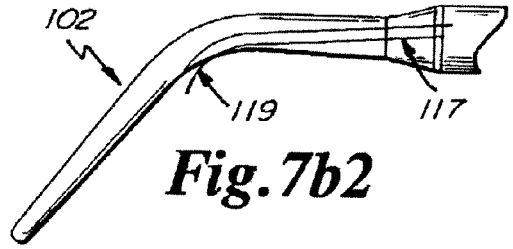
*Fig. 7b2*
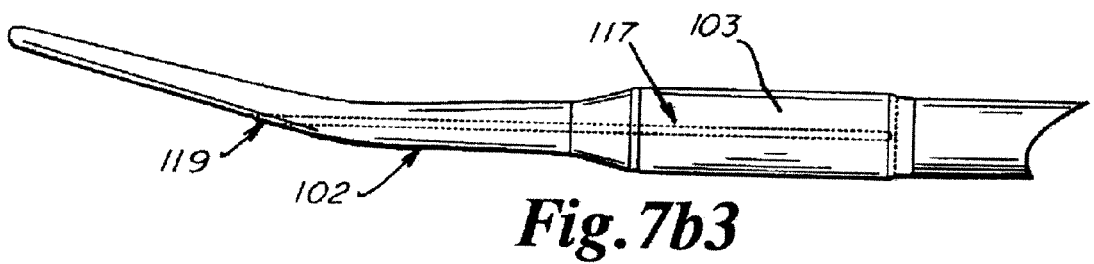
*Fig. 7b3*

Fig. 7b4

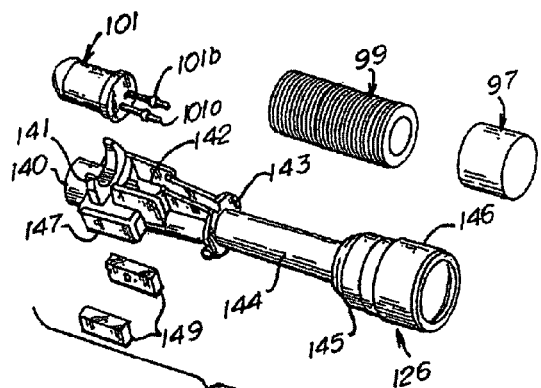
*Fig. 7D1*
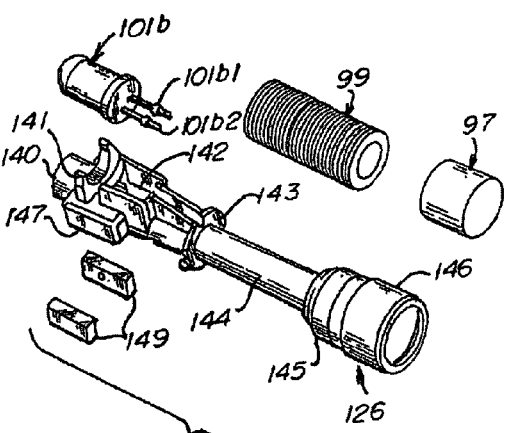
*Fig. 7D.2*
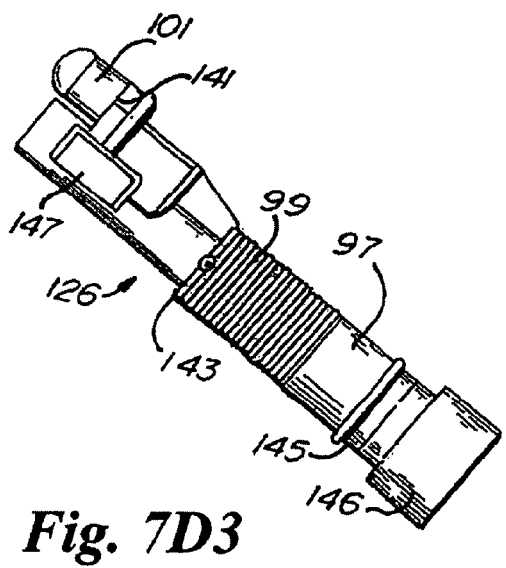
*Fig. 7D3*
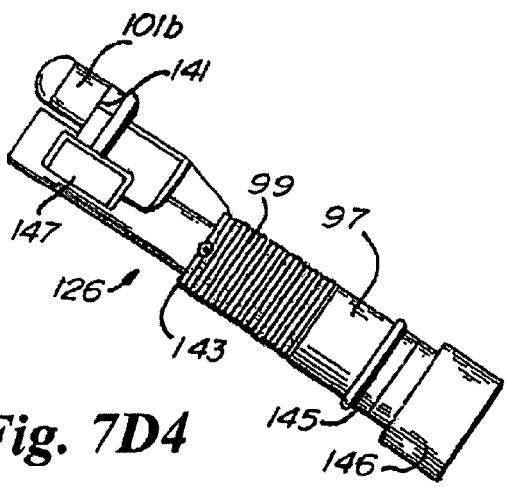
*Fig. 7D4*

Fig. 7D.5

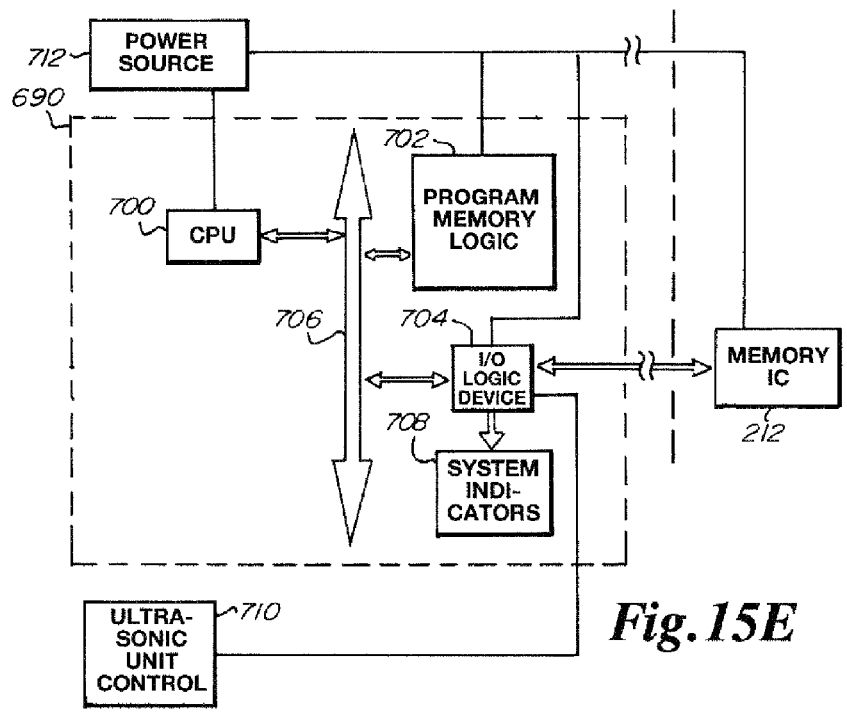
*Fig. 15E*
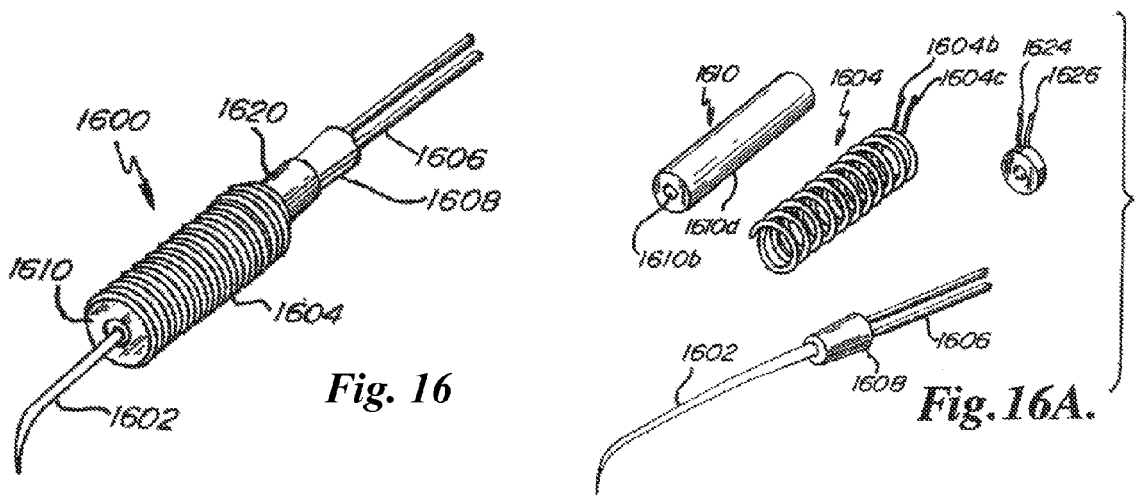
*Fig. 16*
*Fig. 16A.*

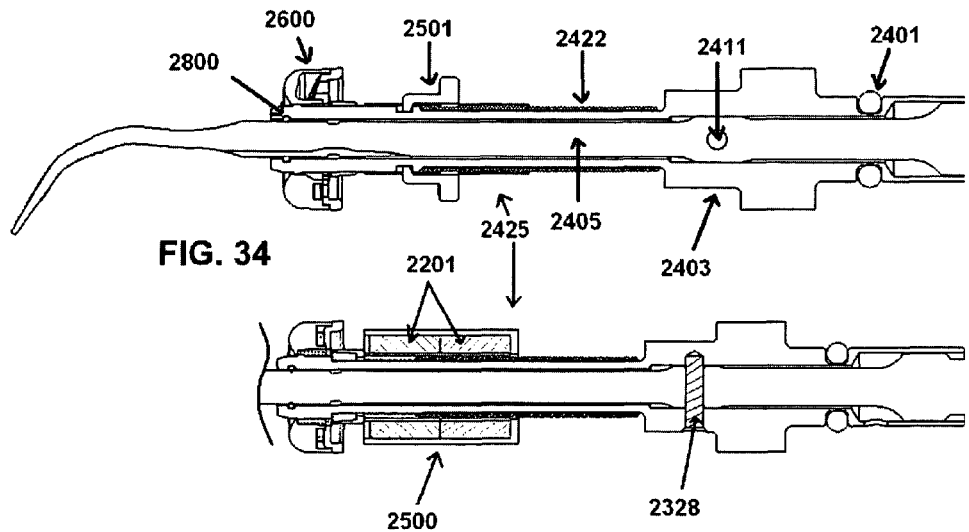
FIG. 34
FIG. 34a
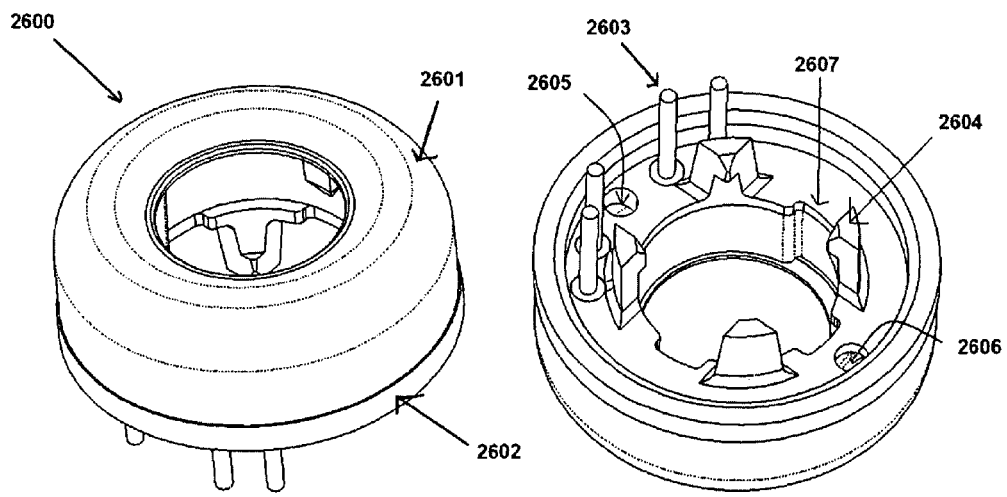
Fig. 35
Fig. 35a

ROTATABLE ULTRASONIC DENTAL TOOL

This application claims the benefit of U.S. provisional patent application No. 61/037,689, filed on Mar. 18, 2008, titled "ROTATABLE ULTRASONIC DENTAL TOOL" and provisional application No. 61/089,650, filed on Aug. 18, 2008, titled "ROTATABLE ULTRASONIC DENTAL TOOL", the content of which is hereby incorporated by reference.

FIELD OF THE INVENTION

The present invention is related to ultrasonic dental tools, and more particularly to an ultrasonic dental tool capable of enhanced operation efficiency.

BACKGROUND

Dental practitioners use ultrasonic dental tools (instruments) for dental treatments and procedures, such as scaling, periodontal treatments, root canal therapy, and the like.

An ultrasonic dental tool typically includes a handpiece coupled at one end (i.e., a proximal end) to an electrical energy source and a fluid source via a cable. The cable includes a hose to provide a fluid (e.g., water), and conductors to provide electrical energy. The other end (i.e., a distal end) of the handpiece has an opening intended to receive a replaceable insert with a transducer (e.g., a magnetostrictive transducer) carried on the insert. The transducer extends from a proximal end of the insert into a hollow interior of the handpiece. An ultrasonically vibrated tip extends from a distal end of the insert.

When using a typical ultrasonic insert during a cleaning procedure, the dental practitioner will need to repeatedly re-orient the location of the insert tip with respect to tooth surface. In making this re-orientation, the practitioner will typically take the insert out of the patient's mouth, rotate the insert inside the handpiece to re-orient the tip and re-insert the insert in the patient's mouth. This is done because the handpiece is tethered to a power and fluid supply source, so that rotation of the handpiece is limited.

Both hands are typically used for this rotation as the frictional forces that produce a tight fit of the insert in the handpiece needs to be overcome. During a typical treatment process, an insert is reoriented numerous times. This is not only time consuming but also interrupts the ease and smooth flow of work.

SUMMARY OF THE INVENTION

The present invention relates to an ultrasonic dental tool having an insert that is rotatable about a handpiece when the insert is disposed inside the handpiece, such rotation may be effected about a longitudinal axis of the insert by applying a force only to the insert. The rotation may be effected single handed, for example, or a two finger rotation is also possible. The dental tool utilizes existing components to effect this rotation. The handpiece may be any generally available handpiece or, if desired, a specially designed handpiece. Additional parts to facilitate rotation may also be present.

The insert includes a motor, a work tip, and a coupling member disposed between said motor and said work tip. The coupling member is adapted to receive mechanical energy from said motor. The handpiece includes a substantially hollow interior, and open at both ends. The dental insert is rotatably received in an opening at one end of the handpiece, and the other end (i.e., a proximal end) of the handpiece is typically coupled to an electrical energy source and a fluid source via a cable. The cable includes a hose to provide a fluid (e.g., water), and conductors to provide electrical energy. The energy supply serves to operate the motor on the insert.

During operation, water is circulated in the handpiece to, for example, keep the motor from overheating. To seal the motor portion of the handpiece where water is circulated, to lavage the motor and keep it from over-heating, as well as to keep the water from the tip portion, an O-ring is generally used. The O-ring generally sits in a groove disposed somewhere on the coupling member, such as the connecting body, of the insert. In one embodiment, the O-ring may be disposed on a retaining ring or collet present on the connecting body. The retaining ring has a groove to accommodate the O-ring. In another embodiment, there may not be a collet or retaining ring and the groove may be on the coupling member or connecting body.

Typically, because of the sealing action of the O-ring, rotation of the insert about the O-ring is difficult, and generally requires both hands with some force. In the present invention, the O-ring and the groove the O-ring may be seated collaboratively to both seal and facilitate freer rotation of the insert within the handpiece, for example, about the O-ring. The groove may be on the connecting body in one embodiment. In another embodiment, a retaining ring or collet may be disposed on the connecting body, in which case, the groove may be present on the retaining ring or collet.

In one embodiment of the invention, the structure of the O-ring is the same or substantially the same as that of the traditional O-ring, but the surface of the groove it is seated or in contact with, either on the connecting body or the retaining ring, has a reduced frictional force to enable the insert to rotate easily while still maintaining a proper seal.

In another embodiment of the invention, the O-ring and the surface of contact in the groove on the insert both may have reduced frictional forces. In one aspect, the frictional force between the O-ring and the handpiece is high, and the frictional force between the O-ring and the groove on the insert is low. This reduced frictional force between the O-ring and the contact surface of the groove enables freer rotation of the insert, while at the same time, there is sufficient axial friction between the insert, i.e., the outer peripheral of the O-ring, and the handpiece to substantially prevent the insert from popping out of the handpiece due to water pressure within the handpiece and/or drag by the handpiece cable during use. In another aspect, the frictional force between the O-ring and the handpiece and the frictional force between the O-ring and the groove on the insert may both be low, and the O-ring may fit into a groove in the handpiece, or the outer peripheral of the O-ring may be notched or grooved to mate with a protrusion in the wall of the handpiece, so that the insert is likewise not likely to pop out of the handpiece.

In one exemplary embodiment, the surface of the groove on the connecting body or retaining ring, when present, for seating the O-ring, may have a low coefficient of friction. In one aspect, the surface of the groove may be coated with a material having a low coefficient of friction. In another aspect, the surface of the groove may be made to have a low coefficient of friction. In yet another aspect, both surfaces of contact (in the O-ring and the groove of the insert) may be made of or coated with a material or a coating of a material having a low coefficient of friction. In yet a further aspect, both surfaces of contact may be made to substantially eliminate irregularities to reduce the coefficient of friction.

In another exemplary embodiment, the O-ring may be made of a material having a low coefficient of friction about the inner peripheral and a high coefficient of friction about the outer peripheral to enable this freer rotation and secure placement.

In yet another exemplary embodiment, the O-ring may have a coating made of a material having a low coefficient of friction about the inner circumference to enable this freer rotation.

In yet a further exemplary embodiment, a dual hardness o-ring having a different hardness/material in the bulk of the O-ring from that of the outer peripheral portion of the o-ring is contemplated. In one aspect, a lower hardness material on the outer peripheral portion may enable the outside surface of the o-ring to grip the wall of the handpiece (cylinder) while the higher hardness material on the inner peripheral portion of the O-ring may allow the insert (piston) to rotate more freely.

When a coating is used, material for the coating may be any that is capable of producing a surface with low coefficient of friction.

In other embodiments of the invention, an additional O-ring may be included so as to create a more uniform rotational interface and improving the sealing characteristics.

With a low coefficient of friction in the contact region, the torque needed to overcome the coefficient to cause rotation of the insert inside the handpiece is smaller enough so that the rotation may be effected with one hand for any of the above noted embodiments. In general, the torque may be in the range of less than about 500 g·cm, more for example, in the range of less than about 400 g·cm, even more for example, in the range of 10 g·cm-300 g·cm, and still more for example, in the range of 45 g·cm-200 g·cm.

The dental insert of the present invention may have a 360 degrees rotation, without any limitations. This may enable a dental practitioner to position the insert, and the work tip, at any angular orientation without having to take the insert out of the patient's mouth. Therefore, time associated with re-orienting the tip a number of times during the dental treatment is reduced, and the flow of work is not interrupted as much, thereby resulting in a smooth work flow and a reduction of time.

In one embodiment, the motor may be a magnetostrictive transducer. In another embodiment, the motor may be a piezoelectric transducer.

In one aspect, the present invention also relates to an ultrasonic dental insert having at least one light source. The dental insert includes a first motor, for example, a transducer, for generating ultrasonic vibrations and a coupling member such as a connecting body, having a proximal end and a distal end. The distal end includes a work tip thereon. The proximal end is attached to the first transducer so as to receive the ultrasonic vibrations therefrom and to transmit the ultrasonic vibrations toward the work tip at the distal end. The ultrasonic dental insert may also include a hand grip portion and may be inserted into a handpiece for providing electromagnetic energy to the first transducer to generate the ultrasonic vibrations, to form an ultrasonic dental tool having a light source.

In an exemplary embodiment, an electrical generator, for example, a second transducer may be disposed on the insert, for example, proximate to the connecting body, and generates a voltage signal in response to movement of a portion of the connecting body according to the ultrasonic vibrations. At least one light source, substantially proximate to the tip, may be connected to and receives the voltage signal from the second transducer to generate light. The second transducer circuitry may also include a form of rectification circuitry that may improve utilization of the alternating current of the voltage signal.

In one embodiment, the second transducer may include a bobbin having an illumination coil thereon. In one aspect, the bobbin may be formed separately from the retaining ring. In another aspect, the retaining ring may be made integral, for example, in one piece, with the bobbin. In this latter aspect, the unitary structure may be made from a high temperature material.

In another exemplary embodiment, the dental insert and/or handpiece may include a magnetic material or a magnetic source in close proximity to the first transducer, light source, or the second transducer, for initiating, re-establishing, increasing and/or maintaining the brightness of the output light from the light source when in use. In one aspect, the light source may be proximate the work tip. In another aspect, the light source may be away from the work tip. The light from the light source may be transmitted towards the tip using a light guide or light pipe.

In yet another exemplary embodiment, an ultrasonic dental tool may include at least one attachable light source. The attachable light source may utilize the existing energy source already present. In one embodiment, the light source is adapted to connect to the electrical energy source already available in the existing ultrasonic dental unit, using at least one connector. The at least one connector may be, for example, two wire leads, or at least one contact structure, that are adapted to be connected to respective connectors in the handpiece. In one aspect, the wire leads, for example, are situated in, for example, male or female plug type pins that may protrude from the housing of the insert. In another aspect, the contact structures, for example, may be formed onto and towards the proximal end of the connecting body and may be protruding also from the housing.

In a further exemplary embodiment, the ultrasonic dental tool may have an integral sheath and at least one light source adapted to utilize the electromagnetic energy already available in the existing ultrasonic dental unit. In one embodiment, the handpiece includes a substantially hollow housing having a primary power source that may include a primary coil and the insert may include the sheath. The primary coil of the handpiece may be inductively coupled to an illumination energy coil, either in the insert or handpiece, such that the illumination energy coil may draw energy from the electromagnetic field of the primary coil to power at least one light source.

In one embodiment of the invention, an ultrasonic dental tool that includes one of the ultrasonic dental inserts discussed above may be inserted into a handpiece having a hand grip portion. The insert maybe freely rotatable inside the handpiece, as discussed above.

In another aspect, the present invention relates to ultrasonic dental tools having an insert that includes monitoring mechanism(s) for monitoring insert usage and performance as well as an indication mechanism(s) for indicating timing for insert replacement. The insert may be any of those discussed above.

The advantages of the present invention are that rotation can be effected with any handpiece, and are realizable without having to redesign the insert or additional parts to break down or complicate the instrument, or reducing reliability.

The present invention together with the above and other advantages may best be understood from the following detailed description of the embodiments of the invention illustrated in the drawings.

BRIEF DESCRIPTION OF THE DRAWINGS

These and other aspects of the invention may be understood by reference to the following detailed description, taken in conjunction with the accompanying drawings, wherein:

FIG. 6A illustrates a cross-sectional view of the insert of FIG. 6 taken along the B-B line, showing the O-ring, the groove and a light source;

FIG. 6B is a partial cross-sectional view of the dental tool, handpiece and insert, showing an O-ring and the groove;

FIG. 7A is a partial cross-sectional view of the dental tool insert of FIG. 4A, including an external flow tube for delivering water to the tip in an alternative embodiment of the present invention;

FIGS. 7B, 7B1, 7B2, 7B3 and 7B4 each illustrates an internal flow channel in the tip of the dental tool insert of FIG. 2 in an alternative embodiment of the present invention;

FIGS. 7D1, 7D2, 7D3, 7D4, and 7D5 each illustrates the inclusion of a light source, a transducer and magnetic elements to a portion of the dental tool insert of FIG. 3A in an exemplary embodiment of the present invention;

FIG. 15E is a block diagram of an embodiment of an ultrasonic unit control system of the ultrasonic dental tool of the present invention;

FIG. 16 is a perspective view of an ultrasonic dental insert having a light source and a bobbin that includes a light transmitting material in an exemplary embodiment of the invention;

FIG. 16A is an exploded perspective view of the ultrasonic dental insert of FIG. 16;

FIGS. 34 and 34a show a top and side cross sectional views of a motor assembly, respectively, that includes a one-piece bobbin in one embodiment of the present invention.

FIGS. 35 and 35a depict the top and bottom isometric views of lens assembly in one embodiment of the present invention.

DETAILED DESCRIPTION

The detailed description set forth below is intended as a description of the presently exemplified embodiment in accordance with aspects of the present invention and is not intended to represent the only forms in which the present invention may be prepared or utilized. It is to be understood, however, that the same or equivalent functions and features may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein may be used in the practice or testing of the invention, the exemplified methods, devices and materials are now described.

It is desirable to provide a dental tool having an insert that is rotatable about a handpiece when the insert is disposed inside the handpiece. The rotation may be effected about a longitudinal axis of the insert by applying a force only to the insert.

Typically, during a dental procedure, the dental practitioner will need to repeatedly re-orient the location of the insert work tip with respect to the tooth surface. In making this re-orientation, the practitioner will typically take the insert out of the patient's mouth, rotate the insert inside the handpiece to re-orient the work tip and re-insert the insert in the patient's mouth. This is done because the insert is not easily rotatable inside the handpiece and the handpiece is tethered to a power and fluid supply source, so that rotation of the handpiece is limited.

A dental tool having a rotatable insert so that rotation may be effected single handed, for example, or a two finger rotation, is desirable. This is especially desirable if rotation may be effected by utilizing existing components without adding additional parts or complicating the construction of the dental instrument.

Figure 1:
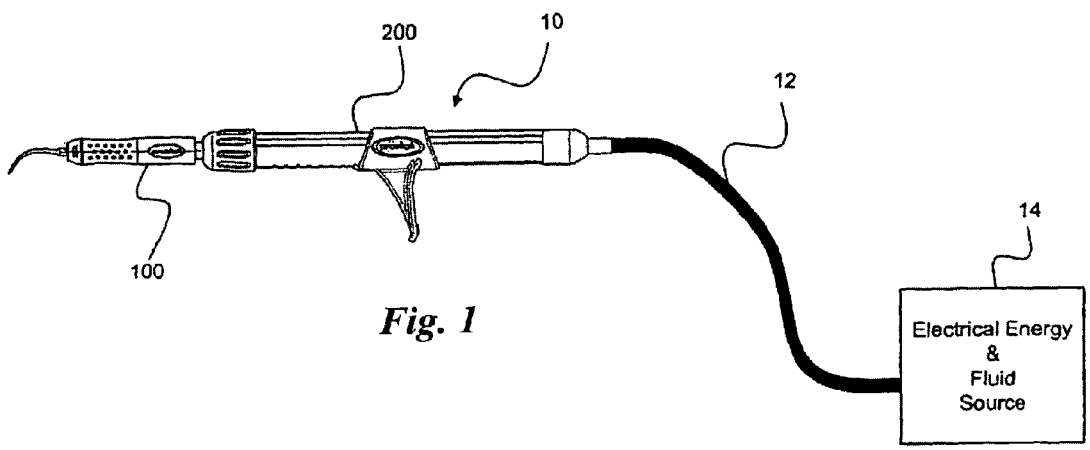
FIG. 1 or 1A illustrates an ultrasonic dental unit (or system) including an ultrasonic dental tool attached to an electrical energy & fluid source.
Figure 1A:
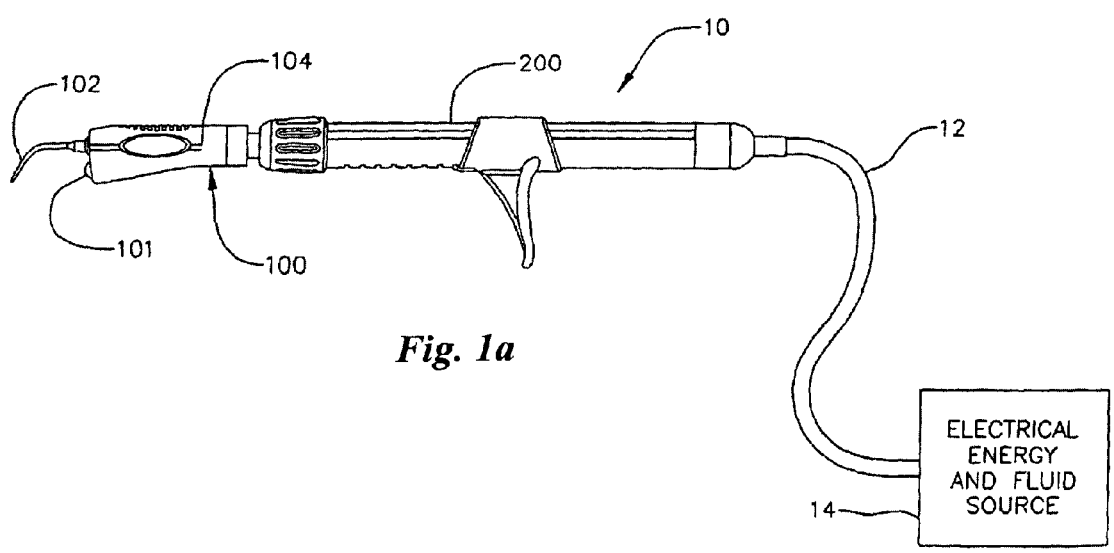

In exemplary embodiments of the present invention, FIGS. 1 and 1A each illustrates an ultrasonic dental unit including an ultrasonic dental tool 10 attached to an electrical energy & fluid source 14 via a cable 12 at its proximal end. The cable 12 includes a conduit for carrying fluid as well as wires for carrying electrical signals from the electrical energy & fluid source 14 to the ultrasonic dental tool 10. In FIGS. 2, 3, 3A, 6A and 7C exemplify some of the embodiments of exit points for the fluid to exit the insert 100.

The ultrasonic dental tool 10 includes a handpiece 200 and an insert 100 received within the handpiece 200. FIG. 1a also includes a built-in light source 101. The insert 100 includes a work tip 102 extending from its distal end. In other embodiments, no light source is present. In still other embodiments, an attachable light source may be used.

Figure 6:
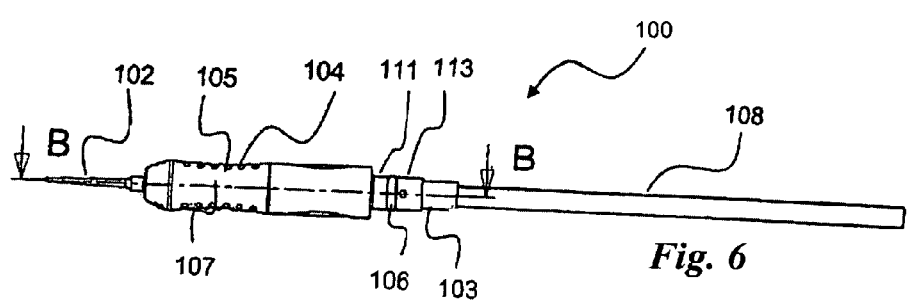
FIG. 6 illustrates the top view of the ultrasonic dental insert of FIG. 2, which has been rotated by approximately 90 degrees from the side view depicted in FIG. 3, showing the O-ring.

FIGS. 2, 2A, 3 and 3A each illustrates an ultrasonic dental insert 100 in an exemplary embodiment of the present invention. FIG. 6 is a top view of the dental insert 100, which has been rotated approximately 90 degrees from the side view depicted in FIG. 3. In these embodiments, the dental insert 100 includes a work tip 102 at its distal end and a motor, such as an ultrasonic transducer 108, at its proximal end. The work tip 102 may be coupled to the transducer 108 via a coupling member, such as a connecting body 103, which may, for example, take the form of a shaft. The connecting body 103 may be made of any material that is suitable for transmitting ultrasonic vibrations such as stainless steel or other metals and is used to deliver ultrasonic vibrations generated by the transducer 108 to the work tip 102 and for example, may be attached to the connecting body 103 by soldering, welding, laser welding and/or any other suitable method. For example, the joint between the connecting body 103 and the transducer 108 may be a brazed joint formed using a brazing compound, which may include cadmium free silver solder and high temperature brazing flux.

In some embodiments, the connecting body 103 is also used to generate voltage in an illumination energy coil 99, as discussed later with reference to, for example, FIG. 7C, or 7D3, surrounding at least a portion of the connecting body 103. In such instances, the connecting body 103 may be, for example, made of a material having magnetic permeability, and further for example, good magnetic permeability. By way of example, 17-4 PH stainless steel, and 420 stainless steel, while suitable for transmitting ultrasonic vibrations, are also mildly magnetic. Therefore, the connecting body 103 formed from 17-4 PH stainless steel may generate an ac voltage on the illumination energy coil 99 by moving rapidly (e.g., 25 kHz or faster) within the illumination energy coil 99 (not shown in FIGS. 2 and 3, but in FIG. 7C.)

The connecting body 103 may have mounted thereon a bobbin, or a ring, such as an annular retaining ring or collet 111, as shown in FIGS. 2, 2A, 3, 3A, 4A, 4C, 5, 6, 6A, 6B and 6C, which may also be made of a metal such as stainless steel.

The retaining ring 111 has a generally cylindrical shape and may have formed thereon a connecting portion 113, which defines also a generally cylindrical cavity therein for receiving a corresponding portion of the connecting body 103, in a force fit relationship, for example, or any other types of connections such as threaded connections, bayonet connections, and so on. The retaining ring 111 may be fixedly attached (e.g., snapped on as described below in reference to FIG. 5) to the connecting body 103 so that it does not substantially moves or rotates laterally along the axis of the connecting body 103.

Figure 6C:
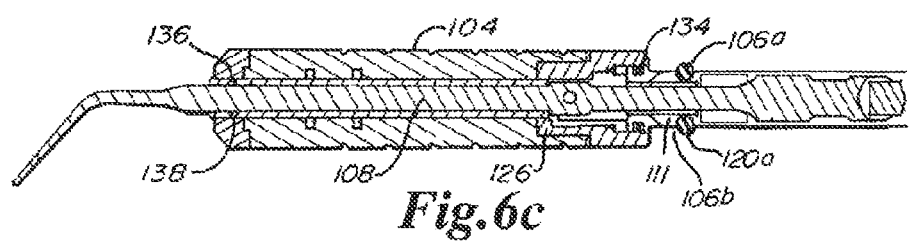
FIG. 6C is a partial cross-sectional view of the dental tool insert of FIG. 3, showing an O-ring and the groove.

Referring to FIG. 6A, 6B or 6C, the retaining ring or collet 111 may envelop a portion of the connecting body 103. At its distal end, the retaining ring 111 has formed thereon a pair of gripping elements 132 that face each other, as shown in FIG. 6A or 7C. Each gripping element 132 has an end portion that protrudes inwardly toward the end portion of the other gripping element 132. The connecting body 103 has a corresponding pair of indentations 139, as shown in FIG. 7C, formed thereon for receiving the protruding end portions of the gripping elements 132 such that the gripping elements 132 are snapped into the indentations 139. Thus engaged, the retaining ring 111 of the illustrated embodiment is locked to the connecting body 103, and neither rotates nor moves laterally with respect to the same. The retaining ring 111 has also formed thereon circular flanges 121, 124 and a circular groove 122. The circular groove 122 is for seating an O-ring 134, as shown in FIG. 6A or 7C.

Figure 4A:
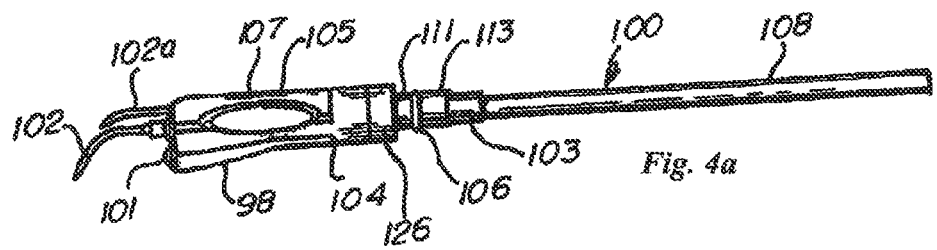
FIG. 4A is a side view of a dental tool insert having an external flow tube for delivering water to the tip in an alternative embodiment of the present invention.
Figure 4B:
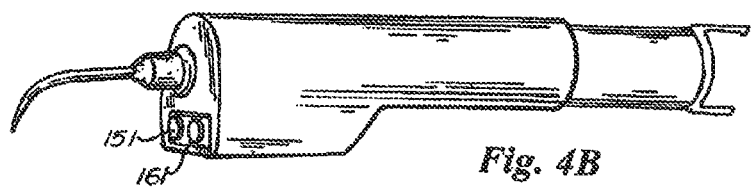
FIG. 4B illustrates the distal portion of a dental tool insert, having more than one LED and connectors.
Figure 4C:
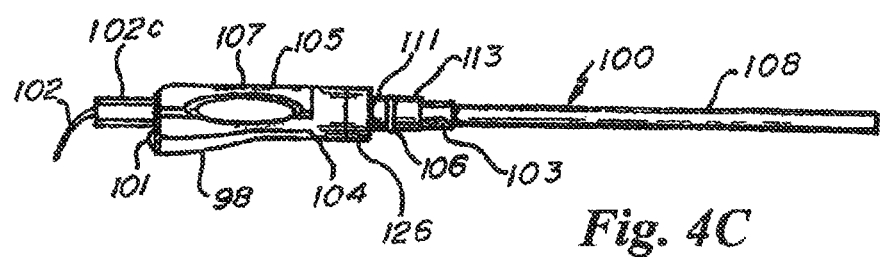
FIG. 4C illustrates a side view of a dental tool insert having a sleeve covering portions of the insert.
Figure 4D:
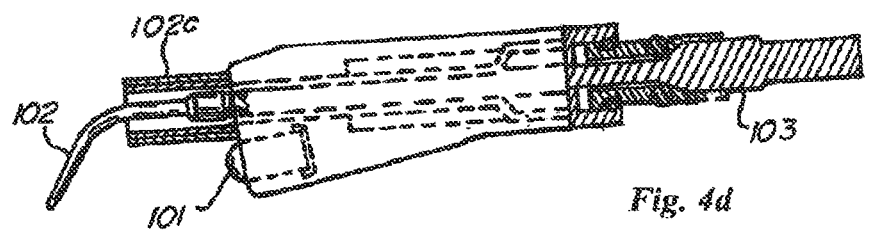
FIG. 4D is a cross-sectional view of FIG. 4C.
Figure 7:
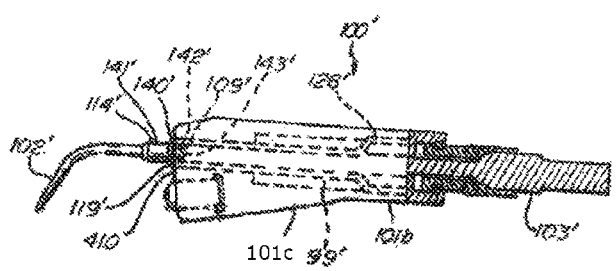
FIG. 7 is a partial cross-sectional view of the dental tool insert of FIG. 3A.
Figure 7C:
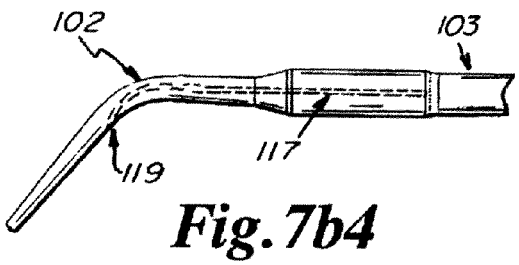
FIG. 7C is an exploded perspective view of the dental tool insert of FIG. 3A.
Figure 7C:
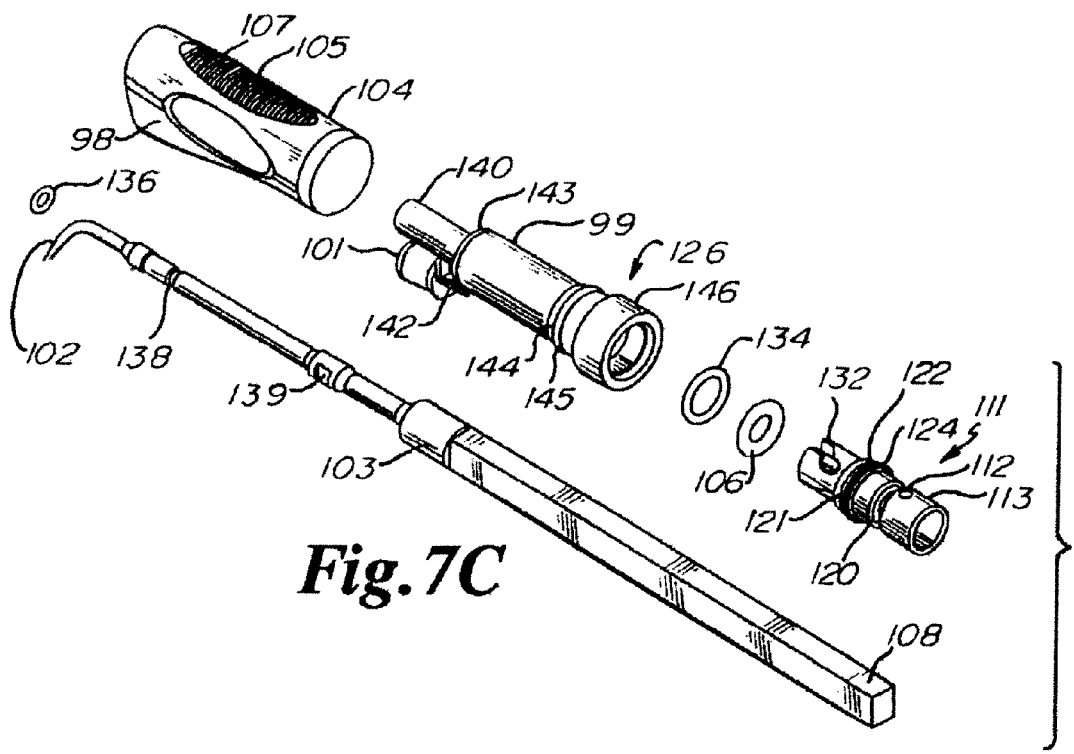

The retaining ring 111 may have an opening or two openings 112 formed thereon for receiving fluid from the handpiece 200, as shown in FIG. 7C. The opening 112 for receiving fluid may be formed on the side of the connecting portion 113. When two openings are present, they are formed on opposite sides of the connecting portion 113. The fluid may exit, for example, via any other mode, as shown in FIGS. 4A and 4C, discussed above and more below.

More details of the retaining ring may be found in U.S. Pat. No. 7,044,736, entitled "Ultrasonic Dental Insert Having A Hand Grip Fitted To A Retaining Ring", the content of which is hereby incorporated by reference.

In other embodiments, the retaining ring 111 may not be present and the groove may be present on the connecting body 103.

To seal the motor portion, for example, transducer 108, of the insert 100 and the handpiece 200 where water is circulated, so that water may lavage the motor 108 and keep it from overheating, as well as to keep the water from the work tip 102 except where desired, as discussed below, an O-ring 106 is generally used. The O-ring 106 generally sits in a groove 120 disposed somewhere on the connecting body 103 of the insert 100.

In one embodiment, the retaining ring 111 may have formed thereon, adjacent to the connecting portion 113, a circular groove 120 for seating the external O-ring 106, as exemplified in FIGS. 5, 6A, 6B and 6C.

When the insert 100 is disposed inside the hollow cavity 228 of the handpiece 200, the O-ring 106 may serve to retain the insert 100 within the handpiece 200 by, in one embodiment, gripping the inside wall of the handpiece 200 (cylinder), to be held securely inside the handpiece 200.

Typically, because of this sealing action of the O-ring 106, when the insert is inside the handpiece 200, rotation of the insert 100 inside the handpiece about the O-ring 106 is difficult, and generally requires both hands with some force. In the present invention, the O-ring 106 serves both to seal and to facilitate freer rotation of the insert 100 within the handpiece 200. More specifically, the rotation of the insert maybe effected between the O-ring and the rest of the insert.

The structure of the O-ring 106 is the same or substantially the same as that of a traditional O-ring, as is clearly shown in FIGS. 5, 6A, 6B and 6C. The O-ring 106 has an outer peripheral 106a and an inner peripheral 106b, as also shown in FIGS. 6B and 6C. The groove 120 on the retaining ring 111, as shown in FIG. 6B or 6C, includes a surface 120a that is in contact with one portion of the inner peripheral 106b of the O-ring 106. In one embodiment, the frictional force between the inner peripheral 106b of the O-ring 106 and the surface 120a of the groove 120 is relatively low to allow rotation of the insert 100 about the O-ring 106 with minimal resistance; while at the same time, the outer peripheral 106a of the O-ring 106 which is in contact with at least a portion of the inside of the handpiece 200 serves the sealing effect noted above.

The relatively low frictional force generated between the contacting surfaces may be due to the interaction of the materials used for these contacting surfaces, i.e., the two surfaces may include materials that have low or no adhesive interactions.

In one embodiment, the contacting surfaces may be constructed of low frictional materials. In one aspect, the exposed surface 120a of the groove 120 may be made of a material with a low coefficient of friction. In another aspect, the exposed surface 120a of the groove 120 may be coated with a low frictional material. In a further aspect, the inner peripheral 106b of the O-ring may be made of a material with a low coefficient of friction. In yet a further aspect, both the exposed surface 120a and the inner peripheral 106b of the O-ring 106 may be made of a low frictional material. In yet another aspect, both surfaces of contact, i.e. 106b and 120a, may be coated with a material having a relatively low frictional material.

When a coating is used, the coating of the exposed surfaces of the other areas of the retaining ring 111 may occasionally encountered wear problems for some coating materials, as this part of the insert has to endure harsh environments, for example, having constant water flow. At the same time, the coating on the surface 120a of the groove 120 is somewhat protected by the O-ring and may not encounter similar wear problems and thus, if a coating is performed on the surface 120a, more materials may be suitable for this coating. Thus, same, similar or different coating materials may be used for the different surfaces.

Examples of low frictional material may include polymeric or metallic materials. Polymeric materials may include nylon (condensation copolymers formed by reacting equal parts of a diamine and a dicarboxylic acid, examples of which includes nylon 6,6; nylon 5, 10; etc.), POM, (polyoxymethylene) HDPE (high density polyethylene), UHMW (Ultra high molecular weight high density polyethylene) fluoropolyethylenes such as PTFE (poly(tetrafluoroethene) or poly(tetrafluoroethylene), for example, Teflon® material and similar and a variety of polyxylylene polymers known as parylene. Metallic materials may include stainless steel, copper, titanium, magnesium, silver, zinc, a combination alloy thereof and similar low frictional materials. These materials may be coated onto the contacting surfaces 120a of the groove, the inner peripheral 106b of the O-ring 106, or both, if a coating is used. On the other hand, the contacting surfaces 120a or portions encompassing the inner peripheral 106b of the O-ring 106 may also be made of these low coefficient materials.

In another embodiment, the relatively low frictional surfaces of contact may also be made to have relatively smooth surfaces that may or may not be of relatively low frictional material. For example, by substantially eliminating irregularities on both surfaces of contact, on 106b and 120a, the coefficient of friction of the contacting surfaces may be reduced accordingly.

In yet another embodiment, a dual hardness O-ring 106 having a different hardness/material in the bulk or inner peripheral 106b of the O-ring 106 from that of the outside peripheral 106a of the O-ring 106 is contemplated. In one aspect, a higher hardness material in the bulk or the inner peripheral 106b may enable the contact surface of the O-ring 106 and the contact surface 120a of the groove 120 to have little or minimal adhesive interaction. Thus, instead of coefficient of friction, the property of the O-ring 106 may also be expressed in terms of its hardness and a lower hardness material on the outer peripheral 106a of the O-ring 106, may have a good sealing effect and better adhesion, while a higher hardness material on the inner peripheral 106b of the O-ring 106 may allow the insert 100 to rotate more freely inside the handpiece.

As noted above, the lower resistance, due to lower frictional interactions between the inner peripheral 106b of the O-ring 106 and the contact surface 120a of the groove 120 enables freer rotation of the insert 100 inside the handpiece 200 about the O-ring. In this embodiment, when the coefficient of friction on the outer peripheral 106a is high, there is sufficient axial friction between the insert 100 and the inside wall of the handpiece 200 to substantially prevent the insert 100 from popping out of the handpiece 200 due to water pressure within the handpiece 200 and/or drag by the handpiece cable.

Figure 6D:
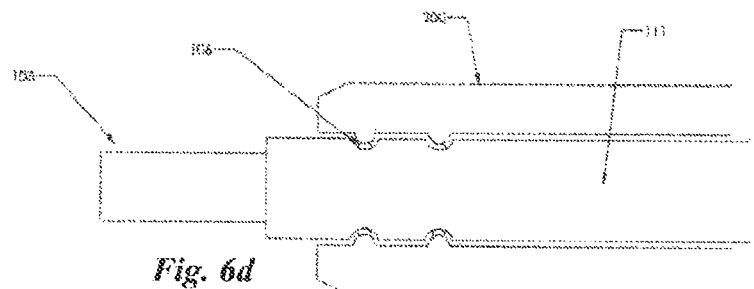
FIG. 6D is a partial cross-sectional view of the dental tool, showing another embodiment of the O-ring.

In another embodiment, the frictional force between the outer peripheral 106a of the O-ring 106 and the inside of the handpiece 200 and the frictional force between inner peripheral 106b of the O-ring 106 and the contact surface 120a of the groove 120 on the insert 100 may both be low, as long as the sealing action is not compromised. In this instance, the inside wall of the handpiece 200 may include a groove 120b, as shown in FIG. 6B, similar to the groove 120 in the insert 100, for seating the O-ring 106 and contacting its outer peripheral 106a. In this embodiment, the O-ring 106 may fit into the groove such that the insert 100 is not likely to pop out of the handpiece 200. In other instances, the O-ring 106 may have a notch or more about its outer peripheral 106a and the inside wall of the handpiece 200 may include a corresponding protrusion or more, so that the notch may mate with the protrusion to keep the insert 100 from popping out of the handpiece 200, as exemplified in FIG. 6D. The notch or protrusion maybe, for example, of low profile so that the insert 100 may still fit relatively snuggly in the handpiece 200. In other embodiments, more than one O-ring is used, as is also shown in FIG. 6D, and the insert 100 may be further stabilized inside the handpiece 200.

In a further embodiment, the coefficient of friction of the outer peripheral 106a of the O-ring 106 may be high even when a groove 120b or notch, as noted above, is present.

The groove 120b on the inside of the handpiece 200 may be of a high or low coefficient of friction as long as the sealing action it provides is not compromised.

Figure 11:
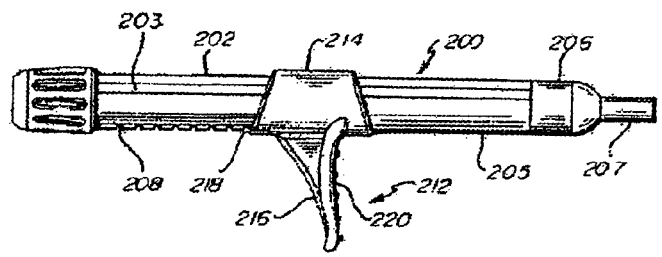
FIG. 11 is a side view of an ultrasonic dental handpiece that can be used with the ultrasonic dental insert of FIG. 2 to form an ultrasonic dental tool, having an optional handgrip.

FIG. 11 illustrates a side view of the handpiece 200, without an insert 100, that may receive the insert 100 as seen, for example, in FIG. 1. The interconnect 206 located at a proximal end of the handpiece 200 is coupled to a cable (e.g., the cable 12 of FIG. 1) for providing electrical energy as well as fluid (e.g., water) to the handpiece 200. The interconnect 206 may have a strain reliever 207 formed thereon to relieve strain between the interconnect 206 and the cable 12.

A handgrip 212 may optionally be present on the handpiece 200, as also exemplified in FIG. 11. The body 202 of the handpiece 200 has formed thereon a pair of grooves 203 that are substantially equidistant from the top and traverse substantially the whole length of the body 202. The grooves 203 may be used to mount the hand grip 212 on the handpiece 200. The body 202 may also have formed thereon at its bottom near the distal end of the body 202 a plurality of substantially evenly spaced slots 208 that may serve to lock the handgrip 212 to keep it from moving in the direction of the axis of the handpiece 200. The body 202 may also have formed thereon at its bottom near the proximal end a groove 205 that is co-linear to the slots 208. The groove 205 may engage the hand grip 212 together with the grooves 203 to keep the hand grip 212 from rotating about the central axis of the handpiece 200. In other embodiments, the grooves 203 or 205 may not be used.

The hand grip 212 has an engagement portion 214, which has a generally cylindrical shape and a hollow interior. The engagement portion 214 may be slipped onto the body 202 similar to a sleeve, and engages the body 202 such that the engagement portion envelops a portion of the body 202. The engagement portion may have formed thereon a resilient cantilever portion 218, which may be used to engage one of the slots 208 on the body 202. The engagement portion 214 may also have attached to its bottom surface a handle 216, which may be used by a dental practitioner to hold the handpiece 200 during dental procedures. The handle 216 may have formed on its back surface a plurality of indentations or protrusions 2200, which may be used to facilitate grasping by a dental practitioner. More detail of the handgrip may be found in U.S. publication no. U.S. 2005/0142515 A1, entitled "Dental Tool Having A Hand Grip", the content of which is hereby incorporated by reference.

The handpiece 200 may include at least one coil 238 which may be mounted on a bobbin 236 (shown in exploded form in FIG. 12) for providing the energy to the motor or transducer 108, which may include a stack of nickel plates such that the nickel plates 108 may vibrate at an ultrasonic frequency. The coil 238 receives energy from the electrical energy & fluid source 14 through the cable 12 as shown in FIG. 1 or 1A.

The insert 100 may also have a grip portion 104 towards its distal end, enveloping the connecting body 103, as shown in FIGS. 1, 1A, 2, 2A, 3, 3A, 4A, 4C, 4D, 5, 6, 6A, 6B, 6C and 7C. The grip 104 may be made of high temperature resin. For example, the hand grip 212 and the grip portion 104 may each be fabricated using thermoplastic elastomer such as SANTOPRENE® available from the Monsanto Company, a polyvinylchloride polymer, a polyurethane foam or elastomer, a polyamide, silicon, natural or synthetic rubber, for example, elastomeric materials and may include, but not limited to, various copolymers or block copolymers (Kratons®) available from Kraton Polymers and include styrene-butadiene rubber or styrene isoprene rubber, EPDM (ethylene propylene diene monomer) rubber, nitrile rubber (acrylonitrile butadiene), and the like, or those used in the construction of some work tips 102, discussed below, or any other suitable material that are moldable.

Also, additives may be added and/or blended into the aforementioned material to impart antimicrobial properties into the grip portion. Antimicrobial polymer additives may be categorized into two broad categories: organic or inorganic. These two categories have different attributes and may produce different desirable end-applications. While many antimicrobial additives are referred to as biocides, they have in fact two different effects: biocidal (killing of the organism) and biostatic (preventing reproduction). Organic additives are generally biostatic, and inorganic additives generally combine biocidal and bio static properties.

Inorganic antimicrobials generally utilize metal ions as their active biocidal agent, and once incorporated into a polymer matrix insitu, they remain with the matrix. The most commonly used metal ion is silver; others include copper and zinc. Silver ions are believed to disable bacterial cells by acting on them in several ways, and this multiplicity of action results in a strong biocidal effect. In the primary mode of attack, silver ions bind to the cell membrane, affecting its ability to regulate the diffusion and transport of molecules in and out of the cell. Similarly, once inside the cell, the ions target thiol groups on the proteins, which function as enzymes in their critical metabolic pathways. This denatures the enzymes, bringing about a loss of cell functional ability, and leads to cell death. Inorganic delivery systems on the market today may include those relying on ceramic glasses, doped titanium dioxides, and even zeolites as their carrier and release mechanisms. Inorganic systems tend to be much more thermally stable than organic ones. The thermal stability of the organic system means there is a wide range of polymers that can benefit from these additives.

For example, an inorganic ceramic crystal may be added to the polymer to impart the natural protection of silver into the polymer matrix, and thus the corresponding molded material prior to molding. In addition, non-metal-containing isothiazalone family of biocides, and other types, such as triclosan (chlorinated diphenyl ether), and Microban® may also provide antimicrobial protection.

Portions of or the entire handgrip may also be made of natural plant materials, natural material coating or blends thereof, that have inherent antimicrobial effects. Such materials include materials like bamboo, believes to possess antimicrobial activity due to some novel chitin-binding peptides.

In one embodiment, the grip portion 104 may be in one piece. In another embodiment, as shown in FIG. 2B, the grip portion 104 may be in multiple sections, for example, three sections, a proximal end section 104a and distal end section 104c of one material separated by a mid-section 104b of a different material. In one aspect, the three sections may only differ in color. In another aspect, the three sections may differ in hardness or softness. In yet another aspect, the three sections may differ in diameter or circumferential span. The sections may be co-molded or over-molded, or may be attached after forming. By way of example, a two-piece grip portion 104 may be over-molded or ultrasonically welded together over the illumination energy bobbin 126.

In one embodiment, the grip portion 104 may be formed through injection molding after mounting an illumination energy coil 99 (to be discussed further below) and the light source 101 on the connecting body 103.

In another embodiment, the grip portion 104 may be over-molded onto the connecting body 103, as shown in FIG. 6C.

The grip portion 104 may have a generally cylindrical shape in one embodiment, as shown in FIG. 2b, to be fitted over the illumination energy bobbin 126 and connecting body 103, for securing the light source 101 in place (e.g., through injection molding directly on the illumination energy bobbin 126), if present, as shown in FIG. 7c. The grip portion may also have a slightly protruding portion 98 on one side at the end of which the light source 101 (e.g., LED) is disposed, in one embodiment. In other embodiments, such as exemplified in FIG. 6B or 6C, there is no protruding portion 98 and the insert with a light source 101 is substantially of the same shape as one without a light source. In still other embodiments, the retaining ring 111 may not be used. Other embodiments of the grip portion 104 are also further described in detail below.

Figure 2:
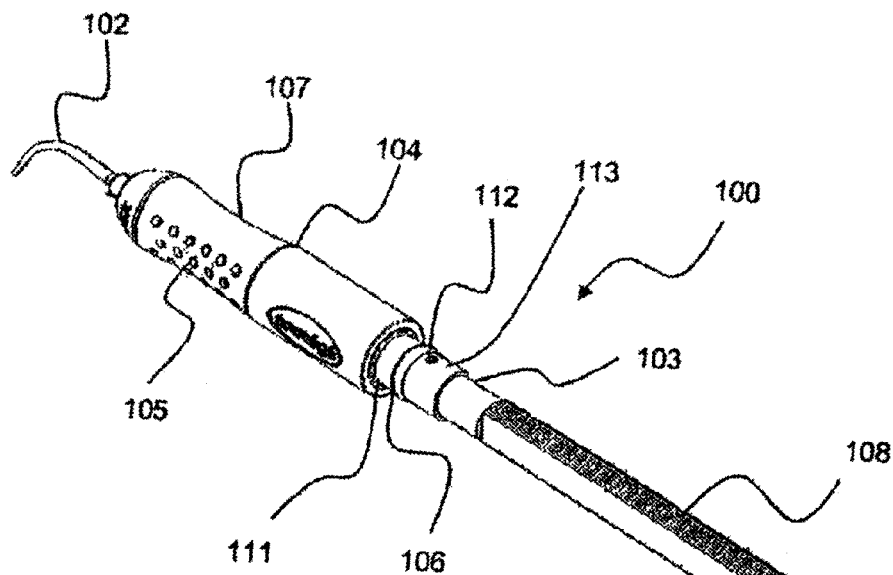
FIG. 2 is a perspective view of a dental tool insert in an exemplary embodiment of the present invention.
Figure 2B:
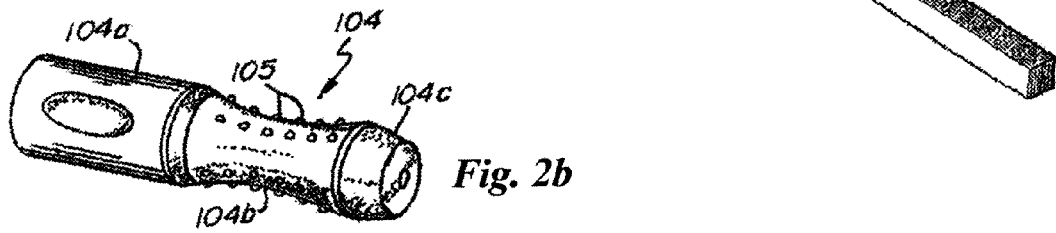
FIG. 2B shows an enlarge perspective view of a handgrip portion of the insert.
Figure 2A:
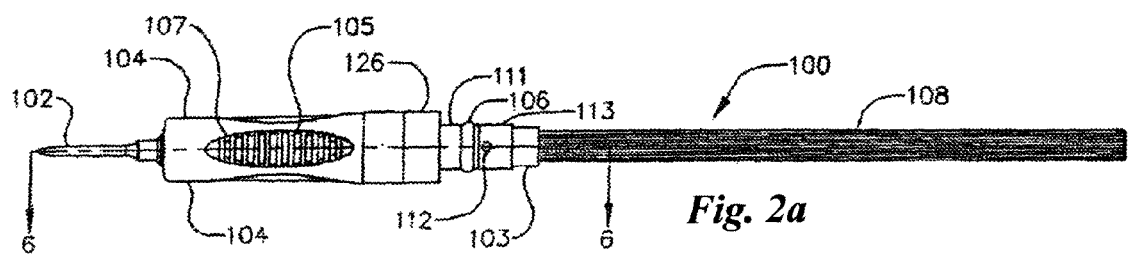
FIG. 2A is a top view of a dental tool insert in an exemplary embodiment of the present invention.

In one embodiment, along its outer surface, as shown in FIG. 2, 2A or 2B, the grip portion 104 has a contour and has a slightly concave area 107, enabling it to be easily grasped by a dental practitioner. The grip portion 104 may also have formed thereon a plurality of bumps 105 (i.e., rounded or striped protrusions as shown in FIGS. 2, 2A and 2B) on its external surface to further facilitate grasping of the device by a dental practitioner. Some may even be ergonomically designed.

In one embodiment, as shown in FIG. 6A, the retaining ring 111 also has formed thereon circular flanges 121, 124 and a circular groove 122. The circular groove 122 is for seating the O-ring 134, as discussed above. The grip portion 104 has an undercut 1260 formed therein for fitting over the distal end of the retaining ring 111, and engaging the flange 121. The undercut 1260, for example, is circular in shape.

The grip portion 104 has also formed thereon a depressed region 128 below the undercut 1260 on its inner surface, which is used to engage the flange 124 and further prevent the retaining ring 111 from moving into the grip portion 104. The depressed region 128, for example, is also circular in shape, wherein the depressed region 128 has a radius larger than that of the undercut 1260. The undercut 1260 and the depressed region 128 fit tightly with the flanges 121 and 124, respectively.

A tip O-ring 136 may also be present, as shown in FIG. 6C, and serves to seal the work tip 102 against the grip portion 104. This O-ring 136 may also be seated in a groove 138.

The work tip 102 may be permanently or removably attached to the connecting body 103. When removably attached, the tips 102 may be interchanged depending on the desired application. Further, the tip 102 may be disposed of, or steam autoclaved, or otherwise sterilized, after detaching it from the rest of the ultrasonic dental insert 100. For example, the tip 102 may be made using high temperature plastic such as a polyetherimide like ULTEM®; Polysulfone, Polyphenylene Sulfide, Polyarylate, Epoxy, phenolic, polyurethane, melamine, a polymeric alloy such as Xenoy® resin, which is a composite of polycarbonate and polybutyleneterephthalate or Lexan® plastic, which is a copolymer of polycarbonate and isophthalate terephthalate resorcinol resin (all available from GE Plastics), polycarbonate, acetal, polyetheretherketone (PEEK), liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, (exemplified in U.S. Pat. Nos. 6,242,063, 6,274,242, 6,643,552 and 6,797,198, the contents of which are incorporated herein by reference), polyesterimide anhydrides with terminal anhydride group or lateral anhydrides (exemplified in U.S. Pat. No. 6,730,377, the content of which is incorporated herein by reference) or combinations thereof. The term "plastic" is used herein to generally designate synthetic polymeric material, such as resin.

The work tip 102 may also be made of metal or metallic alloys such as stainless steel, which is particularly suitable when the work tip 102 is permanently attached to the insert 100. The attachment method may include any non-removable attachment such as soldering, welding, brazing, or the tip 102 may also be integrally formed as part of the connecting body 103.

Figure 12:
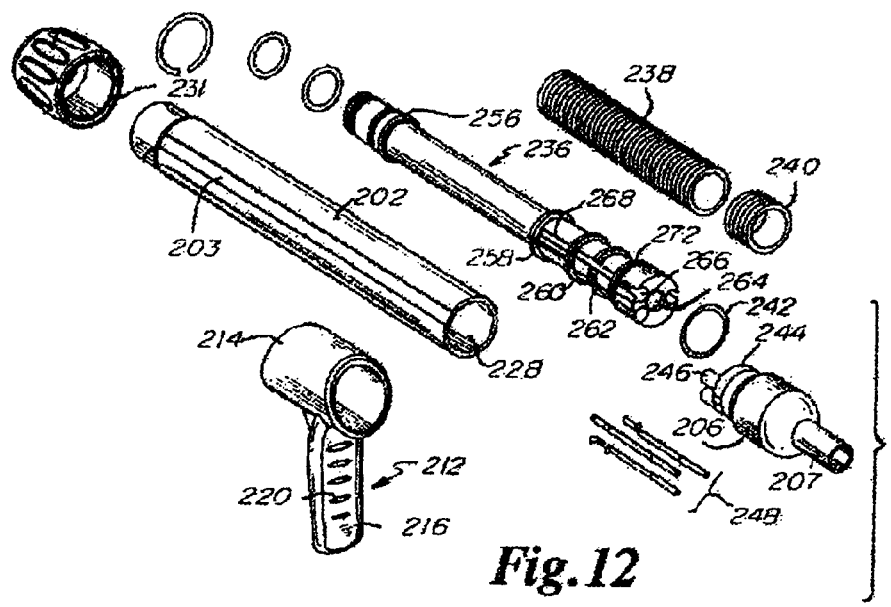
FIG. 12 is an exploded perspective view of the ultrasonic dental handpiece of FIG. 11, including an optional handgrip.

The body 202 of the handpiece 200 has an inner surface which defines a substantially hollow interior or cavity 228 formed therethrough, into which the bobbin 236 is received, as exemplified in FIG. 12. During a typical ultrasonic dental tool operation, fluid is pumped through the cable and the handpiece 200 to the tip 102 of the insert 100. Water is also circulated in the handpiece 200 to, for example, keep the motor or transducer 108 from overheating. The vibrating tip 102 of the insert 100 breaks the fluid stream into a spray. The spray not only keeps the tip 102 cool, but also keeps the surface of the tooth cool and provides protection against tissue damage. The fluid path through the handpiece 200 (through the bobbin 236) is sealed such that no leakage occurs until the fluid stream exits from the insert 100 at the distal end through a fluid delivery channel, for example, 117, as discussed below. In some embodiments, the hollow cavity 228 may have more than one compartment through which air and water may be delivered, respectively. In an exemplary embodiment, the compartments may be stacked one above the other. The air is delivered via the lower compartment and water is delivered via the upper compartment so that instead of a stream, the air/water mixture becomes a fine mist which can be gentler on the teeth.

The bobbin 236, if present, has also formed thereon a pair of substantially circular flanges 256 and 258. The long coil 238 may be mounted on the bobbin 236 between the flanges 256 and 258. The bobbin 236 has also formed thereon a pair of substantially circular flanges 260 and 262 near its proximal end. A short coil 240 is mounted on the bobbin 236 between the circular flanges 260 and 262. The coils, 238, 240, for example, are made from insulated wires. In other embodiments, the coils, 238, 240, may have substantially the same length, or the longer coil may be mounted near the proximal end of the bobbin 236.

Near its proximal end, the bobbin 236 has formed thereon a circular groove 272 for seating an O-ring 242. By seating the O-ring 242 in the groove 272, a water tight seal is formed between the bobbin 236 and the inner surface of the body 202 such that the fluid does not leak from the handpiece 200.

The bobbin 236 has an inner surface, which defines a generally cylindrical cavity for transmitting fluid from the proximal end to the distal end, and has an opening 264 at its proximal end for receiving fluid into the cylindrical cavity. The bobbin 236 has also formed at its proximal end a plurality (e.g., three) of openings 266, which are used to receive plug pins 248 in the bobbin 236. The plug pins 248 are made of electrically conductive material such as copper. The bobbin 236, the body 202, the hand grip 212 and the casing for the interconnect 206 are made of a suitable synthetic polymeric material, such as those mentioned above.

The bobbin 236 has also formed thereon a plurality of linear grooves 268 that are aligned with and extend from the respective openings 266 to the coils 238 and/or 240. The pins 248 installed, respectively, in the openings 266 and the grooves 268 are soldered and/or otherwise electrically connected to the coils 238 and/or 240, and are used to transmit electrical signals from the electrical energy & fluid and/or air source via the cable through the interconnect 206.

The interconnect 206 has also formed thereon a plurality (e.g., three) of elongated sockets 246 that engage the openings 266, respectively. The elongated sockets 246, for example, are formed on a connector portion 244 of the interconnect 206. The elongated sockets 246 have formed therein electrical contacts for making electrical connections with the plug pins 248, respectively. The electrical contacts are electrically connected at the other end with the wires in the cable 12, for example, to supply electrical energy to the coils 238 and 240, thereby energizing them.

Referring now to FIG. 7B, the tip has an elongated tapered portion 115, and a cylindrical interface portion 1140 ("base"). The interface portion 1140 may be adapted for removably connecting or disconnecting the tip 102 to the insert 100, as discussed below. It can be seen in FIG. 7B that the tapered portion 115 is curved to a certain degree. The tapered portion 115 has a circular cross section whose diameter decreases gradually from the end abutting the interface portion 1140 ("the proximal end") to the other end of the tip ("the distal end"). The distal end is applied to the gum/teeth of the patient during the dental procedures. The degree of curve of the tapered portion 115 is chosen to better facilitate the functioning of the tip 102 on the tooth during operation of the dental tool 10 in a dental procedure.

In one embodiment, the curve in the tapered portion 115 may be towards the light source 101, i.e., towards the right side of the insert 100, if one is present. In another embodiment, the curve in the tapered portion 115 may be away from the light source 101, i.e., towards the left side of the insert 100.

In another embodiment, as exemplified in FIG. 7A, the insert 100 may include an external flow tube or pipe 102a, for example, in the form of a separate tube or pipe, for delivering water to the tip 102. The tube 102a may be disposed in such a way as to reduce spattering and produce an adhering coat of fluid on the tip 102. The external flow tube 102a may be supplied with water via an internal flow channel 102b, which interfaces with the fluid chamber inside the insert 100.

In other embodiments, the tip 102 may have an opening towards the distal end for enabling fluid to exit the insert 100, an example of this is shown in FIG. 4A or 7B. In this embodiment, the tip 102 may have a small passageway 117 therethrough for supplying water or other fluid to the region in the mouth being operated on.

In other embodiments, a fluid passageway 117 may be internal of the tip 102, as exemplified in FIG. 4, 4A or 7B. In this embodiment, the tip 102 may have a small passageway 117 therethrough for supplying water or other fluid to the region in the mouth being operated on. The exit or orifice, for example, 119, maybe situated at different portions of the tip 102, depending on the type or function of the tip 102.

In FIG. 7B, the insert tip 102 may utilize an internal flow channel 117, such as a small lumen or passage way 117 through a substantial length of its interior, which receives water from the internal fluid chamber within the insert 100 about the interface portion 1140 and exits the tip 102 at the aperture 119 to deliver it to the working area.

The aperture 119 may be eccentrically offset from the center axis of the tip 102 such that the passageway 117 is substantially parallel to the center axis of the tip 102 but displaced from said axis towards the distal end. In other examples, the insert 100 may have an opening at the end of its tip 102 which may have a small passage way 117 extending throughout the entire length such that water or any other liquid may exit the tip 102 at its distal point, depending on the type or function of the tip 102.

In one aspect, the passageway 117 may be formed generally along the longitudinal axis of the tip 102 and may be offset such that a fluid discharge orifice 119 may be formed displaced away from the tip 102, such as exemplified in FIG. 7B1 or 7B2. The aperture or orifice 119 may be eccentrically offset from the center axis of the tip 102 such that the passageway 117 is substantially parallel to the center axis of the tip 102 but displaced from said axis towards the distal end.

In one example, a fluid passageway 117 maybe bored through the body of the tip 102, with an angular offset from the longitudinal center axis of the tip body 102 such that fluid discharge orifice 119 is formed in a side wall of the tip body 102, located a selected distance from the distal end of the tip 102, as shown in FIG. 7B1.

According to FIG. 7B1, the internal fluid passageway 117 may emerge from the shaped tip 102 as a fluid discharge orifice 119 at or very near the first node of vibration, if misting desired. At 25 kHz and 30 kHz, the FIG. 7B1 tip design may have its first node at from about 4 to 5 mm from the tip 102. The second loop, after the loop at the tip end, occurs between 7 and 9 mm from the tip end, where the flexural motion is still great enough to cause complete misting of the fluid flowing towards the tip 102. If misting is not desired, the orifice 119 may break out of the tip wall between about 5.5 and 6.5 mm from the tip end. The supply of fluid emerging from the discharge orifice 102f may exit at a point adjacent to a vibrational node of relatively low motion, which may minimize or will not cause spray and mist formation. The exact location of the fluid discharge orifice 119 and, hence, the angle offset employed in boring the passageway 117 may be determined by the ultimate final shape of the tip and the flexural motion desired.

While spraying occurs, the spray is at the work surface and will properly flush and cool the surface of the tooth.

The fluid passageway 117 maybe formed in the tip body 102 by means of a number of techniques including drilling and boring. A boring method maybe of electric discharge machining, a method of removing metal material using a series of rapidly recurring electric arcing discharges between an electrode (the cutting tool) and a work piece. The EDM cutting tool is guided along a cutting path very close to but, not touching, the work piece. Consecutive sparks produce a series of micro-craters in the work piece by melting and vaporizing the workpiece material. The resulting particles are washed away by a continuous flow of dielectric fluid. Utilizing this method may ensure that there is no bending of the hole being drilled, and that the passageway 117 maybe angled to break out on a wall surface of the tip 102, as shown in FIG. 7B1, on the convex side of the existing or intended bend, 5 to 8 mm from the end of the tip 102, as discussed below in relation to FIG. 7B1 or B2. Typically, after forming the passageway 117, the tip 102 is machined, formed or bent to its useful finished shape and configuration. This is discussed more below.

Alternatively, the passageway 117 may be bored into the tip body or cylinder using a lathe that is equipped with a tail stock that can be offset. The offset is adjusted, for example, sufficiently to produce an angle of 1 to 1.6 degrees from the centerline of the tip body cylinder 102. This is equivalent to an offset distance of 0.4 to 0.6 mm at the end of the cylinder 102. The passageway 117 is drilled and the offset tailstock of the lathe is returned to its centering position, aligned with the live or driven center of the lathe. The blank is then machined, for example, to provide tapering, to its final design dimensions. The result is a tip blank that has its internal fluid passageway 117 centered at the large end of the blank and exiting at a cylindrical wall displaced from but near the small end of the tip 102. This process produces a blank that is of uniform cross-section, tapering near the end of the tip 102, where vibrational stresses are greatest and maximum material within the design parameter is needed for strength. Maximum strength may be achieved by this method because the machine tip blank 102 may remain concentric to its maximum strength orientation formed along its longitudinal axis during drawing. The resulting tip 102 has a fluid outlet 119 located 2 to 8 mm from the end of the tip 102.

To produce the passageway 117 exemplified in FIG. 7B1, as another example, if the tip 102 is separate from the connecting body 103, the passageway 117 maybe bore using any suitable boring tool, from the connecting end of the tip 102 to the connecting body 103 prior to connecting to the connecting body 103. The tip 102 may then be bent to any configuration, but typically to an arc of about 60-70 degrees, and typically made after the passageway 117 has been bored, as shown in FIG. 7B2.

In another example, if the tip 102 is connected to the connecting boy, an electric discharge (EDM) method may be used to create the passageway, as shown in FIGS. 7B3 and B4. In this example, a short "cross hole" 102*f*, as shown in FIG. 7B3 is first made in the connecting body 103. The cross hole allows fluid supplying to the inside of the handpiece 200 to feed into the passageway 117. The tip 102 is also first bent to a 'Contrabend Geometry' as shown in FIG. 7B3. The long passage 117 is substantially parallel to the axis of the connecting body 103 and substantially coincident with the central axis of the connecting body 103. The passageway 117 maybe then cleaned and/or deburred. At the completion of the process, the tip 102 is then bent to a 'Final Bend Geometry' as shown in FIG. 7B4.

In all the examples, care is undertaken to insure that the bend does not restrict the flow of fluid through the tip 102. The exact shape of the tip may be determined by the work piece surfaces upon which the tool is to be utilized.

In another aspect, the tip 102 may have an opening at the distal end for enabling fluid to exit the insert 100, an example of this is shown in FIG. 4D. In this embodiment, the tip 102 may have a small passageway 117 therethrough for supplying water or other fluid to the region in the mouth being operated on.

In a further aspect, the passageway 117 may be formed generally along the longitudinal center axis of the tip 102, but without bending the tip 102 prior to the drilling or EDM process, as shown in FIG. 7B1, except that the axis of the passageway 117 makes a substantially right-angled turn towards the exit point or orifice 119 in the wall of the tip 102 instead of angling along the length of the passageway.

In yet a further aspect, a tube internal of the tip 102 may be used to carry the fluid towards the bent portion of the tip, as shown in FIG. 4A. The tube maybe inserted through the passageway 117.

In yet another aspect, the tube internal of the tip 102 may exit in an area of the tip 102 where there is a groove in the tip so that the tube may rest in the groove (not shown) for a distance and thus is barely visible. In this embodiment, the flow tube 102*a* as shown in FIG. 7A may be situated closer to the tip portion 102 for it to rest in a groove of the tip portion 102.

In yet another embodiment, as exemplified in FIG. 4C, a sleeve 102C may substantially surround a portion of the connecting body 103 of the insert 100. The connecting body 103 includes an elongated region of reduced diameter proximal to the tip 102, and the sleeve 102C, may be positioned around and substantially filling the reduced diameter region of the connecting body 103, and covering at least portions of the tip 102, may be fitted over the tip 102 in such a manner that a small channel exits for water to pass through and guide towards the tip 102.

The sleeve 102C, may be in the form of, for example, an elongated elastomeric tube portion, and may also act to dampen noise generated by operation of the insert 100. The elastomeric material may include an acrylic acid/acrylic ester copolymer such as iso-octylacrylate, having good vibration damping properties, or any of the materials described below for the handgrip 104. Some of these materials are also described in U.S. Pat. No. 5,118,562, the content of which is hereby incorporated by reference.

Further, an opening for applying the fluid to the mouth may instead be formed on the bobbin 126, as noted above, or the grip portion 104.

The tip 102 may be in the form of a scaler, an endodontic dental file, a dental drill, or those useful for other periodontal treatments. Some of them can also have a capability of delivering fluid and/or air.

The tip 102 may be formed as a single integrated piece with the connecting body 103. In other embodiments, the tip 102 may have attached to the interface portion 1140, a threaded portion for engaging a threaded opening formed on the connecting body 103. This is illustrated in FIG. 7B.

What is being described for FIG. 7B also applies to the embodiment where the tip 102' is integral with the connection body 103', as shown in FIG. 7. Using such threaded engagement 119', the tip 102' may be made removable. Such removability may allow the tip to be a disposable tip 102' that is replaced after a single patient use. In still other embodiments, the removable tips may also be pressure fit into a corresponding opening on the connecting body 103'.

The replaceable tip 102', as shown in FIG. 7 may be made of metal (e.g., stainless steel) or plastic (e.g., ULTEM®), as noted above. Since the tip 102' has a very small diameter, it may be subject to breakage if too much ultrasonic vibrations are applied to it. On the other hand, if insufficient vibrations are applied, the ultrasonic dental tool may not work effectively. Therefore, the connecting body 103' and the tip 102' may be designed such that a proper level of vibration is applied to the tip. Since a plastic tip is more likely to break than the metal tip, a shock absorbing mechanism may be used on the connecting body 103' to reduce the shock to the plastic tip 102', such as the elastomeric sleeve 102c described above in relationship to FIG. 4C, or the O-rings 140' and 142', to be described below.

In one embodiment, the connecting body 103' has formed thereon the threaded tap 119' for screwing in the tip 102', as is shown in FIG. 7. The word "tap" will refer hereinafter to a threaded opening formed at the distal end of the connecting body 103' for engaging the threaded portion 109'. The threaded portion 109' engages a corresponding thread on the inner surface of the threaded tap 119' such that the tip 102' is received by the connecting body 103'.

The connecting body 103' has formed surrounding the threaded tap 119' a pair of grooves 141' and 143' for seating O-rings 140' and 142', respectively. The O-rings absorb shock such that the vibrations "felt" by the tip 102 are reduced (i.e., dampened), thereby reducing the chance of breaking the plastic tip 102. In other embodiments, the connecting body may have only one or two or more O-rings mounted thereon for such shock absorption purposes. In still other embodiments, the threaded portion 109' may have a diameter that is substantially the same as the diameter of the interface portion 114', and the diameter of the threaded tap portion 119' may be correspondingly larger to receive the threaded portion 109'.

The transducer 108, as shown in FIGS. 2 and 2A may, for example, include a stack of thin nickel plates arranged in parallel with respect to one another. Since the transducer 108 generates ultrasonic vibrations in the dental tool, the transducer 108 may also be referred to as a motor. In one embodiment the thin nickel plates may include 16 laminated nickel alloy strips, which are 90% nickel manganese (NiMn). The nickel plates may be joined together at both ends at a brazed joint using, for example, a brazing compound including cadmium free silver solder and high temperature brazing flux. The illustrated insert 100 is a magnetostrictive type insert 100 in which the nickel plates 108 can vibrate ultrasonically when a coil (e.g., coil 238, as shown in FIG. 12) in the handpiece 200 is energized using the electrical signals from the cable 12.

During operation, the stack of thin nickel plates 108, for example, vibrates at a frequency equal to the stack's natural frequency responsive to excitation induced by coils 268 of the handpiece 200. After the insert 100 is placed in the handpiece 200 and the electrical energy source 14 is powered on, the operator may manually tune the frequency of the electrical energy source until it reaches the resonance frequency, i.e., the natural frequency of the insert. Alternatively, auto-tune units may automatically lock on the insert resonance frequency once powered on. At this time, the stack begins vibrating. This vibration of the stack is amplified and transmitted to the tip 102 through the connecting body 103. Any means of amplification are contemplated. Ultrasonic inserts 100 may vibrate at frequencies of from about 20 KHz to about 50 KHz in general, and those used in the United States are typically designed to vibrate at frequencies of about 25 kHz or about 30 kHz. In response to the ultrasonic vibration of the stack of thin nickel plates 108, the tip 102 and the connecting body 103 vibrates (e.g., rapid back and forth motion in the direction of the axis of the connecting body 103). By way of example, the motion in the direction of the axis may be between about 0.00125 centimeter (cm) to about 0.00375 cm depending on such factors as the vibration frequency, material used for the connecting body 103, the length of the connecting body 103, and the like.

In one embodiment, the light source 101 is energized by the already available ultrasonic vibrational energy such that an additional source of energy is not needed. By way of example, a transducer 108, such as and/or including, an illumination energy coil 238, is provided and attached to the light source 101 such that the light source 101 is energized using vibrational energy converted by the transducer 108. By way of example, a first transducer 108 is used to generate ultrasonic vibrations. This causes the connecting body 103 to move rapidly to generate an electromagnetic field during operation of the insert 100. As the connecting body 103 of the dental insert 100 moves, an alternating current (ac) voltage is generated in the illumination energy coil 238, which is connected in series with the light source 101 (e.g., light emitting diode (LED)) to provide energy for light emission. In other embodiments, any other suitable transducer for converting vibrational energy to energy for light emission may be used. The word "light source" as used herein may include one or more than one light source(s).

Figure 13:
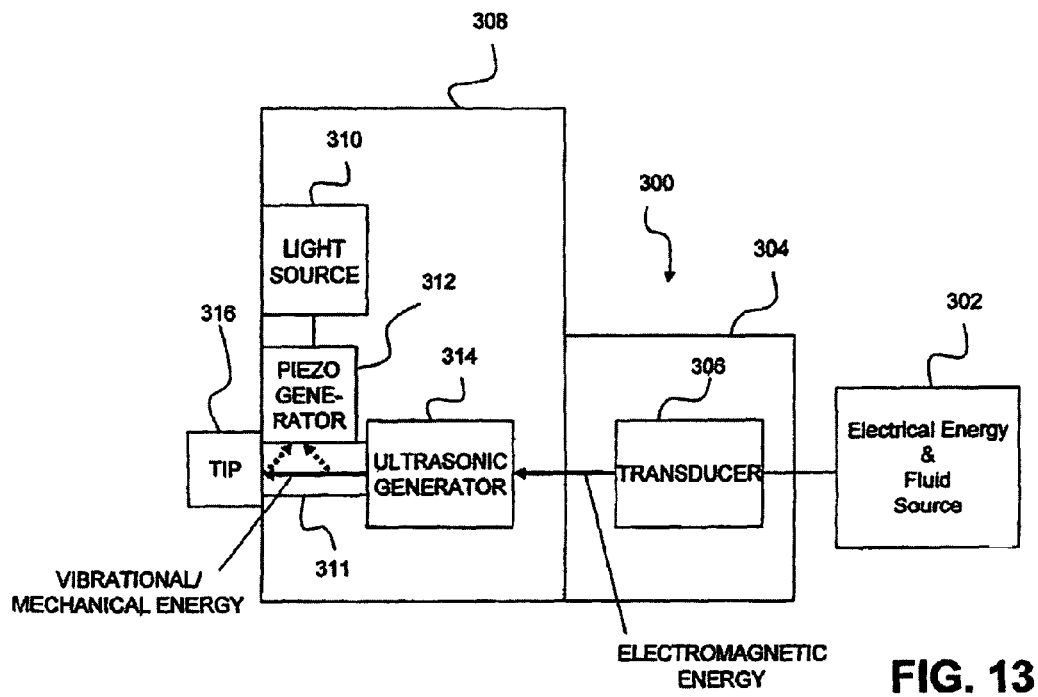
FIG. 13 is a block diagram of another example of an ultrasonic dental unit (or system) including a piezoelectric generator.

In other embodiments, the ultrasonic dental insert 308 may use a piezoelectric transducer 306, as is common in Europe, as exemplified in FIG. 13. A piezoelectric transducer may also generate ultrasonic vibrations for a dental tool 300. During operation of such a dental tool 300, an electrical signal of an appropriate frequency is applied to a piezoelectric crystal. This electrical signal impresses a voltage across the crystal. In response to this voltage, the crystal expands and/or contracts and the expansion and/or contraction may be used to drive a tool tip 316.

As is known by one of skill in the art, the piezoelectric effect is reversible. Applying an appropriate stress to a piezoelectric crystal may cause a voltage to appear across the crystal. This voltage, in turn, may be used to drive an electric current through an electrical load, such as a light emitting diode. Accordingly, in one embodiment of the invention shown in FIG. 13, a piezoelectric generator 312 is mechanically coupled to a connecting body 311 adapted to support a tool tip 316 of a dental tool 300.

In FIG. 13, the dental tool 300 includes a handpiece 304 and a dental insert 308. The handpiece 304 includes a transducer 306, which may be or includes a coil for energizing an ultrasonic generator 314 in the ultrasonic dental insert 308. The handpiece 304 receives electrical energy and fluid and/or gas (e.g., water) from an electrical energy, fluid and/or gas source 302. The handpiece 300, by way of example, may be substantially the same as the handpiece 200 of FIGS. 11 and 12. The dental insert 308 includes a light source 310 coupled to the piezoelectric generator 312. The electrical energy source 302 supplies an electrical signal to the transducer 306. The transducer 306 receives the electrical signal and generates an alternating magnetic field.

In operation, the ultrasonic generator 314 is disposed within the magnetic field and vibrates in response to the alternation of the magnetic field, as noted above. The vibrations of the ultrasonic generator 314 are mechanically coupled to the tip 316 and to the piezoelectric generator 312. The piezoelectric generator 312 generates an electrical current which is received by the light source 310. The light source 310 may be integrated with the dental insert 308, and may include two or more light sources, similar to that discussed before.

In one aspect, the piezoelectric member 312 may be disposed anywhere it may readily access the mechanical or vibrational energy of the first transducer 314. In one embodiment, the piezoelectric member 312 may be disposed proximate to the connecting body 311. In another embodiment, the piezoelectric member 312 may be disposed proximate to the first transducer 314. In yet another embodiment, the piezoelectric member 312 may be combined with the first transducer 314. In one aspect, a piezoelectric member 312 may be used in place of one of the nickel plates in the first transducer 314. In another aspect, a piezoelectric member 312 may surround at least a portion of the first transducer 314, for example, as a coating on at least a portion of the first transducer 314.

The piezoelectric generator 312 may include a piezoelectric body such as a quartz crystal, a Rochelle salt crystal, a lead-zirconate-titanate (PZT) ceramic, polymers including polyvinylidene difluoride (PVDF), or similar. Vibration of the tool tip 316 and/or a connecting body 311 induces an electrical voltage across the piezoelectric body. The electrical voltage drives a current through the light source 310, such as a light emitting diode, supported on the dental insert 308 of the dental tool 300. According to one aspect of the invention, light from the light source 310 may be used to illuminate a work region near the tip 316 of the dental tool 300, as shown in FIG. 13.

Figure 14:
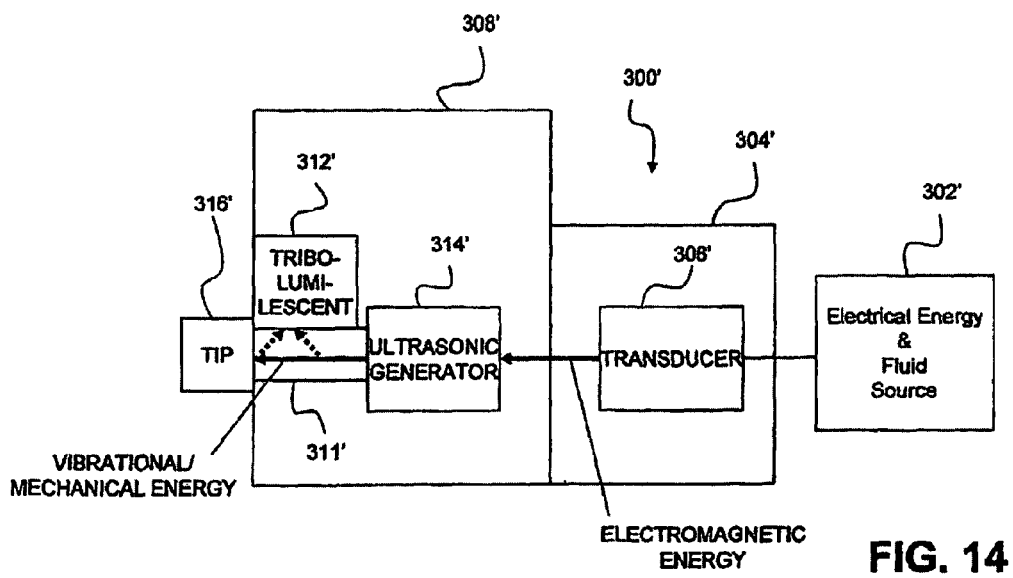
FIG. 14 is a block diagram of another ultrasonic dental unit (or system) including a triboluminescent material.

FIG. 14 illustrates a dental tool 300' having a handpiece 304' and a dental insert 308'. The dental tool 300' is coupled to an electrical energy, fluid and/or gas source 302', and operates in a similar manner as the dental tool 300 of FIG. 13, discussed above, except that the dental tool insert 308' includes a triboluminescent material 312' located near a tip 316' for providing illumination of the work region. A separate light source may not be needed as the triboluminescent material 312' emits light when stressed/deformed, e.g., by the vibrational energy generated by an ultrasonic generator 314' and transmitted via a connecting body 311'. The energy for the ultrasonic generator 314' is provided by a transducer 306' in the handpiece 304'.

Surprisingly, it is found that when the connecting body 103, or 103' or portions of the insert 100 is effectively magnetized, the output of the light source such as an LED 101 is sufficiently bright to be used on a workpiece, particularly when the energy for powering the light source 101 comes from the vibrational energy. In one embodiment, when such mildly magnetic material is used for the connecting body 103, or 103', a magnetic source, such as a permanent magnet, a rare-earth magnet, or a magnetic field, may be used to initiate and/or also to re-establish proper magnetization of the metal connecting body 103 or 103' after autoclaving or exposure to unsuitable environment such as shock. When this re-magnetizing is done, the brightness of the light source, such as the LED 101, is increased by more than, for example, about 50% over that of a non-magnetized connecting body, or even over that of a mildly magnetized connecting body. The magnetic source 410 may be placed in close proximity to the connecting body 103 or the insert 100. For example, the magnetic source 410 may be embedded in the housing of the insert, as shown in FIG. 7. In another exemplary embodiment, the magnetic source 410 may be removably coupled to the connecting body 103'.

In a further exemplary embodiment, at least a portion of the connecting body 103, or 103' and/or insert 100 may include a magnetic material or source 410, such as a permanent magnet, or a rare-earth magnet. A rare-earth metal, such as Neodymium-Boron, or Samarium-Cobalt, may be formed one at least a portion of the connecting body 103 or 103' towards the tip 102.

According to one embodiment, a ring-shaped holder 147 may be used to hold the magnetic source. In one embodiment, the ring-shaped holder 147 may be integrally formed on the bobbin 126, as exemplified in FIGS. 7D1 and D2. In one embodiment, the magnetic source 410 may be of arcuate shape. The arcuate shape may be of a small arc. In another embodiment, the magnetic source 149 may be of a rectangular block, as exemplified in FIGS. 7D1 and 7D2. The thicknesses and lengths of the blocks may vary. A thinner and longer block may reduce the protrusion of the magnetic source material 149, and thus the protrusion on the handgrip may be reduced, while at the same time, a thicker and shorter block may aid in space management of the insert in other respects.

In addition, one of skill in the art would recognize that the shapes and locations of the magnetic materials or sources shown in FIG. 7 is merely exemplary, and that many alternative locations would also fall within the invention scope, as long as the magnetic material or source is close to the tip 102 or 102', or other parts of the connecting body 103'.

In one embodiment, the magnetic material or source 149 may be placed inside an appropriate holder, as exemplified in FIG. 7D1, 7D2, 7D3, 7D4 or 7D5 (to be further discussed below), to magnetize or to re-magnetize the insert 100 or 100' and tip 102 to allow the connecting body 103 or 103' to generate an electromagnetic field during operation of the insert 100 to power an attached light source 101 such as an LED. The holder may be in close proximity to the coil 99' inside the grip portion 104, such as shown in FIG. 7, to be used to generate the electromagnetic field that generates power to light the LED 101 connected to the insert 100. The presence of this magnetic material or source 410 may allow the connecting body 103 or 103' to retain its magnetic properties in an optimal manner even after exposure to heat or physical shock.

In another embodiment, the magnetic material or source 410, may be placed inside the grip portion 104, as shown in FIG. 7C, of the insert 100, and thus is in close proximity to the coil 99 inside the grip portion 104 that is used to generate the electromagnetic field, with one pole, for example, the north pole, of the magnetic source oriented in such a manner as to maximize that effect. This allows the connecting body 103 to retain its magnetic properties in an optimal manner even after exposure to heat or physical shock.

As noted, the connecting body 103 is used to transfer ultrasonic energy from an attached ultrasonic transducer 108 to the tip 102 of the connecting body 103, which may or may not be a detachable piece of the connecting body 103.

In the present invention, the magnetic materials or sources such as permanent magnets and rare earth magnets may be used. Iron, nickel, cobalt and some of the rare earths (gadolinium, dysprosium) exhibit a unique magnetic behavior which is called ferromagnetism because iron (ferric) is the most common and most dramatic example. Samarium and neodymium in alloys with cobalt or boron have also been used to fabricate very strong rare-earth magnets.

Ferromagnetic materials exhibit a long range ordering phenomenon at the atomic level which causes the unpaired electron spins to line up parallel with each other in a region called a domain. Within the domain, the magnetic field is intense, but in a bulk sample, the material may usually be unmagnetized because the many domains may themselves be randomly oriented with respect to one another. Ferromagnetism manifests itself in the fact that a small externally imposed magnetic field, say from a solenoid, may cause the magnetic domains to line up with each other and the material is said to be magnetized. The driving magnetic field is then increased by a large factor which is usually expressed as a relative permeability for the material.

Without wishing to be bound by a theory, it is surmised that some magnetic materials, for example those having low susceptibility or permeability (low tendency to become magnetized), low hysteresis, (low tendency to "remember their magnetic history"), or low remanence (the fraction of the saturation magnetization which is retained when the driving field is removed), may lose what little magnetic properties they have due to autoclaving, repeated cycling, and/or physical shock. This loss may also lead to loss in the ability of the device to convert mechanical energy to electrical energy, and hence, reduced brightness of the light source 102.

On the other hand, those materials having good susceptibility or permeability, good hysteresis, and high remanence, such as permanent magnets, some rare earth magnets, or ferromagnets, may be effective in initiating, maintaining, regenerating and/or increasing proper magnetization of the connecting body 103 or 103', and hence the brightness of the light source 102.

At the same time, all ferromagnets may also have a maximum temperature where the ferromagnetic property disappears as a result of thermal agitation. This temperature is called the Curie temperature. As long as the autoclaving temperature stays below this temperature, the magnetic properties may be maintained and the light source brightness is probably not affected. However, even below the Curie temperature, continual use and autoclaving may gradually reduce the magnetic property of the magnetic source 410, though the brightness of the light source 102 may remain in the useful range.

Autoclave in general is done above about 120° c. Therefore any magnetic source having a Curie temperature above that temperature is not likely to be affected by autoclaving.

Some rare earths, for example, gadolinium, have unusual superconductive properties. As little as 1 percent gadolinium may improve the workability and resistance of iron, chromium, and related alloys to high temperatures and oxidation. However, gadolinium has a Curie temperature at about room temperature, and thus may not be suitable for use as a portion of the connecting body 103, if autoclaving of such is to be customarily performed.

In one embodiment, if the magnetic material or source 410 used includes gadolinium or others having a low Curie temperature, it may be removable prior to autoclaving. The magnet, as long as it is in sufficiently close proximity to the connecting body 103, 103' and/or the insert 100 during use, has value in initiating, re-magnetizing and maintaining proper magnetization of the connecting body 103 or 103'.

In one aspect, the magnetic source may also be coated with a coating material for durability and/or corrosion resistance. The coating may include a polymeric material, a metallic coating, a non-metallic inorganic coating or combinations thereof. Examples of suitable polymeric material may be any that can be film forming either from solution, melt extruded or cast and may include those that are suitable for the tip 102 construction mentioned above. Examples of metallic coatings may include metallic nitride and carbide coatings such as titanium nitride, titanium carbide and so on. Examples of inorganic coatings may include ceramic coatings, diamond-like carbon coatings and the like.

Referring now to FIG. 7C, the connecting body 103 may also have formed thereon a circular groove 138 near its distal end and close to the tip portion 102. An O-ring 136 is seated in the groove 138, as noted before in connection with FIG. 6C. When the illumination energy bobbin 126 is mounted on the connecting body 103, the O-ring 136 provides a seal between the connecting body 103 and the illumination energy bobbin 126, when present, so as to prevent undesired fluid leakage. The illumination energy bobbin 126 may be formed as one-piece, and may be slid onto and snap/pressure fit to the connecting body and/or the retaining ring 111.

As also shown here in FIG. 7C, the O-ring 106 is disposed over the groove 120 on the retaining ring 111.

In one embodiment, the bobbin 126' may be a light transmitting cylinder or tube that may act as a light guide or light pipe 101c for transmitting light from the light source 101b located away from the tip 102', as exemplified in FIG. 7. In one aspect, the light guide or light pipe 101c may be configured from a material having internal reflective surfaces, or the internal surfaces may be coated with a material having total internal reflection. In another embodiment, the bobbin 126' may be configured from a fiber optic bundle. In other embodiments, the bobbin may be configured of any suitable material.

Figure 22A:
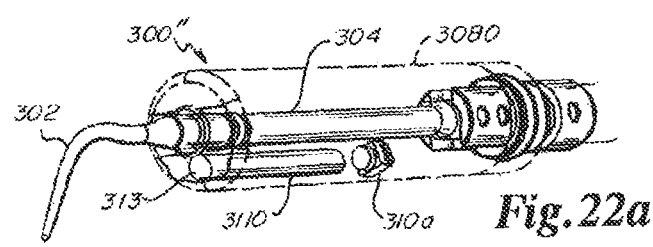
FIGS. 22A and 22B show partial see-through perspective views of inserts with light sources and light transports away from the distal ends.

In another embodiment, as shown in FIG. 22A, an insert 300" may include a light source 310a, which may be disposed distal to the tip 302, and a light transport 3110, such as a light guide or light pipe exit point may be used. The light transport 3110 may in general carry light from the light source 310a to a light exit 313 which may be disposed such that light may be directed to the field of work. The light source 310a and the light transport 311 may in general be enclosed by the grip portion 3080.

Figure 22B:
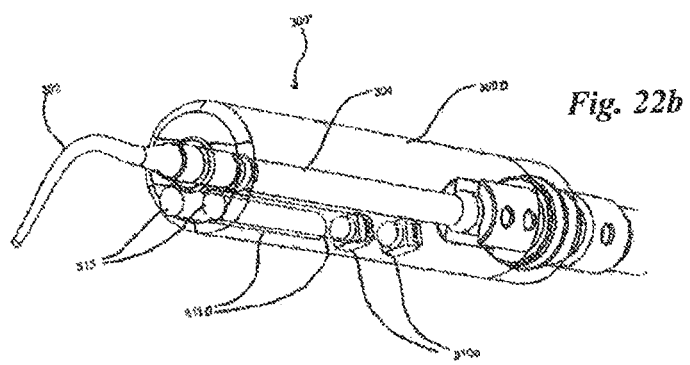

In other embodiments, a plurality of light ports 313, with their respective light sources 310a and light transports 3110, as shown in FIG. 22B, may be integrated with the insert 300". The plurality of light sources 310a can also have one light port 3110. In still other embodiments, the light transports 3110 may not be integrated with the insert 300", but may instead be non-integrally attached to the insert 300" and/or the grip portion 3080, or only one light transport 3110 is integrated with the insert 300" and additional ones are not.

The light transports 311, as shown in FIGS. 22A and 22B, such as the light exit ends of fiber optic bundles, may be individual elements running from the light source 310a to the light exits 313 or they may form part of illumination energy coil 314 (not shown), the grip portion 3080 or the connecting body 304.

It can be seen in FIGS. 7C and 7D1, that the illumination energy coil 99 is wound around the illumination energy bobbin 126, which is mounted in a surrounding relationship with the connecting body 103. The bobbin 126, for example, may be made of high temperature plastic such as ULTEM® or any other suitable material mentioned above for the construction of the tip 102. The amount of voltage generated in the illumination energy coil 99 depends on such factors as the number of coil turns, the location of the illumination energy coil 99 with respect to the connecting body 103, the speed and frequency of the connecting body movement, the material used for the connecting body, and the like.

By way of example, when the illumination energy coil 99 may be made of, for example, an 18 gauge copper wire and have multiple turns and the connecting body 103 is, for example, made of 17-4 PH stainless steel, or 420 stainless steel, as mentioned above, the voltage signal having between about, for example, 1 and about 10 volts, more for example, about 1 to about 5 volts, peak-to-peak, may be generated with the vibration frequency of 25 kHz. Those skilled in the art would appreciate that the magnitude of the voltage generated will generally increase as the number of turns and/or the vibration frequency increase.

In addition to the use of wires as an exemplary embodiment, a coil 99 may include any appropriate structure that may define at least a part of closed electrical pathway that may be induced by an appropriate changing magnetic flux. Such structures may include a single wire coil, multiple wire coils, wire flat spirals, wire conical coils and/or any other appropriate conductive structure that may properly be induced by a changing magnetic flux. Wire structures may be wound about a structurally defining element, formed and retained by their own rigidity, formed and retained within a structural material such as resin, and/or by any other appropriate method. In some embodiments, wire structures may be disposed on or within a flexible substrate and may be formed into an appropriate shape, orientation and/or form. For example, wire segments and/or structures may be disposed within a tape or other appropriate strip-like material. Such tape may then be wrapped around structurally defining elements to define wire structures such as coils. Electrical contacts may be disposed on the tape such that the embedded wires may be connected to other electrical elements. Examples of appropriate materials for embedding wire structures may include any substantially flexible and non-conductive materials, such as, for example, polyimide films such as Kapton produced by DuPont.

Further, in the illustrated embodiment, the voltage may increase as the illumination energy bobbin 126 (and the illumination energy coil 99) is mounted closer to the nodal point on the connecting body 103 than to the distal end where the tip 102 is attached to. The nodal point is where the magnitude of the longitudinal waves on the connecting body 103 is close to zero, and the longitudinal stress is at the maximum, and may, in FIG. 7C, be the location where the gripping elements 132 are attached to the connecting body 103 (i.e., the indentations 139), as noted above.

Surprisingly, the presence of the magnetic material increases the brightness of the light source to an extent that it render the location of mounting of the illumination bobbin 126 irrelevant, thus increasing the flexibility and robustness of manufacturing.

It can be seen in FIG. 7C that the illumination energy bobbin 126 may have formed thereon, for example, a bracket 141 and a seat 142 for mounting the LED 101 thereon. Further, the illumination energy bobbin 126 has formed thereon a flange 143 and a generally cylindrical chamber 144, between which the illumination energy coil 99 is mounted. The generally cylindrical chamber 144 has formed thereon a flange 145. The illumination energy bobbin 126 also includes a ring section 146 attached to the chamber 144. The ring section 146 abuts the flange 121 of the retaining ring 111 when the ultrasonic dental insert 100 has been assembled.

Figure 5:
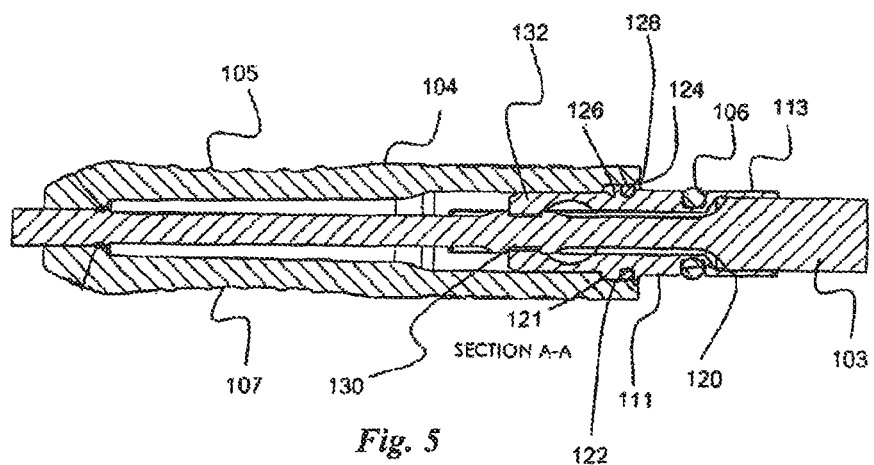
FIG. 5 is an enlarged cross-sectional view of the ultrasonic insert of FIG. 3 taken along the A-A line, and showing the O-ring.

FIGS. 7D1, 7D2, 7D3, 7D4 and 7D5 each illustrates an exemplary embodiment of the illumination energy bobbin 126 of FIG. 7, showing the possible location of the magnetic material or source 149. As seen in the exploded view in FIG. 7D1 or D2, the illumination energy bobbin 126 has formed thereon away from the ring section 146 a tube portion 140 which envelops the portion of the connecting body 103 near the tip 102 (not shown). In the described embodiment, the fluid enters the illumination energy bobbin 126 through the ring section 146, and exits the illumination energy bobbin 126 through the tube portion 140. The illumination energy coil 99 interfaces with the pins or electrodes 101a, 101b (FIG. 7D1), or 101b1 and 101b2 (FIG. 7D2) of the light source 101 (FIG. 7D1) or 101b (FIG. 7D2) through the ends of the coil 99a, 99b respectively, as illustrated in FIG. 7D5, such that electrical energy may be passed from the illumination energy coil 99 to the light source 101. The illumination energy coil 99 may further have tape or other holding material 97, for example, disposed over at least a portion of the coil to maintain proper positioning and to prevent unwinding of the coil 99.

In accordance with the exemplary embodiment of the invention, the bobbin 126 further includes slots or other holding features 147 disposed near the light emitting circuitry, including the light source 101 and the illumination energy coil 99, as shown in FIGS. 7D1 and D5, or 7D2, D3 and D4. In the present embodiment, the slots or holding features 147 may be for example, of a box-like shape, and may be adapted to receive and retain magnets or magnetic source 410 or elements 149 in proximity to the light emitting circuitry so as to initiate, increase, maintain or re-magnetize the insert 100 and tip 102 to allow the connecting body 103 or 103' to generate an electromagnetic field during operation of the insert 100 to power an attached light source 101 such as an LED. The holder 147 may be in close proximity to the coil 99 (not shown here) inside the grip 104 that is used to generate the electromagnetic field that generates power to light the LED 101 connected to the insert 100 or 100'. The presence of this magnetic material or source 410 may allow the connecting body 103 or 103' to retain its magnetic properties in an optimal manner even after exposure to heat or physical shock, as described above.

Figure 3:
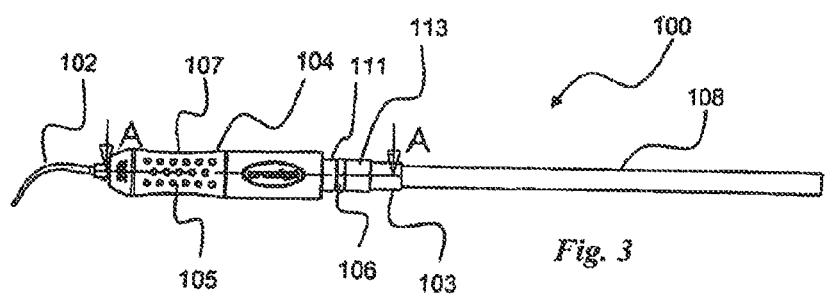
FIG. 3 is a side view of the dental tool insert of FIG. 2.
Figure 3A:
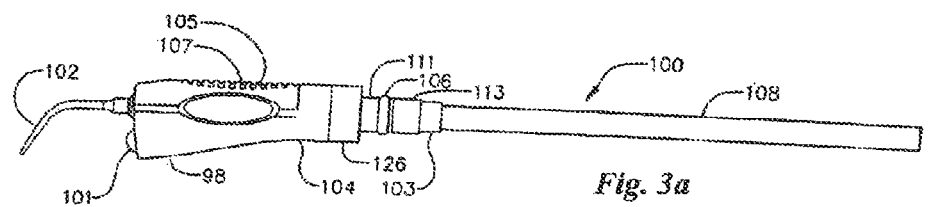
FIG. 3A is a side view of another embodiment of FIG. 3, having a light source.

In one embodiment, the illumination coil 99 may be wound about an illumination bobbin 126, as shown in FIG. 7D3. For the energy generated to be used to light up the light source 101, the bobbin 126 may be made from a non-magnetic material, for example 303 & 316L stainless steel and other non-magnetic metals, polymers, cellulose, minerals, ceramics or a combination thereof.

Figure 23:
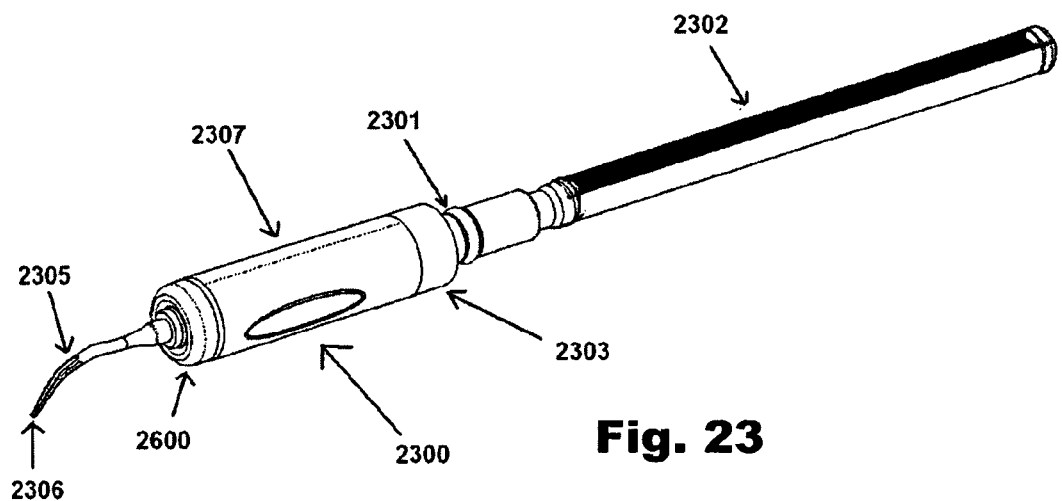
FIG. 23 shows a perspective view of an insert with a one-piece bobbin in one embodiment of the present invention
Figure 25:
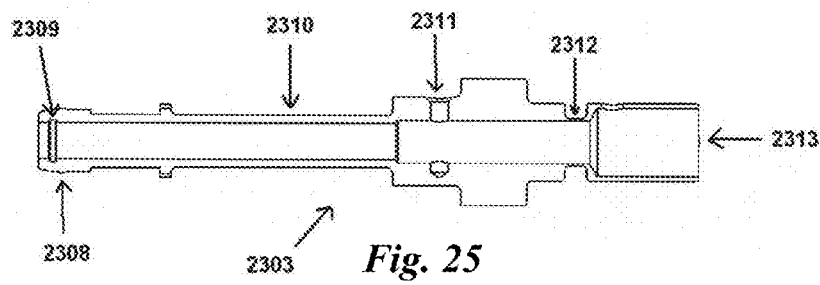
FIG. 25 shows a cross sectional view of a one-piece bobbin design in one embodiment of the present invention.
Figure 31:
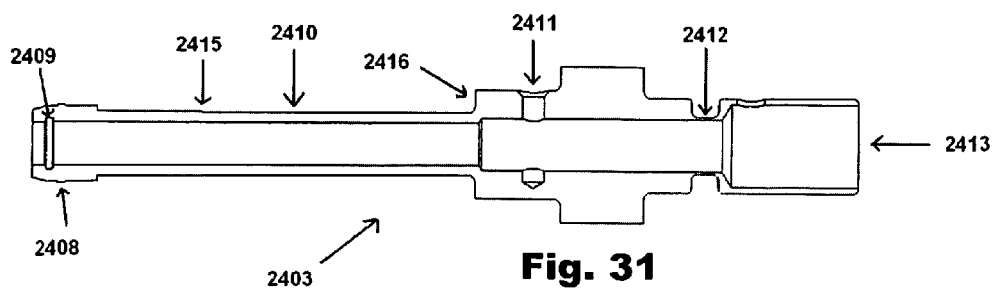
FIG. 31 shows a cross sectional view of a one-piece bobbin design in one embodiment of the present invention.

In one exemplary embodiment of the invention, the retaining ring 111 and the bobbin 126 may be in a one-piece unitary structure 2303, as shown in FIG. 23. The unitary structure may be made from a high temperature material. Initial machining or forming of the high temperature material may or may not cause stress and or magnetism to occur in the unitary structure 2303. If this unwanted stress and or magnetism occurs, annealing of the part may be necessary to relieve any stress and or magnetism. Annealing is a process that produces conditions by heating and maintaining a suitable temperature, and then cooling. Annealing is used to induce ductility, relieve internal stresses, refine the structure, and improve cold working properties. One of the advantages of having a one piece combined bobbin 126 and the retaining ring 111 structure, for example, 2303 and 2403, may eliminate the need for a threaded connection between the bobbin 126 and retaining ring 111 and/or the use of an O-ring, such as o-ring 134, as shown in FIG. 7c, thus eliminating a potential leak path, reducing the amount of assembly time, and allowing for the reduction of parts. When the high temperature material, for example, is used to produce the unitary structures 2303 and 2403, the structures 2303 and 2403 may be assembled to the ultrasonic transducer body 2305 prior to the tip 2306 being bent and heat treated. Once the tip 2306 is bent into a desired orientation, the high temperature one-piece unitary structures 2303 and 2403 allow for the working tip to be heat treated with the unitary structures 2303 and 2403 loosely attached. The unitary structures 2303 and 2403 may also be pre-treated with Teflon or other low friction surface treatments in the grove location 2312 and 2412, as shown in FIGS. 25 and 31, respectively, for seating an o-ring 106, as discussed before, or 2301, as shown in FIG. 23.

Figure 27:
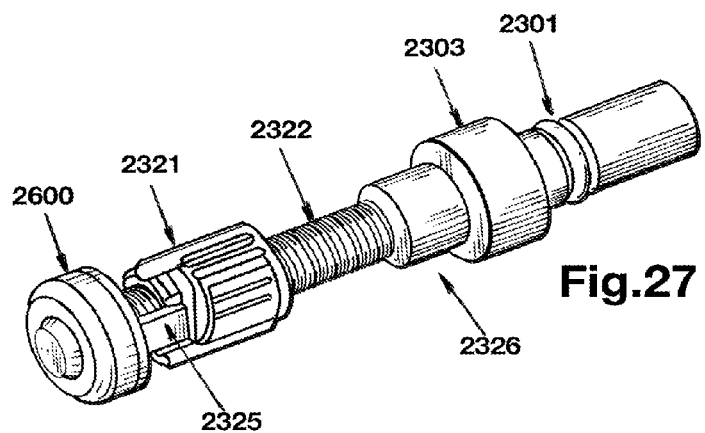
FIG. 27 shows a motor assembly that includes a one-piece bobbin in one embodiment of the present invention.
Figure 33:
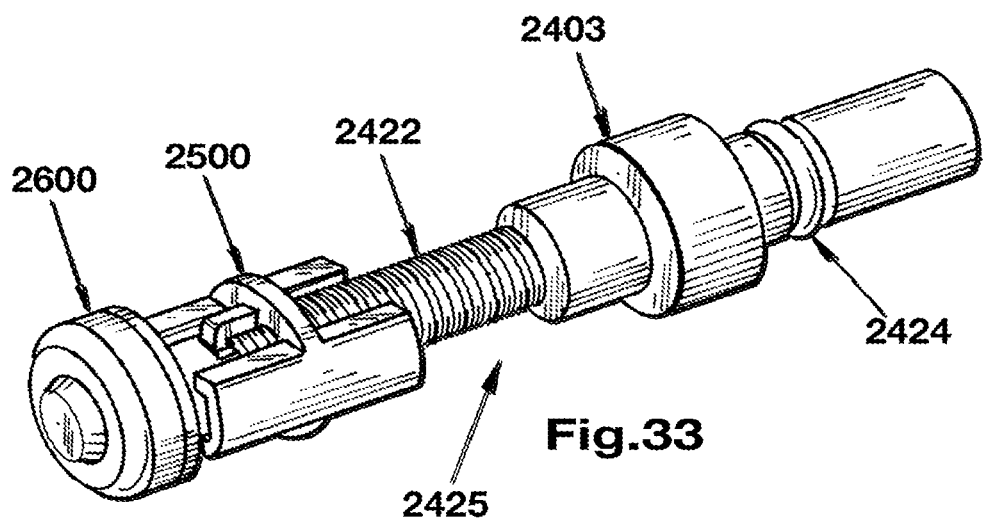
FIG. 33 shows an isometric view of a motor assembly that includes a one-piece bobbin in one embodiment of the present invention.

In one aspect, heat treatment may be utilized to strengthen the working tip 2306 after bending to minimize the potential for breaking during use, especially prolong use. It may also be more advantageous to heat treat the working tip after it is bent and not before. After heat treatment, a distal O-ring 2800 may be inserted prior to the coupling of the unitary structure 2303 or 2403 to the working tip by means of a pin, for example, 2328, as shown in FIGS. 28a and 34a. Once the pin 2328 is secure, the winding of the illumination coil 2322 about the bobbin 2303 or 2403 may commence to create part of the transducer or motor 2326 or 2425, as shown in FIGS. 27 and 33 respectively.

Figure 28:
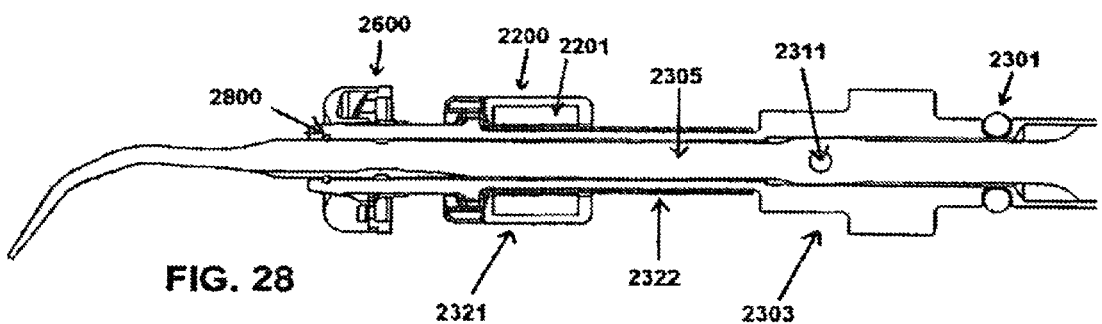
FIGS. 28 and 28a each shows a cross sectional view of a motor assembly that includes a one-piece bobbin in one embodiment of the present invention.
Figure 28A:
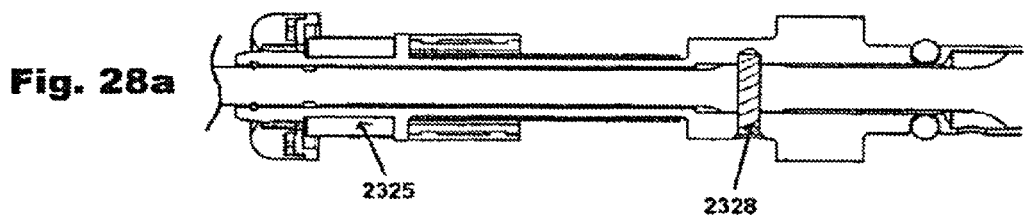

In FIG. 28, hole 2311 is shown as the location where pin 2328 may be inserted. Magnet 2201 that is part of saddle half 2200 and saddle assembly 2321 is also shown in the cross section. Bobbin 2303, ultrasonic transducer body 2305, lens assembly 2600, O-ring 2301, illumination coil 2322, distal O-ring 2800 are also shown in cross section in FIG. 28. Magnets 2325 are shown in the cross-sectional view in FIG. 28a.

To complete the assembly of motor or transducer 2326 or 2425, a lens assembly 2600, as shown in FIGS. 35 and 35a, may be attached to the distal end of the motor or transducer 2326 or 2425. The light sources may be connected to the illumination coil 99, as discussed previously when referring to FIG. 7D1, or illumination coil 2322, as shown in FIG. 27.

In one embodiment, the unitary structure 2303 or 2403 may be made by machining, such as computer numerical control (CNC) machining. In another embodiment, it may be created by investment casting or lost-wax casting, the oldest known metal-forming technique. In a further embodiment, a powdered metal sintering process or by a thixomolding process. In yet another embodiment, it may be created by metal injection molding (MIM). This latter embodiment presents a more cost effective way to create more complex geometries in higher volumes and allows for a multitude of material choices.

Metal injection molding is an effective way to produce complex and precision-shaped parts from a variety of materials. It is common for this process to produce parts for about 50% less than the cost of CNC machining or investment casting. At the same time the true value of MIM comes from its ability to produce parts with complex shapes, superior strength, and excellent surface finish in combination with high volume manufacturing capability. The total cost savings results from the combination of shape complexity, production volumes, size of part and material used. The sizes of parts currently typical of MIM are generally between about 10 grams to about 250 grams, for example; more for example, about 30 grams to about 150 grams per piece.

Figure 36:
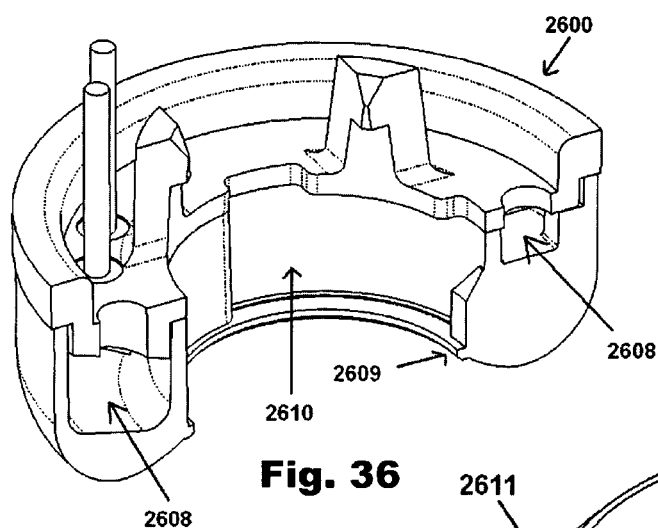
FIG. 36 depicts a cross sectional isometric view of a lens assembly in one embodiment of the present invention.
Figure 37:
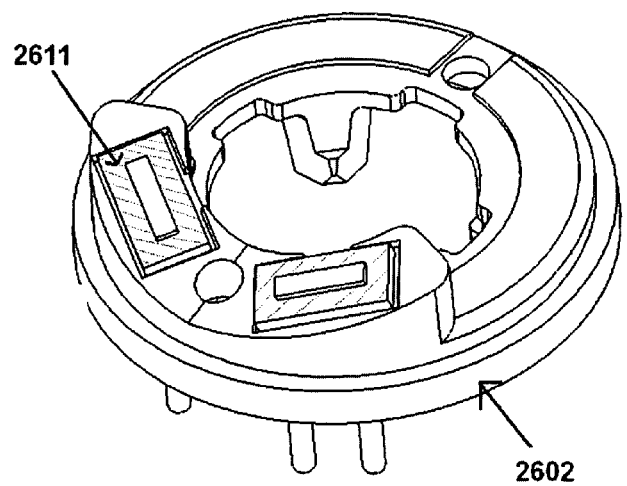
FIG. 37 depicts a top isometric view of a lens base in one embodiment of the present invention.

Referring to FIGS. 35, 35a and 36, the lens assembly 3600 may be made from, for example, a transparent polymer. In one embodiment, the lens assembly 3600 may be made from two halves: a lens half 2601 and a base half 2602. The two halves may be ultrasonically welded together or glued together utilizing a structural adhesive, such as an epoxy, a UV curable epoxy or a solvent based adhesive. At the bottom of the lens base, there may be attachment features 2604, as shown in FIG. 35a, that may allow the base 2602 and thus the entire lens assembly to attach itself to the bobbin/motor assembly 2425 and 2326, respectively. In addition, at the bottom of the base 2602, there is for example, an opening 2606 or 2605 that may allow for the pumping of, for example, uncured epoxy or other uncured structural adhesive into the lens assembly 3600. One opening 2606 or 2605 may be utilized for pumping in the epoxy and at the opposite end, another opening 2606 or 2605 may be used for allowing any trapped air to escape and overflow of any epoxy to occur. One advantage of filling the lens with epoxy is to minimize or prevent any trapped gas inside the lens from creating condensation inside the lens, and also any trapped air from super heating during sterilization, which may cause premature failures if the hermetic seal between lens 2601 and base 2602 is compromised.

In FIG. 23 is shown yet another version of the rotatable ultrasonic dental insert 2300 in which a one piece bobbin 2303 is utilized. A tip 2306 is utilized as the surface that would interface with a patient's tooth. Member 2305 is the ultrasonic transducer body that is attached to stack 2302. An O-ring 2301 is shown that may easily rotate around the one piece bobbin 2303 when inserted into handpiece 200.

Figure 38:
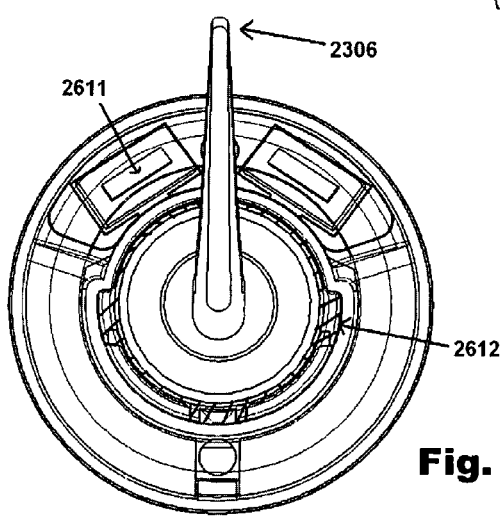
FIG. 38 shows a top view of a lens base in one embodiment of the present invention, showing a grip material filling a gap between the lens assembly and the one-piece bobbin.

FIG. 38 shows a top view of a lens base 2602 in one embodiment of the present invention, showing a grip material filling a gap between the lens assembly and the one-piece bobbin. Lens 2611 and tip 2306 are also depicted. A grip portion 2307 may be made by overmolding the subassembly with a soft-grip like material. This material may also flow easily into all remaining cavities and crevices as shown in FIG. 38 in section 2612 during manufacture. When the material flows into region 2612, it thereby provides a gap filling material that keeps unwanted bacteria and debris from getting into this region during normal use. Without material flowing into the region, there may leave an undesirable space to allow unwanted debris to collect there.

Figure 24:
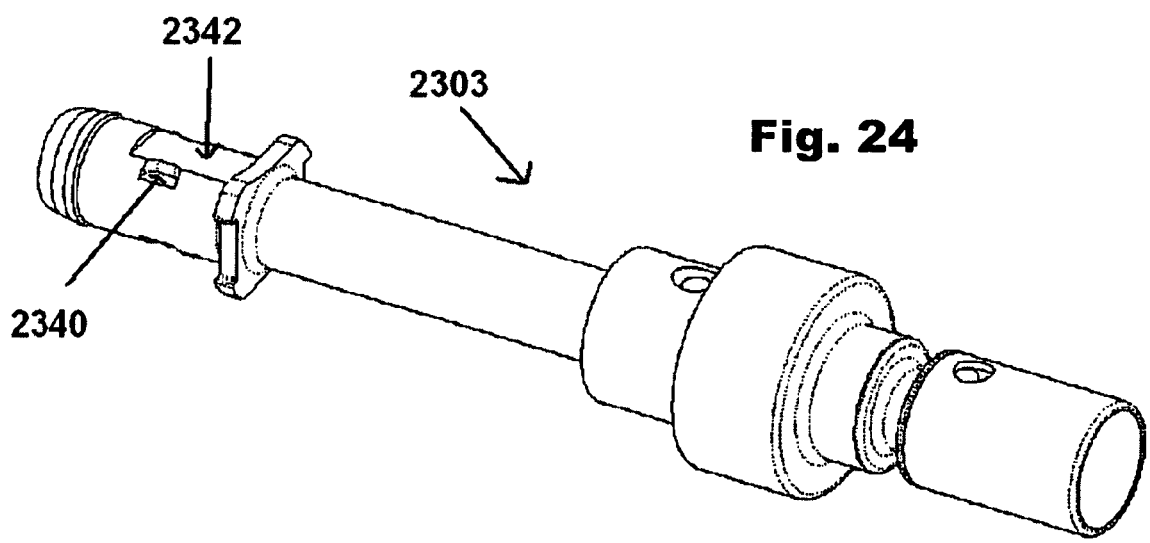
FIG. 24 shows a perspective view of a one-piece bobbin design in one embodiment of the present invention.

Referring to FIG. 24, yet another one piece bobbin 2303 is shown. Section 2342 may be utilized in one instance to allow for the placement of a magnet or magnets. Region 2340 may be utilized as a region for snap fit 2604 on lens assembly 2600, as shown in FIG. 27, to grip and hold it to bobbin 2303. Section 2310, as exemplified in FIG. 25, may be utilized as the winding area for wire 2322, as shown in FIG. 27. An O-Ring groove 2309, as shown in FIG. 25, is utilized to hold an O-ring 2800, as shown in FIG. 34, against ultrasonic transducer body 2305, as shown in FIG. 25.

Figure 29:
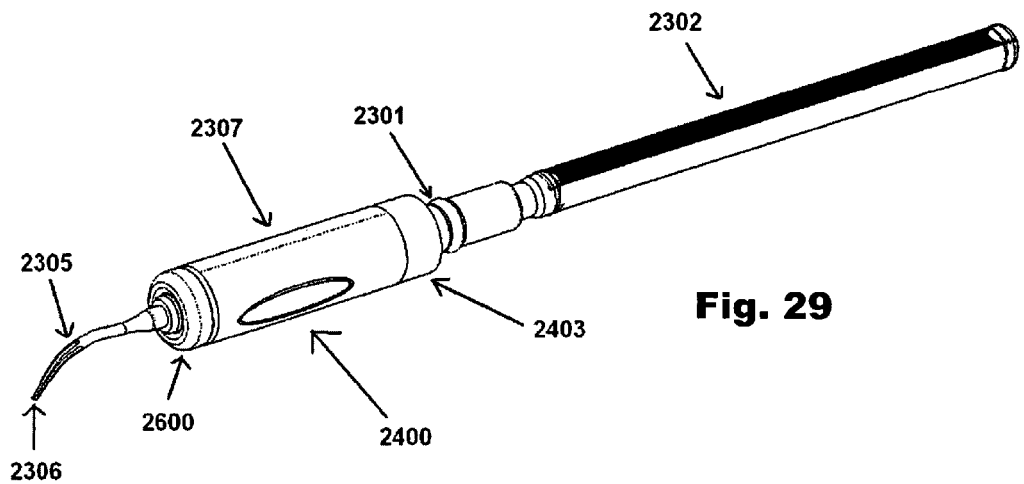
FIG. 29 shows a perspective view of a rotatable insert with a one-piece bobbin in one embodiment of the present invention

Referring again to FIG. 25, a hole 2311 may be utilized to allow for an anti-rotation element 2328, as shown in FIG. 28a, to be placed into the hole 2311, thus mounting the bobbin 2303 to the ultrasonic transducer body 2305, as shown in FIG. 28. A flange 2308 may be utilized as a shutoff for lens assembly 2600 at flange 2609. This may keep overmolded grip handle material 2307, if present, as shown in FIG. 29, from flowing where it is not supposed to. Fluid flow path 2313 and coating O-ring groove 2312 are also shown in FIG. 25.

Figure 26A:
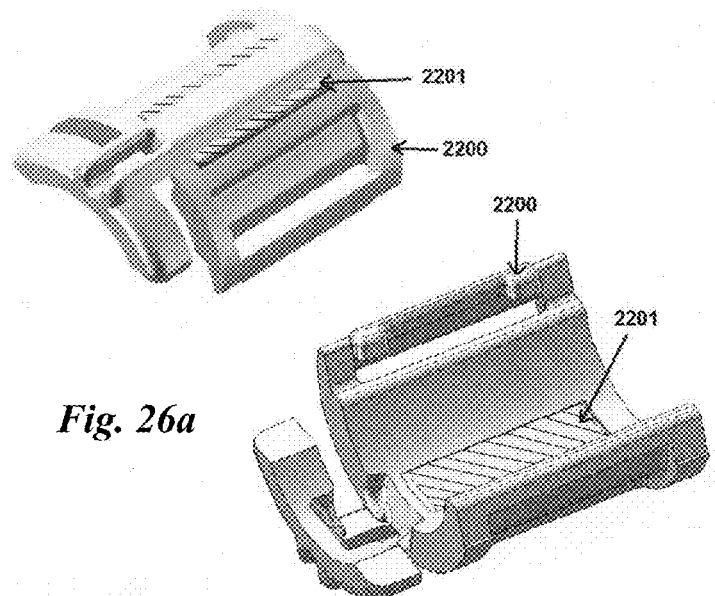
FIG. 26a shows a top and bottom isometric view of one-half of a saddle in one embodiment of the present invention.
Figure 26B:
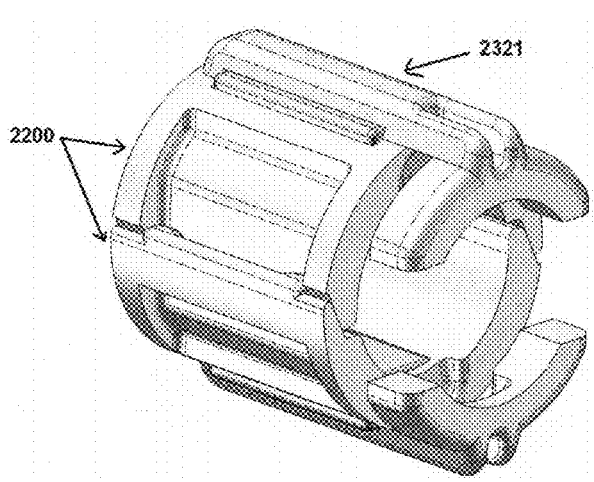
FIG. 26b shows a perspective view of a saddle assembly in one embodiment of the present invention.

In FIG. 26a, the saddle half 2200 is shown. The saddle half 2200 may be made by insert molding and/or assembling magnet 2201 into the design. As shown in FIG. 26b, saddle half 2200 is to be attached to itself to create saddle 2321 over top of bobbin 2303 as shown in FIG. 27. Magnets 2325, as shown in FIG. 27, may be placed on either side of bobbin 2303 in symmetrical locations 2342, as shown in FIG. 24. FIG. 28 shows a cross sectional view of rotatable ultrasonic dental insert 2300 prior to it being overmolded with grip 2307, as shown in FIG. 29.

Figure 32:
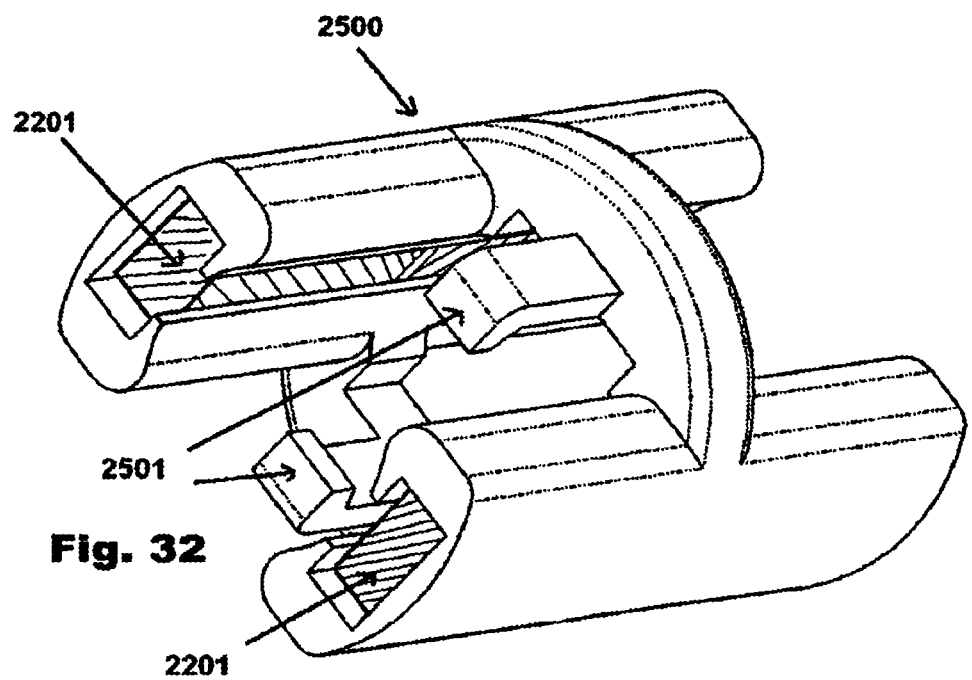
FIG. 32 shows an isometric view of a one-half of a saddle in one embodiment of the present invention.

In FIG. 29, another one-piece bobbin 2403 to create rotatable ultrasonic dental insert 2400 is shown. The difference and advantage of bobbin 2403 over bobbin 2303 is that bobbin 2403 allows a one or two piece saddle that may hold 4 magnets to be assembled onto bobbin 2403 by reducing the height of flange 2415, as shown in FIG. 31. Symmetrical location 2441, as shown in FIG. 31, may be utilized to hold saddle assembly 2500 of FIG. 32, by means of snap fits 2501 or by other means such as glue, pin, so on, as shown in FIG. 34.

Figure 30:
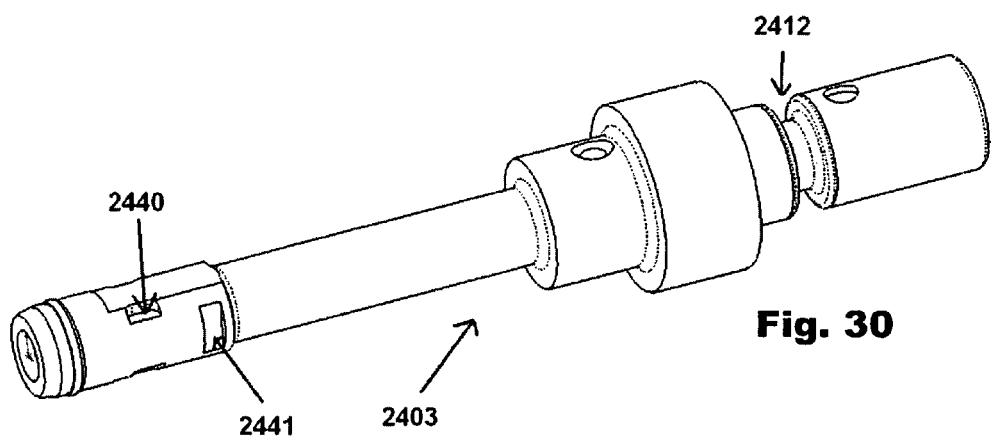
FIG. 30 shows another embodiment of a one-piece bobbin design in one embodiment of the present invention.

Referring to FIG. 29, region 2440 may be utilized to attach lens assembly 2600. O-Ring section 2412 of FIG. 30 may be coated with low friction material 8100 shown in step 2702 in FIG. 39 to allow O-Ring 2424, as shown in FIG. 33, to rotate easily about bobbin 2403. Flanges 2415 and 2416 as shown in FIG. 31 may be utilized to help illumination coil 2422 (as shown in FIG. 33) during winding and from moving out of its trough, the area between flanges 2415 and 2416.

Referring to FIG. 31, a front O-ring groove 2409 may hold an O-ring 2800 (as shown in FIG. 28) in place that provides a seal to ultrasonic transducer body 2405, as shown in FIG. 34. Flange 2408, as shown in FIG. 31 may be utilized as a shutoff for Lens assembly 2600 at flange 2609, as shown in FIG. 36. This may again keep overmolded grip handle material 2307 (as shown in FIG. 29) from flowing past the intersection of flange 2609 and flange 2408 and thus allow the material in region 2610 to freeze off quickly during molding. Fluid flow path 2413 and coating O-ring groove 2412 are also shown in FIG. 31.

FIG. 33 depicts a motor 2425 with bobbin 2403 assembled. An o-ring 2424 sits in a groove to allow for rotation when the groove is coated with low frictional material 8100 shown in step 2702 in FIG. 39.

FIGS. 34 and 34*a* show a side and top cross sectional views of rotatable ultrasonic dental insert 2400 prior to it being overmolded with grip 2307. In FIG. 34, hole 2411 is the location where pin 2328 may be inserted. Magnet 2201, a part of saddle 2500, is also shown in the cross sectional view in FIG. 34*a*. Bobbin 2403, connecting body 2405, lens assembly 2600, O-ring 2401, illumination coil 2422, distal O-ring 2800 are also shown in cross section in FIG. 34, depicting all of the components that make up motor assembly 2425.

FIG. 35 shows a top and bottom isometric view of lens assembly 2600. Lens 2601 and lens 2602 may be bonded together with two LEDs 2611 inside. Contact wires 2603 protrude from Lens assembly 2600. Curable epoxy, either with light, heat, catalyst, or moisture, is pumped into lens assembly through hole 2606. Air is allowed to escape and epoxy to overflow through hole 2605. Curable epoxy is then cured with either UV light, white light or cures due to a chemical reaction. Curable epoxy fills gap 2608. Region 2610 is later filled with grip overmold material 2307 in both 2300 and 2400 devices. Region 2610 is part of gap 2612.

Figure 39:
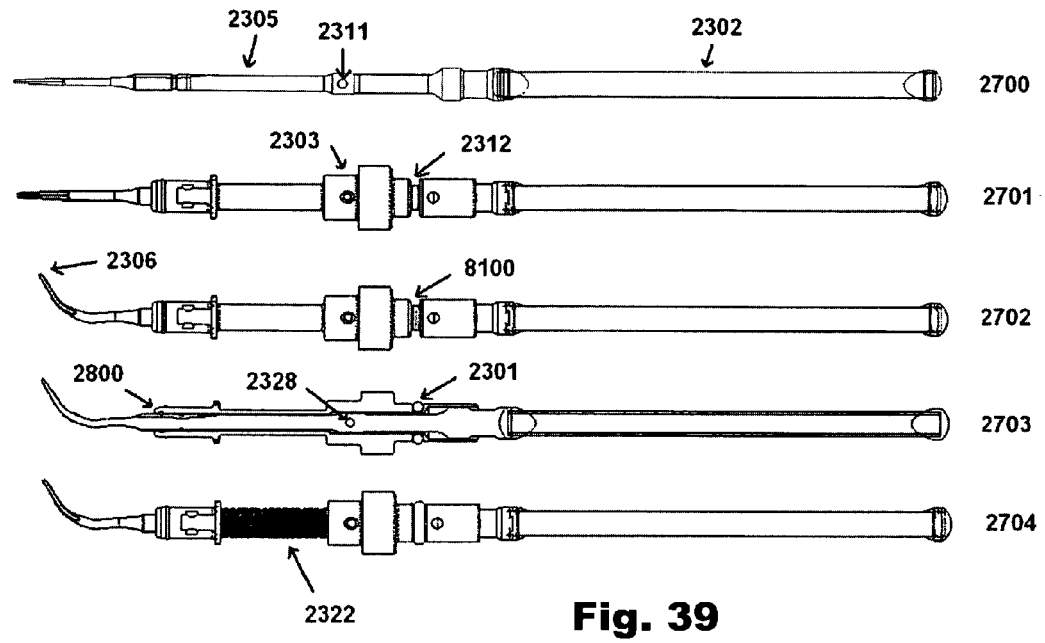
FIG. 39 shows various forms in consecutive assembly steps for making an insert in one embodiment of the present invention.
Figure 40:
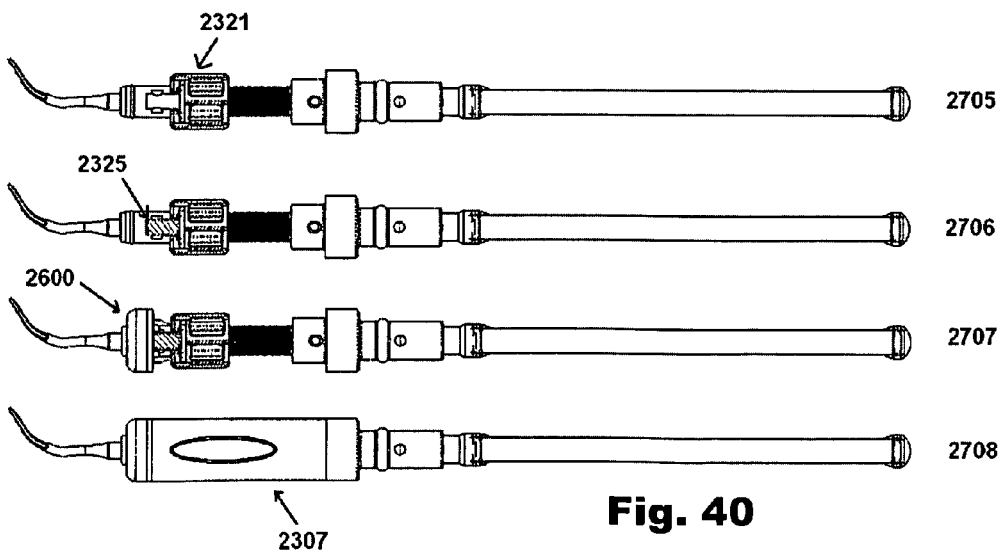
FIG. 40 shows various forms in consecutive assembly steps for finishing an insert in one embodiment of the present invention.

There may be many other acceptable methods for assembling together all of the components as the following is only one example. FIGS. 39 and 40 depict one possible order of assembly to create device 2300. First ultrasonic transducer body 2305 is welded to stack 2302 in step 2700. The, one piece bobbin 2303 is loosely placed over the body and stack assembly in step 2701. Tip 2306 may be made by bending an end of ultrasonic transducer body 2305 and the subassembly is heat treated to strengthen the bent tip 2306 in step 2702. The bobbin 2303 may be treated in O-Ring gasket region 2312 with a lubricous coating 8100 such as, for example, the low frictional material discussed above, such as Teflon®, as shown in step 2702. O-Ring 2800 is placed into O-Ring recess 2309 and O-ring 2301 into O-Ring recess 2312, as shown in step 2703. A pin 2328 is then inserted into a hole 2311 in order to keep bobbin 2303 from rotating. In step 2704, bobbin 2303 is wound with copper wire 2322. In step 2705, saddle half 2200 is assembled to itself around bobbin 2303 to form saddle assembly 2321. In step 2706, two magnets 2325 are assembled symmetrically about bobbin 2303. In step 2707, Lens assembly 2600 is attached to the end of bobbin 2303. Illumination coil 2322 may be attached to four wire leads 2603 in parallel. Wiring the two light-emitting diodes (LEDs) in anti-parallel or in parallel with reversed polarity from one another allows the LEDs to pulsate and toggle on and off due to the alternating current created in the illumination coil. Wiring the two LEDs in reversed polarity allows both positive and negative amplitude of the alternating current to be utilized. Finally subassembly 2707 is inserted into an injection molding tool to be inserted with grip 2307, as shown in step 2708, to form rotatable ultrasonic dental insert 2300.

In one embodiment, as shown in FIG. 16, an ultrasonic dental insert 1600 may include a tip 1602 which may be connected to a connecting body 1608 and a magnetostrictive stack 1606. The insert 1600 may also include an illumination bobbin 1610 and a light source 1620. The illumination bobbin 1610 may include an illumination energy coil 1604 which may substantially surround the illumination bobbin 1610 and may provide electrical energy to light source 1620. The illumination bobbin 1610 may be made of any light transmitting material so that it may carry light from light source 1620 towards the tip 1602.

As seen in FIG. 16A, which shows an exploded view of the ultrasonic dental insert of FIG. 16, a light source 1620 may include a ring-shaped body 1622 which may include one or multiple light sources, in arrays of a ring or in arrays of concentric rings (not shown). The light source 1620 may be electrically connected to the illumination energy coil 1604 via electrodes 1624, 1626 and electrodes 1604*b*, 1604*c* on the coil 1604. The windings 1604*a* of the coil 1604 may run substantially the entire length of the bobbin 1610 such that it may provide the maximum amount of energy to the light source 1620. The bobbin 1610 and light source body 1622 may be constructed to include axial channels 1610*b*, 1620*a*, respectively to accommodate the insert tip 1602.

Figure 16B:
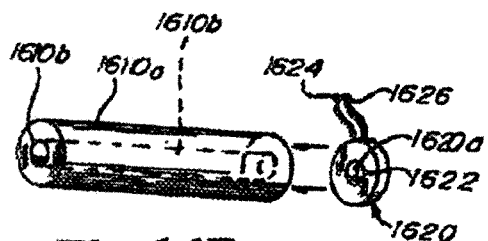
FIG. 16B illustrates the bobbin and light source of the ultrasonic dental insert of FIG. 16.

As illustrated in FIG. 16B, light from light source 1620 may be emitted and carried through the light transmitting material(s) of bobbin body 1610*a*.

In some aspects, the bobbin body 1610*a* may be internally reflective, as discussed above, such that it may transmit the majority of the light from the light source 1620 to its distal end through airspace and/or by reflective from its walls rather than through the side walls. In other aspects, the bobbin body 1610*a* may allow transmission of light through its side walls and as such may provide a greater field of illumination.

Figure 17:
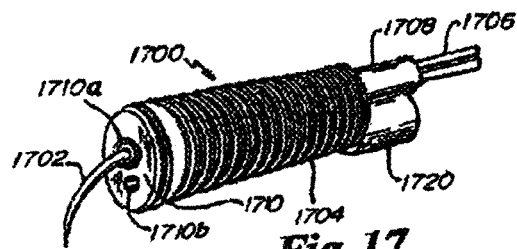
FIG. 17 is a perspective view of an ultrasonic dental insert having a light source and a bobbin that includes a light transmitting conduit in an exemplary embodiment of the invention.

In another embodiment, as exemplified in FIG. 17, an ultrasonic dental insert 1700 may include a tip 1702 which may be connected to a connecting body 1708 and a magnetostrictive stack 1706. The insert 1700 may also include an illumination bobbin 1710 and a light source 1720. The illumination bobbin 1710 may include an illumination energy coil 1704 which may substantially surround the illumination bobbin 1710 and may provide electrical energy to light source 1720. The illumination bobbin 1710 may include a light transmitting region 1710*b* that may transmit light from the light source 1720 by way of an internal light guide. The light guide may be solid and made of any light transmitting material so that it may carry light from light source 1720 towards the tip 1702. In another embodiment, the light guide 1710 may be hollow having internal reflective walls.

Figure 17A:
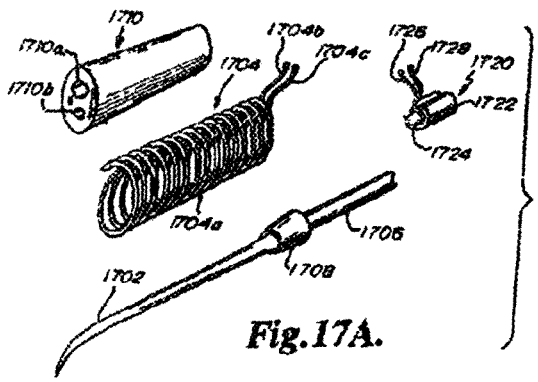
FIG. 17A is an exploded perspective view of the ultrasonic dental insert of FIG. 17.

As seen in FIG. 17A, which shows an exploded view of the ultrasonic dental insert of FIG. 17, a light source 1720 may include at least one light emitting element 1724 and a body 1722. The light source 1720 may be electrically connected to the illumination energy coil 1704 via electrodes 1726, 1728 and electrodes 1704*b*, 1704*c* on the coil 1704. The windings 1704*a* of the coil 1604 may run substantially the entire length of the bobbin 1710 such that it may provide the maximum amount of energy to the light source 1720.

Figure 17B:
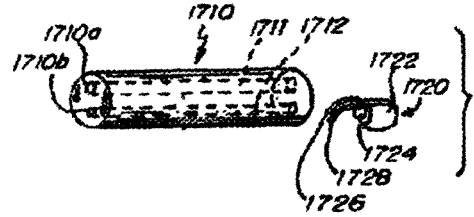
FIG. 17B illustrates the bobbin and light source of the ultrasonic dental insert of FIG. 17.

In one aspect, as illustrated in FIG. 17B, the bobbin 1710 may include a channel 1711 that may accommodate the insert tip 1702 and an internal light guide path 1712. The light source 1720 may interface with the light guide path 1712 at the end distal to the tip 1702, whereby the light guide path 1712 may transmit the emitted light toward the light emitting region 1710b at the end proximal to the tip 1702. The light guide path 1712 may be any form of conduit capable of carrying light from the light source 1720 to the light emitting region 1710b. In one embodiment, the light guide path 1712 may be, for example, a light transmitting member that may run the length of the bobbin 1710 from the light source 1720 to the light emitting region 1710b. The light transmitting member may be, for example, a fiber optic member that may be a single fiber or a bundle of fibers, a solid light guide such as glass or any suitable transparent/translucent polymer, and/or any other solid light transmitting material. In another embodiment, the fiber optic bundle may be bundled together at the light source 1720 and the exit port or ports 1710a or 1710b, but may be unbundled to fit through any available space in its path 1712. In other embodiments, the light guide path 1712 may be a hollow gas-filled, fluid-filled or vacuum space.

In some embodiments, the light guide path 1712 may feature reflective walls and/or be internally reflective such that it may better conduct light from the light source 1720 to the light emitting region 1710b.

In other embodiments, the light guide path 1712 may also include optically active features that may include, but are not limited to, focusing means, collimating means, diffusing means, polarizing means, filtering means and/or any other desired optically active features.

Figure 18:
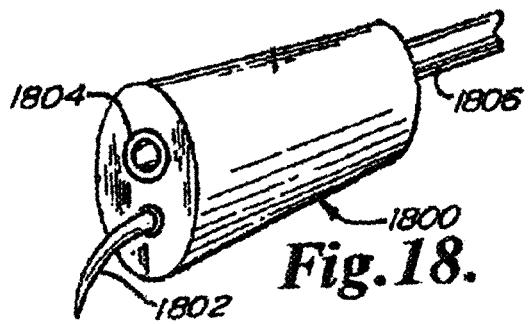
FIG. 18 illustrates an ultrasonic dental insert with a light emitting port.

In another aspect, as illustrated in FIG. 18, an ultrasonic dental insert 1800 may feature an interfacing port 1804. The interfacing port 1804 may emit light in any of the manners discussed above and may provide features for coupling an additional light guide member and/or other appropriate attachment.

Figure 18A:
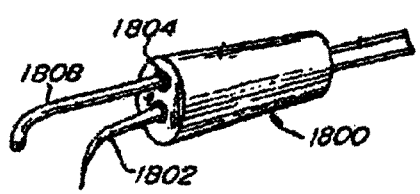
FIG. 18A illustrates an ultrasonic dental insert with a light pipe extending from the insert body.

In one embodiment, as illustrated in FIG. 18A, a light pipe 1808 may be interfaced to the interfacing port 1804. The light pipe 1808 may be adapted to direct light in any desirable direction in the field of work.

In some embodiments, the light pipe 1808 may allow light emission from only the tip 1802. In other embodiments, the light pipe 1808 may allow light emission from its walls.

In another embodiment, the light pipe 1808 may be constructed from an elastic and/or flexible light transmitting material such that it may be deformed to adjust the direction of the output light.

Suitable light transmitting materials may include, but are not limited to, glass, silica, transparent alumina and/or other inorganic transparent or translucent crystalline materials, acrylic polymers such as polymethyl methacrylate (PMMA), polycarbonate, polyethylene, polystyrene, combinations thereof and/or any other appropriate material that may substantially transmit light.

Internal reflection may be accomplished by a variety of methods, such as, but not limited to, engineering a boundary that creates a higher refractive index within the light-carrying material than in the surroundings, coating a light-carrying material with a reflective material, such as reflective metals including aluminum, copper and/or silver, liquid-crystal polymers, cholesteric polymers and/or any other suitable material that may substantially reflect light.

In another embodiment of the invention, to minimize the bulge in the grip portion 104, thinner and longer magnetic sources may also be used.

Figure 4E:
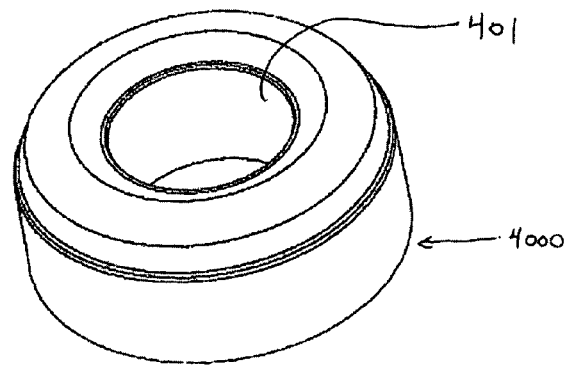
FIG. 4E illustrates an embodiment of a light source having more than one LEDs.
Figure 4E:
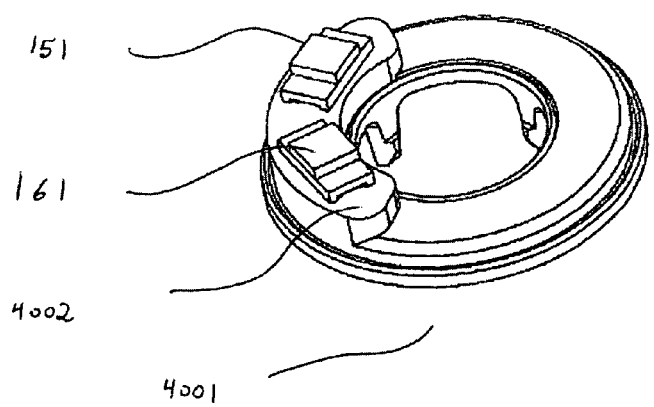

In a further embodiment of the invention, arcuate-shaped holders may be used, as disclosed above in connection with FIG. 4E, so as to conform more to the shape of the connecting body 103 and thus again minimize the bulge in the grip area 104, for example.

In FIG. 4E, an arcuate-shaped holder 400 is in the shape of a donut, having a through hole 401 in the middle through which the connecting body 103 passes. The holder 400 may be made in two-parts, a cover 4000 and a mounting part 4001. Two LEDs 151 and 161, or any number of LEDs, are mounted on a platform 4002. The cover 4000 is sized to fit over the mounting part 4001 to protect the LEDs and circuit board components. The cover 4000 may be formed separately and then welded onto the mounting part 4001, or it may be overmolded onto the mounting part 4001. However formed, the cover 4000 is transparent, translucent or is of any light transmitting material as discussed below, so as to not to obstruct light coming from the LEDs 151, 161.

Figure 7E:
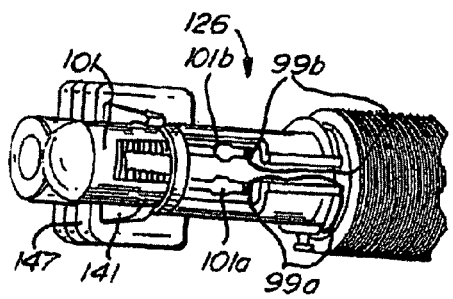
FIG. 7E illustrates the inclusion of a light source, a transducer and a full bridge rectification circuit.
Figure 7E:
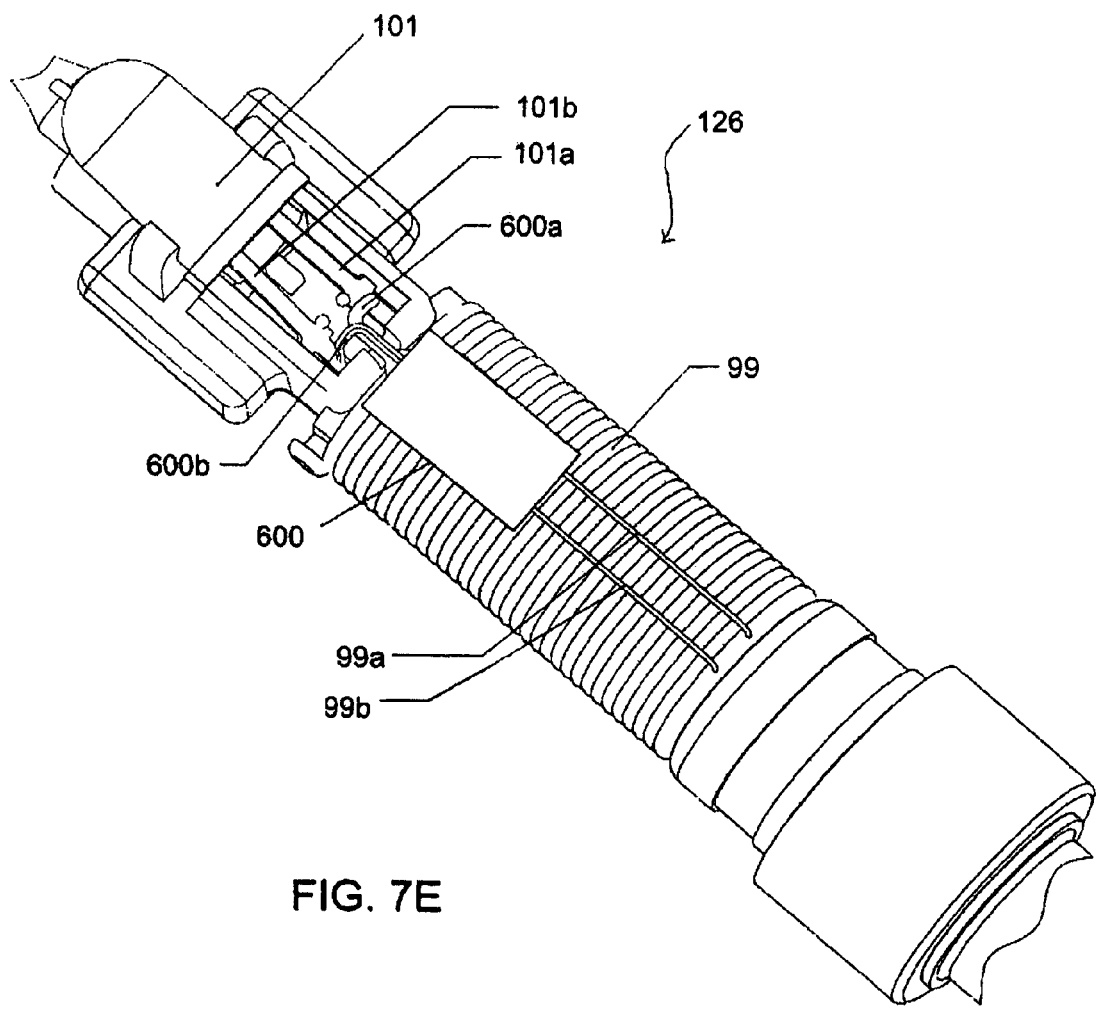

In some embodiments, the circuitry of the illumination energy coil 99 and light source 101 may include a source of rectification, as exemplified in FIG. 7E. In particular, the circuitry of the illumination energy coil 99 and light source 101 may include the use of a full-wave circuit that may increase the utilization of the energy provided by the ac current of the voltage signal generated by the illumination energy coil 99. The use of full-wave rectification circuitry may, for example, increase the utilization of the ac current voltage signal generated by the illumination energy coil 99 by allowing both the positive and negative phases of the ac current to contribute to the powering of a light source. Such full-wave rectification circuitry may, for example, substantially pass the positive phase of an ac current voltage signal to a light source while inverting the negative phase of the same ac current voltage signal before passing to a light source. The use of full-wave rectification circuitry may generate a substantially direct current voltage signal from the ac current generated by the illumination energy coil 99 when viewed from the light source 101.

In particular, this may be useful in powering LED light sources as such devices are only active when current is polarized in a particular direction and are not able to utilize both phases of an ac current voltage signal. Further, the generation of a more constant direct current voltage signal may aid in increasing the effective lifetime of a light source such as an LED, as a direct current voltage signal presents a steady current to the device rather than effectively turning the device on and off, as is the case with an ac current voltage signal.

Figure 10:
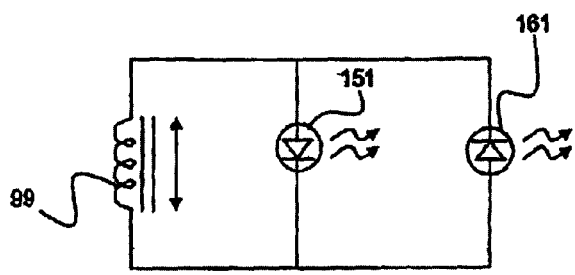
FIGS. 10, 10A and 10B illustrate light emitting circuitry of the integrated light source utilizing voltage smoothing circuits.
Figure 10A:
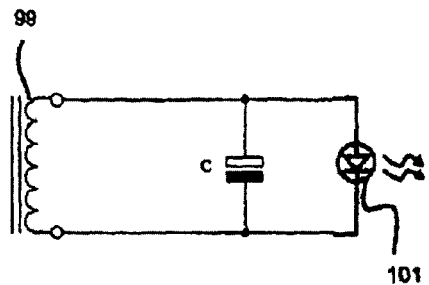
Figure 10B:
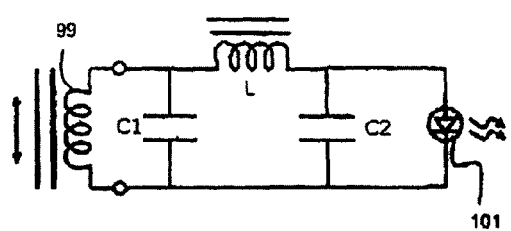
Figure 10C:
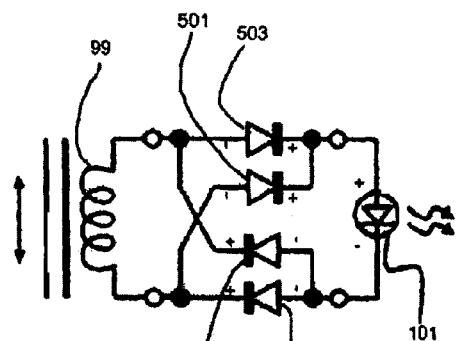
FIGS. 10C and 10D illustrate light emitting circuitry of the integrated light source utilizing rectification circuits in exemplary embodiments of the present invention.

A full bridge rectifier, such as the element 600 shown in FIG. 7E, may include 4 diodes 501, 503, 505, 507 that may be connected in such a way as to produce a full-wave rectified direct current voltage signal at the light source 101 from the ac current voltage signal generated by the illumination energy coil 99, as illustrated in FIG. 10C. The various circuit connections and one possible polarity arrangement of the diodes 501, 503, 505, 507 the illumination energy coil 99 and the light source 101. It is also conceived that an opposite polarity arrangement may also be utilized while producing identical physical arrangement and performance.

FIG. 7E illustrates an embodiment of the illumination energy bobbin 126 of FIG. 7C. As shown, the bobbin 126 may include a full-wave rectification circuit that may include a full bridge rectifier element 600. The bridge rectifier 600 may include four diodes in an arrangement that may generate a full-wave rectified voltage signal from the ac current voltage signal generated by the illumination energy coil 99. The bridge rectifier 600 may be electrically interfaced to the illumination energy coil 99 through the ends of the coil 99a, 99b. The bridge rectifier 600 may further output a rectified voltage signal to the light source 101 through output electrodes 600a, 600b to electrodes 101a, 101b, respectively, of the light source 101.

Figure 10D:
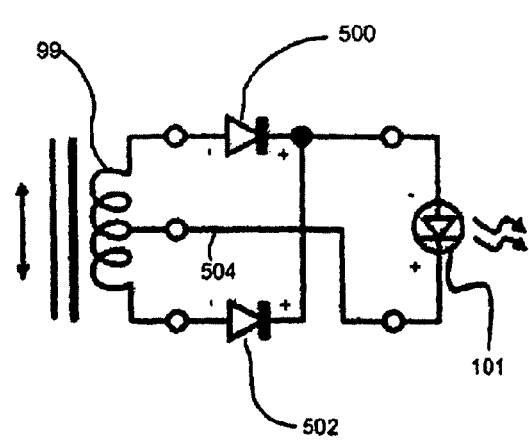

A center-tapped configuration may generate a full-wave rectified direct current voltage signal at the light source 101 from the ac current voltage signal generated by the illumination energy coil 99. The circuit diagram shown in FIG. 10D illustrates the various circuit connections and one possible polarity arrangement of the diodes 500, 502, the illumination energy coil 99 and the light source 101. It is also conceived that an opposite polarity arrangement may also be utilized while producing identical physical arrangement and performance.

Figures 7F, 8, 9:
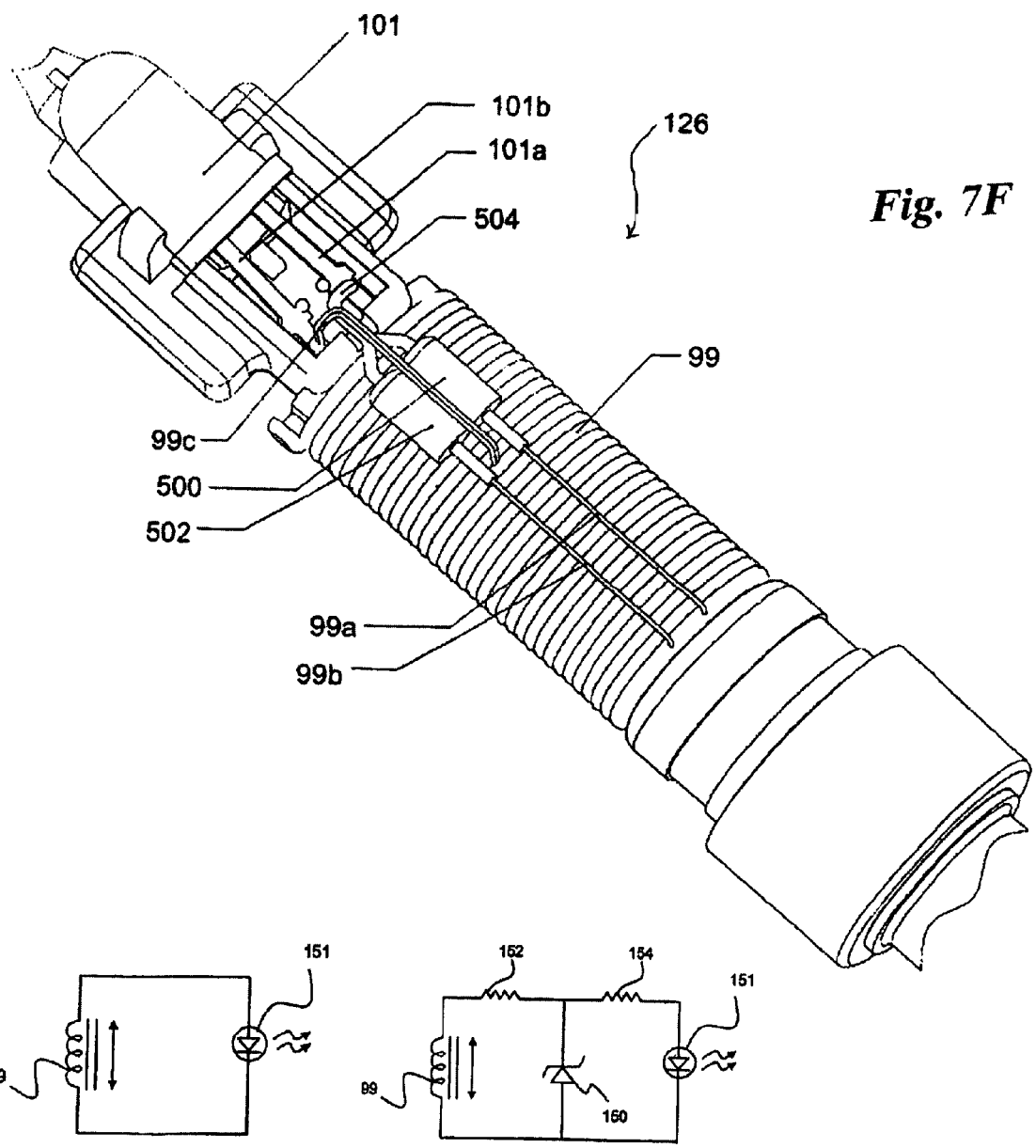
FIG. 7F illustrates the inclusion of a light source, a transducer and a center-tapped dual diode rectification circuit.
FIGS. 8 and 9 illustrate light emitting circuitry of the integrated light source in exemplary embodiments of the present invention.

FIG. 7F illustrates another embodiment of the illumination energy bobbin 126 of FIG. 7C. As shown, the bobbin 126 may include a full-wave rectification circuit that may include a pair of diodes 500, 502. The pair of diodes 500, 502 may be connected to the illumination energy coil 99 and to the light source 101. The illumination energy coil 99 may, in an exemplary embodiment, be center-tapped by wire 99c that may lead to one of the electrodes 101b of the light source 101. The pair of diodes 500, 502 may also interface with the illumination energy coil 99 by joining two common polarity ends of the diodes 500, 502 to the ends of the coil 99a, 99b, respectively. The pair of diodes 500, 502 may further interface with the light source 101 at one electrode 101a by way of wire 504 that may join two common polarity ends of the diodes 500, 502.

In the light emitting circuitry of FIG. 8, the light source may be an LED 151 connected in series with the illumination energy coil 99. Since the LED 151 emits light in response only to a voltage having single polarity, it emits light only half the time since the illumination energy coil 99 generates an ac voltage signal. However, since the LED 151 switches off and on at ultrasonic frequency (e.g., 25 kHz), such rapid switching of the LED is generally imperceptible to human eyes, and the LED 151 would appear to be continuously on. In other embodiments, the light source 101 may be any other suitable light emitting device such as an incandescent lamp (e.g., halogen light bulb). With this embodiment, only half of the sc voltage is utilized and the other half is wasted. With the rectification circuitry discussed above, such switching is minimized or eliminated and the full-wave utilization of the ac voltage is substantially realized.

In the light emitting circuitry of FIG. 9, a zener diode 150 is connected in parallel to the LED 151 of the light source 101. A resistor 152 is connected between the illumination energy coil 99 and the zener diode 150, and a resistor 154 is connected between the zener diode 150 and the LED 151. The zener diode 150 clamps the voltage such that the voltage differential seen by the LED 151 does not rise over a certain predetermined voltage. This way, the brightness of the LED 151 may be kept substantially uniform even if the energy illumination coil 99 begins to generate higher voltage due to any fluctuation of the energy source 14 or other environmental conditions. By way of example, the zener diode 150 may clamp the voltage at 5 volts (V), such that the voltage seen by the LED 151 is no greater than 5V. This voltage smoothing circuitry may be used in conjunction with the rectification circuitry discussed above.

As noted, a light source 101 may be a single light source or a plurality of light sources. Each light source may also be a single LED, multiple LEDs or arrays, as exemplified in FIG. 10. The multiple LEDs 151, 161, may be arranged in any manner, for example, in a compact arrangement to minimize the overall size of the light source 101, as shown in FIG. 4E. Concentric arrays of LEDs (not specifically shown, but may be arranged as shown in FIG. 4E) may also be used with arrangements, for example, controlled by a microprocessor, such that the areas of illumination may be varied as needed. A light transport apparatus 311, as shown in FIG. 22B, may also be used so that the LEDs 151 may be located inside the connecting body to minimize the size of the protrusion of the tip 102, in one embodiment of the invention. The transport apparatus 311, if the light source 101 is mounted distal to the tip 102, may also include filters or reflectors to vary the size of the area of illumination. Light source 101 as used herein FIGS. 8, 9, 10, 10A, 10B, 10C and 10D, denotes the source of illumination such as the LED(s) 151, or the light transport apparatus, or combinations thereof.

In FIG. 10, an LED 161 is connected in anti-parallel relationship with the LED 151, i.e., they are connected in parallel but in opposite directions, as discussed above, so that the LEDs 151 and 161 are alternately turned on in response to the ac voltage generated by the illumination energy coil 99. Since the ac voltage has an ultrasonic frequency (e.g., 25 kHz), the switching on and off of the LEDs 151 and 161 is imperceptible to human eyes, and therefore, both the LEDs 151 and 161 would appear to be on continuously. This exemplifies another form of full-wave utilization of the ac voltage. In other embodiments, again, the zener diode 150 may be used in parallel with each of the LEDs 151 and 161 in FIG. 9 so as to clamp the voltage for both the LEDs 151 and 161.

In further embodiments, the light emitting circuitry may include voltage smoothing means. Voltage smoothing means may, for example, include a reservoir capacitor, a capacitor-input filter and/or any other circuit elements that may substantially smooth or lessen the variance in output voltage signal generated by the illumination energy coil 99. Such voltage smoothing means may operate in general by utilizing variations in the potential of an input voltage signal and may store energy during at least a part of the voltage signal while releasing stored energy during at least another part of the voltage signal. Voltage smoothing circuitry may include capacitors, inductors and/or any other appropriate circuit elements that may aid in responding to varying electrical potentials and/or storing electrical energy.

FIGS. 10A and 10B show circuit diagrams of light emitting circuitry featuring examples of voltage smoothing means between illumination energy coil 99 and light source 101. FIG. 10A illustrates the use of a reservoir capacitor, which may substantially lessen the variation of the voltage signal observed at the light source 101.

FIG. 10B illustrates the use of a capacitor-input filter, which may include a reservoir capacitor as well as a filter capacitor and an inductor choke. The embodiments illustrated may also feature other circuitry, such as rectification means and may continue to function with voltage smoothing by preserving the proper electrical interactions between the components of the circuit.

Reductions in voltage variance at the light source may, for example, aid in increasing the effective lifespan of the light source by minimizing electrical stress due to input variance or "on/off" stress. Reducing voltage variance may also generate a more steady light output and may increase the overall light output over time.

The rectification circuitry discussed above is also effective in realizing full-utilization of the ac voltage generated. A magnetic source may also be used to increase the brightness of the light source.

In one aspect, the ultrasonic dental tool 10 includes monitoring systems for tool usage and condition. The dental tool 10 may include, for example, usage time monitoring circuitry, wear usage circuitry, electromagnetic monitoring circuitry and/or any other appropriate monitoring systems.

Figure 15:
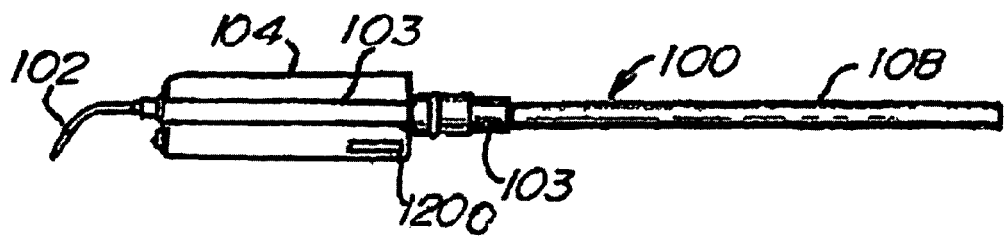
FIGS. 15, 15A, 15B, 15C and 15D each illustrates another embodiment of the ultrasonic dental tool of the present invention, including monitoring and indication functions.
Figure 15A:
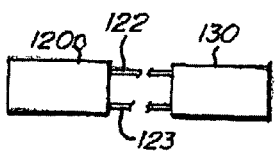
Figure 15B:
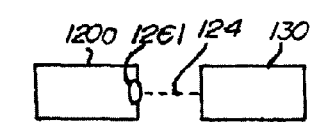

In one embodiment, the ultrasonic dental insert 100 includes a monitoring circuit 1200, as shown in FIG. 15. The monitoring circuit 1200 may generally include, for example, an integrated circuit (IC) chip (not specifically shown). The IC chip may be, for example, a memory chip, an electromechanical sensor and/or any other appropriate monitoring device. In general, the IC chip may monitor a characteristic(s) of the insert 100, such as its duration of use, usage frequency, power level, stroke amplitude, and/or any other appropriate characteristic. The monitoring circuit 1200 may be disposed on or in the housing 104 of the insert 100. In some embodiments, the monitoring circuit 1200 may be substantially self-contained within the housing 104 such that it may be isolated from outside contamination or conditions, such as the moist or wet environment during use of the insert 100, or the wet, high temperature environment of autoclave sterilization. In other embodiments, the monitoring system 130 or portions thereof, as shown in FIG. 15*a* and FIG. 15*b*, may be in the handpiece 200. In general, the monitoring circuit 1200 may be disposed such that the IC chip may properly monitor a given characteristic of the insert 100. This may include, for example, being in close proximity to the tool tip 102 or connecting body 103 to monitor electromechanical characteristics during use.

The monitoring circuit 1200 may be connected to a monitoring system 130, as shown in FIGS. 15A and 15B. The monitoring system 130 may generally be disposed on or in the ultrasonic unit 14 and it may also have portions disposed on or in the handpiece 200, as noted above. The monitoring system 130 may be, for example, part of the monitoring circuit 1200 of the insert 100 or it may be a control or indicator system for the monitoring circuit 1200.

The monitoring circuit 1200 may be connected for communication to the system 130 by any appropriate system, which may include, but are not limited to, electrical conductors, such as electrical wires 122, 123 in FIG. 15*a*, magnetic or physical contacts, such as, for example, actuators (not shown), or wireless communication, such as, for example, radio frequency transmission (RF), infrared transmission, Bluetooth wireless, and/or any other appropriate system, as illustrated with wireless communication line 124 in FIG. 15B. The monitoring circuit 1200 may include an antenna 1261 to send and/or receive transmissions.

In general, the monitoring circuit 1200 may be powered by any appropriate power source, such as, for example, a battery, a capacitor, a transducer, an external source and/or any other appropriate source.

In one embodiment, monitoring circuit 1200 of FIGS. 15, 15A and 15B is a time monitoring circuit. The time monitoring circuit may record the usage time of an ultrasonic dental insert 100. The time monitoring circuit may include an integrated circuit (IC) chip 1200 and monitoring system 130 which may be an electrical signal source. The electrical signal source 130 may supply the IC chip of the monitoring circuit 1200 with a duration signal. The duration signal may be supplied by the electrical signal source 130 when the ultrasonic dental insert 100 is in use. The IC chip of the monitoring circuit 1200 may then record the length of time of the signal and thus may record the duration of use of an ultrasonic dental insert 100. The IC chip of the monitoring circuit 1200 may further generate a return signal which may indicate the total recorded time. The ultrasonic unit 14 may also include a notification or indication system for informing a user of the state of the insert 100, which may, for example, include a suggestion for replacing the insert.

In another embodiment, monitoring system 130 of the ultrasonic unit 14 may be a time monitoring circuit which may record the duration of use of the unit 14. In particular, the time monitoring circuit 1200 may record the duration of a usage cycle (e.g. the time between activating the insert 100 and deactivating the insert 100). The time monitoring circuit 1200 may then transmit the duration information to an IC chip of the monitoring circuit 1200 on the insert 100, which may record an integrated time duration of the usage of insert 100 by summing the usage times transmitted by the time monitoring circuit 1200.

In some embodiments, the IC chip of the monitoring circuit 1200 may provide a predetermined maximum usage time that may limit the duration of use of the ultrasonic dental insert 100. The IC chip of the monitoring circuit 1200 may, for example, generate a control signal which may prevent the usage of the ultrasonic dental insert 100 by an ultrasonic unit or handpiece when the maximum usage time has been reached, or it may cause the unit 14 to indicate that the insert 100 may need replacement via an at least one indicator 15, as shown in FIG. 1.

In another embodiment, the monitoring circuit 1200 includes a sensor(s) which may detect electromechanical characteristics of the insert 100. Measured electromechanical characteristics may include, but are not limited to, power level, stroke amplitude, vibration frequency, and/or any other appropriate characteristic. Alternatively, the monitoring system 130 in the ultrasonic unit 14 may include a sensor(s).

In one embodiment, the ultrasonic dental unit 14 may include systems for storing established reference values for insert electromechanical characteristics and comparing them to the detected values from the insert 100. The unit 14 may then determine whether the insert 100 is performing within or outside a predetermined acceptable range of performance and may indicate via an at least one indicator 15 to a user the status of the insert 100. This detection may be performed on either a new or used insert 100.

Figure 15C:
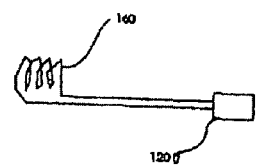

In still another embodiment, the monitoring circuit 1200 may include a coil 160, as shown in FIG. 15C. The coil 160 may be disposed in proximity to the insert 100 and may in general be utilized to detect electrical characteristics of the insert 100. The coil 160 may, for example, exhibit an electric current in response to the electromagnetic field of the coil in the handpiece 200 and/or to the ultrasonic vibrations of ferromagnetic components of the insert 100, which may include the tool tip 102 and/or the connecting body 103. The electric current in the coil 160 may be analyzed by the monitoring circuit 1200 and/or the monitoring system 130 of the unit 14 to determine electrical characteristics of the insert 100. The electric current may also power the monitoring circuit 1200.

In another aspect, the monitoring circuit 1200 of the insert 100 may be externally powered. Ultrasonic inserts are typically autoclaved for sterilization and the harsh environment of the autoclave may be detrimental to an internal power source, such as a battery. The monitoring circuit 1200 of the insert 100 may, for example, draw power from the ultrasonic unit 14 via electrical conductors 122, 123, as shown in FIG. 15A.

In some embodiments, the monitoring circuit 1200 may be wireless and may be externally powered by a wireless power source. A wireless power source may include, for example, an electromagnetic field. A wireless monitoring circuit 1200 may generally include an antenna 1261, as shown in FIG. 15*b*. The antenna 1261 may be utilized for transmitting and/or receiving communication signals with a monitoring system 130. The antenna 1261 may further be utilized to power the wireless monitoring circuit 1200 by converting an electromagnetic field, such as a wireless communication signal, into electric current.

In one embodiment, a coil 160 may be utilized as an antenna and a power source, as described above in regard to FIG. 15C.

In another embodiment, the monitoring circuit 1200 may include an energy dissipating system. IC chips may be subject to overpowering and/or electric shorting from an excess of electric current. This may be particularly problematic in systems such as IC chips that are wirelessly powered by antennas and/or coils. An energy dissipating system may be included to consume at least a portion of the electric current that would be provided to a monitoring circuit 1200. This may aid in preventing overpowering and/or shorting of components of the monitoring circuit, such as, for example, an IC chip. An energy dissipating system may include, but is not limited to, resistors, inductors, capacitors, combinations thereof, and/or any other appropriate system.

Figure 15D:
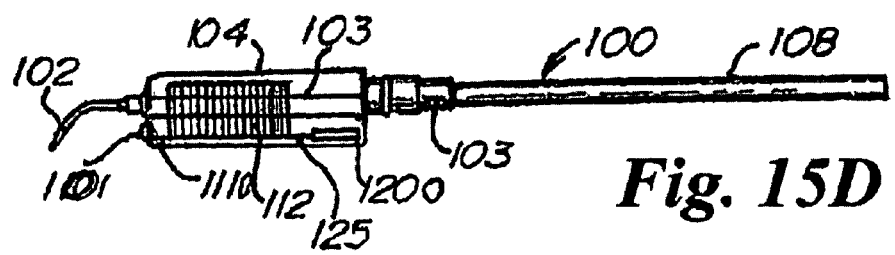

In still another embodiment, the insert 100 includes a light source 101 as shown in FIG. 15D. The light source 101 may share a power source with a monitoring circuit 1200 and may further act as an energy dissipating system by consuming electric current and converting the energy into light. The light source 101 may in general be disposed on the insert 100 such that it may direct light onto the field of work. In an exemplary embodiment, a light source 101 may be located proximal to the tool tip 102, as shown in FIG. 15D.

In one aspect, the power source may be, for example, a coil 112. The coil 112 may draw power in a manner similar or identical to the coil 160 discussed above and may provide power to the light source 101 and the monitoring circuit 1200 via conductors 1110, 125, respectively.

FIG. 15E is a block diagram of an embodiment of the ultrasonic unit control system 690 of the ultrasonic dental tool 10 of the present invention. In one embodiment, the microelectronics of the control system 690 are located in the ultrasonic unit 14, as illustrated in FIG. 1. In another embodiment, the microelectronics of the control system 690 are located in the handpiece 200. Other locations for the control system electronics are possible within the scope of the invention.

The control system 690 includes a CPU 700, program memory logic 702, an I/O logic device 704, a data bus 706 and system indicators 708. The CPU 700, program memory logic 702, and the I/O logic device 704 are connected to the data bus 706. The I/O logic device 704 is further connected to system indicators 708. In one embodiment of the invention, the I/O logic device 704 further includes device drivers. The I/O logic device 704 is further connected to the memory integrated circuit 212, which may be disposed on an ultrasonic insert 100. Ultrasonic unit controls 710 are connected to the I/O device 704. A power source 712 provides power to the CPU 700, program memory logic 702, the I/O logic device 704 and the memory integrated circuit 212.

The CPU 700, program memory logic 702 and the I/O logic device 704 are for example, microelectronic devices, located in the ultrasonic unit 14. In an alternative embodiment of the invention, the ultrasonic unit controls 710 and power source 712 are also located in the ultrasonic unit 14. In an alternative embodiment of the invention, the CPU 700, program memory logic 702, I/O logic device 704, ultrasonic unit controls 710, and power 712 are, for example, located in the handpiece 200. The ultrasonic unit controls 710 are, for example, at least one transistor device or electronic or electro-mechanical relay device for controlling the on/off function of the ultrasonic unit 14. The system indicators 708 are, for example, the lighted indicators on the ultrasonic unit 14 or, for example, the handpiece 200.

Figure 19:
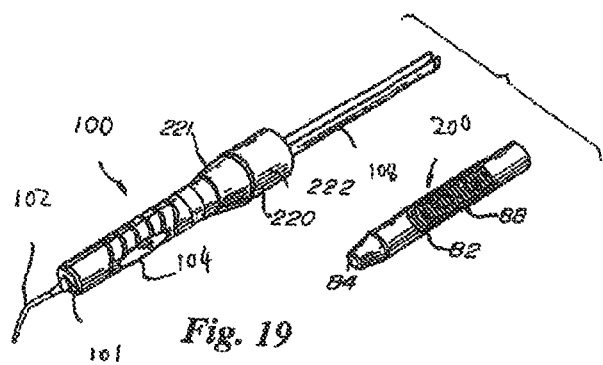
FIG. 19 illustrates a partial exploded view of an embodiment of an ultrasonic dental insert with an integral sheath.

In FIG. 19, an ultrasonic dental insert 100 having a grip portion or housing 104 and a connecting body 103 (not specifically shown) having a proximal end and a distal end having a tip 102 attached thereto or formed thereon is exemplified. The proximal end of the connecting body 103 is attached to a transducer 108 so as to generate the ultrasonic vibrations therefrom and to transmit the ultrasonic vibrations toward the tip 102 attached to the distal end. The insert 100 may also include a light source 101. The insert 100 may include a sheath 220.

Figure 20:
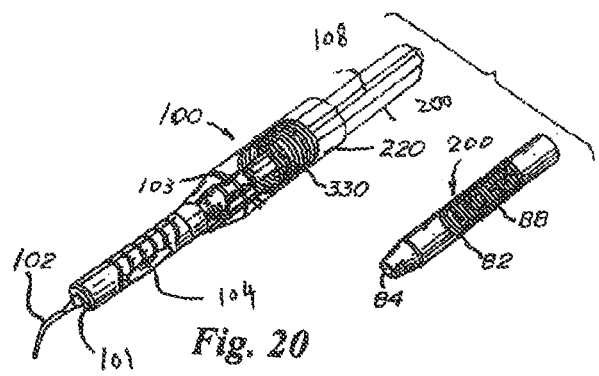
FIG. 20 shows a partial see-through perspective view of an insert with an integral sheath, illumination energy coil and a light source inserted into a handpiece.

In one aspect, the illumination energy coil 330 may be supported by a sheath 220 integral to the ultrasonic dental insert 100, as shown in FIG. 20. In one embodiment, the illumination energy coil 330 may be contained within the sheath 220, which may position the coil 330 for inductive coupling to the primary coil 88 of the handpiece 200 when the insert 300 is inserted into the handpiece 200. In another embodiment, the coil 330 may be disposed on the inner surface of the sheath 220. The sheath 220 may, for example, be overmolded over the coil 330. The sheath 220 may also be partially molded onto the insert 100 and the coil 330 may then be wound onto the partially molded sheath 220. The remainder of the sheath 220 may then be overmolded over the coil 330 such that it may be embedded in the material of the sheath 220. In general, the coil 330 may be disposed between the handpiece 200 and at least a portion of the sheath 220 and/or otherwise supported by the sheath 220.

In one aspect, the sheath 220 may be formed such that it may cover at least part of a handpiece housing 82 when inserted into a handpiece 200. In general, the sheath 220 may serve as a barrier such that it may reduce cross-contamination to and from the patient's mouth. The insert 100 may, for example, be sterilized prior to use by methods such as autoclaving, alcohol sterilization, and/or any other appropriate method such that when the sheath covers the handpiece 200, it may provide a sterile surface that may be inserted into the patient's mouth, as noted before. The ultrasonic dental tool may then be used without sterilizing of the handpiece 100. The sheath 220 may also help to prevent contaminants from one patient's mouth from being transferred to another patient or to the work area by the handpiece 200.

Figure 21:
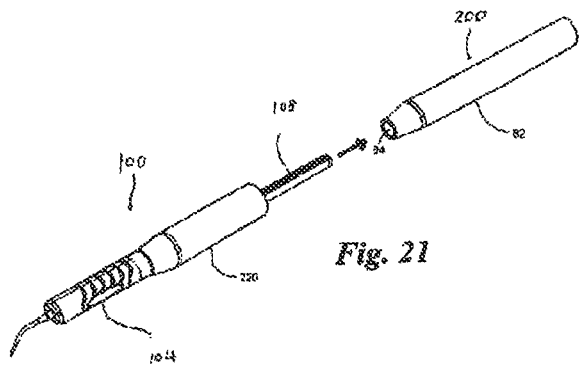
FIGS. 21 and 21A illustrate inserting an insert with an integral sheath into a handpiece.
Figure 21A:
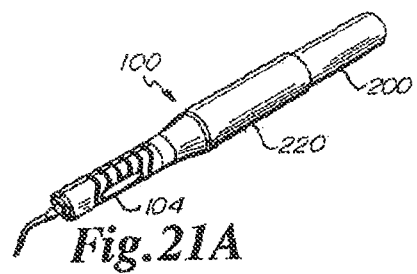

In an exemplary embodiment, as illustrated in FIGS. 21 and 21A, the sheath 220 may be integrally formed onto the insert 200 about the transducer 206 such that when the insert 200 is inserted into the handpiece 200, the sheath 220 may simultaneously cover at least a portion of the handpiece housing 82 while the transducer 108 is inserted into aperture 84 the handpiece 200. The sheath 220 may be formed as part of a handgrip portion of the insert housing 104. The sheath 220 may also be supported by other portions of the insert 200.

Figure 21B:
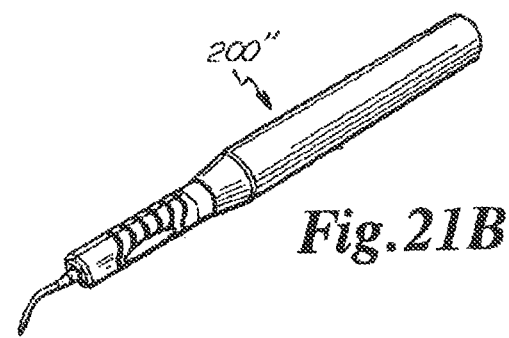
FIG. 21B illustrates an embodiment of an insert having an integral sheath with one length.

In some embodiments, the sheath 220 may have a generally cylindrical section 222 with a hollow interior 224 which may fit over the handpiece housing 82, as exemplified in FIG. 19. The sheath 220 may generally include an expansion section 221 which may span the size difference between the insert housing 104 and the section 222 (which may be larger than the handpiece housing 82). The sheath 220 may be of any desirable length and may cover only a portion of the proximal end of the handpiece housing 82, as shown in FIG. 21a. The sheath 220 may also be of a length sufficient to cover substantially the entire length of the handpiece housing 82, as shown in FIG. 21B.

In some embodiments, the sheath 220 may have a generally cylindrical section 222 with a hollow interior 224 which may fit over the handpiece housing 82, as exemplified in FIG. 19. The sheath 220 may generally include an expansion section 221 which may span the size difference between the insert housing 104 and the section 222 (which may be larger than the handpiece housing 82). The sheath 220 may be of any desirable length and may cover only a portion of the proximal end of the handpiece housing 82, as shown in FIG. 21*a*. The sheath 220 may also be of a length sufficient to cover substantially the entire length of the handpiece housing 82 of the handpiece 200", as shown in FIG. 21B.

Of course, the insert 100 having a sheath 220 may also have an illumination energy coil 99, for example, proximal to the connecting body 103, and generates a voltage signal in response to movement of a portion of the connecting body 103 according to the ultrasonic vibrations, and optionally, having a magnetic material or source 99, as discussed above and exemplified in FIGS. 7D1, 7D2, 7D3, 7D4 and 7D5.

It will be appreciated by those of ordinary skill in the art that the present invention may be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

What is claimed is:

1. An ultrasonic insert comprising:
   a motor for generating mechanical energy;
   a work tip;
   a coupling member disposed between said motor and said work tip, said coupling, member being adapted to receive mechanical energy from said motor; and
   an O-ring having an outer peripheral and an inner peripheral, disposed on the coupling member at its inner peripheral;
   wherein said coupling member comprises a groove having a contact surface of low coefficient of friction for seating the O-ring to facilitate rotation of the insert about the O-ring with a torque less than 500 g-cm, and wherein the inner peripheral of said O-ring has a lower coefficient of friction than the outer peripheral.

2. The ultrasonic insert of claim 1 wherein said coupling member further comprises a retaining ring and said groove is disposed on the retaining ring.

3. The ultrasonic insert of claim 1 wherein said contact surface of said groove comprises a coating of a material having a low coefficient of friction.

4. The ultrasonic insert of claim 1 further comprising:
   an electrical generator disposed substantially proximate to the coupling member for generating a voltage signal in response to movement of a portion of the coupling member; and
   at least one light source having an electrical input electrically coupled to said electrical generator.

5. The ultrasonic insert of claim 4 further comprising an electrical conductor having a first end electrically coupled to said electrical generator, said electrical conductor comprises a rectifier circuit.

6. The ultrasonic insert of claim 4 wherein said at least one light source comprises two light sources in an anti-parallel arrangement.

7. The ultrasonic insert of claim 4 further comprising a magnetic material, said material being permanently or removably attached to the insert.

8. The ultrasonic insert of claim 1 wherein said contact surface of low coefficient of friction comprises a material selected from the group consisting of condensation copolymers of a diamine and a dicarboxylic acid; high density polyethylene; polyxylylene; and fluoro-polyethylenes.

9. The ultrasonic dental insert of claim 1 further comprising a one piece nonmetallic bobbin disposed on said coupling member.

10. An ultrasonic dental tool comprising:
    a dental handpiece having a substantially cylindrical shape with a substantially hollow interior; and
    an insert partially disposed inside the handpiece, said insert comprising:
    a first transducer for generating ultrasonic vibrations;
    a connecting body having a proximal end and a distal end having a tip thereon, said proximal end attached to said first transducer so as to receive said ultrasonic vibrations therefrom and to transmit said ultrasonic vibrations toward the tip at said distal end;
    an O-ring disposed on said connecting body, said O-ring having an outer peripheral and an inner peripheral; and
    a groove having a contact surface of low coefficient of friction in contact with the inner peripheral of the O-ring to facilitate rotation between the O-ring and rest of the insert inside the handpiece with a torque less than 500 g-cm, and wherein the inner peripheral of said O-ring has a lower coefficient of friction than the outer peripheral;
    wherein the outer peripheral of said O-ring seals the insert inside the handpiece.

11. The ultrasonic dental tool of claim 10 wherein said contact surface of said groove comprises a coating of a material having a low coefficient of friction.

12. The ultrasonic dental tool of claim 10 wherein said contact surface of low coefficient of friction comprises a low frictional material.

13. The ultrasonic dental tool of claim 10 further comprising:
    at least a portion of a monitoring mechanism about the connecting body; and
    an ultrasonic unit for supplying power to said handpiece;
    wherein said monitoring mechanism monitors at least one electromechanical characteristic or duration of use of said dental insert and communicates said characteristic or duration to said ultrasonic unit for indication to a user.

14. The ultrasonic dental tool of claim 13 wherein said monitoring mechanism comprises at least one integrated circuit chip.

15. The ultrasonic dental tool of claim 14 wherein said at least one integrated circuit chip is a memory chip for storing duration of use information of said dental insert.

16. The ultrasonic dental tool of claim 13 wherein said at least a portion of said monitoring mechanism of said dental insert communicates with said ultrasonic unit via a wired or wireless connection.

17. An ultrasonic dental tool comprising:
    a dental handpiece having a substantially cylindrical shape with a substantially hollow interior; and
    an insert partially disposed inside the handpiece, said insert comprising:
    a first transducer for generating ultrasonic vibrations;
    a connecting body having a proximal end and a distal end, the proximal end being attached to said first transducer so as to receive the ultrasonic vibrations from said first transducer and to transmit the ultrasonic vibrations toward a tip at the distal end;
    an O-ring having an outer peripheral and an inner peripheral, disposed on the connecting body at its inner peripheral;

a second transducer for generating a voltage signal in response to movement of a portion of the connecting body according to the ultrasonic vibrations, said second transducer comprises a one-piece cylindrical structure for sliding onto said connecting body;

at least one light source substantially proximate to the tip and receiving the voltage signal from the second transducer to generate light; and at least one magnetic material in close proximity to the connecting body and the light source;

wherein said connecting body comprises a groove having a contact surface of low coefficient of friction for seating the O-ring to facilitate rotation of the insert about the O-ring with a torque less than 500 g-cm, and wherein the inner peripheral of said O-ring has a lower coefficient of friction than the outer peripheral.

18. The ultrasonic tool of claim 17 wherein said contact surface of low coefficient of friction comprises a low frictional material.

* * * * *